(12) United States Patent
Ogiwara et al.

(10) Patent No.: US 10,811,616 B2
(45) Date of Patent: *Oct. 20, 2020

(54) ORGANIC ELECTROLUMINESCENT ELEMENT AND ELECTRONIC DEVICE

(71) Applicant: IDEMITSU KOSAN CO., LTD., Chiyoda-ku (JP)

(72) Inventors: Toshinari Ogiwara, Sodegaura (JP); Kei Yoshida, Sodegaura (JP); Ryohei Hashimoto, Sodegaura (JP); Yumiko Mizuki, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/866,616

(22) Filed: Jan. 10, 2018

(65) Prior Publication Data

US 2018/0130959 A1   May 10, 2018

Related U.S. Application Data

(63) Continuation of application No. 14/777,679, filed as application No. PCT/JP2014/084175 on Dec. 24, 2014, now Pat. No. 9,905,779.

(30) Foreign Application Priority Data

Dec. 26, 2013   (JP) ................................. 2013-270267
Mar. 14, 2014   (JP) ................................. 2014-052133

(51) Int. Cl.
*H01L 51/00*   (2006.01)
*C07D 405/14*   (2006.01)
(Continued)

(52) U.S. Cl.
CPC ........ *H01L 51/0072* (2013.01); *C07D 235/08* (2013.01); *C07D 307/91* (2013.01);
(Continued)

(58) Field of Classification Search
CPC . H01L 51/5096; C07D 307/91; C07D 403/14; C07D 405/14; C07D 487/14;
(Continued)

(56) References Cited

U.S. PATENT DOCUMENTS 7,201,975 B2   4/2007   Fujii
7,422,799 B2   9/2008   Mishima et al.
(Continued)

FOREIGN PATENT DOCUMENTS

CN   103443949 A   12/2003
CN   101682002 A   3/2010
(Continued)

OTHER PUBLICATIONS

Author(S): Nakagawa, Tetsuya; Adachi, Chihaya, Title: Control of energy levels in organic light-emitting materials aimed for new light emitting mechanism, Fain Kemikaru (2012), 41(2), 34-40, Publisher: Shi Emu Shi Shuppan (Year: 2012).*

(Continued)

*Primary Examiner* — Vongsavanh Sengdara
(74) *Attorney, Agent, or Firm* — Oblon, McClelland, Maier & Neustadt, L.L.P.

(57) ABSTRACT

An organic electroluminescence device includes: an anode; an emitting layer; and a cathode, the emitting layer containing a first material, a second material and a third material, the first material being a fluorescent material, the second material being a delayed fluorescent material, the third material having a singlet energy larger than a singlet energy of the second material.

77 Claims, 4 Drawing Sheets

(51) Int. Cl.

| | | |
|---|---|---|
| C07D 487/14 | (2006.01) | |
| C07D 235/08 | (2006.01) | |
| C07D 403/14 | (2006.01) | |
| C07D 307/91 | (2006.01) | |
| H01L 51/50 | (2006.01) | |
| C09K 11/06 | (2006.01) | |

(52) U.S. Cl.
CPC ......... *C07D 403/14* (2013.01); *C07D 405/14* (2013.01); *C07D 487/14* (2013.01); *C09K 11/06* (2013.01); *H01L 51/006* (2013.01); *H01L 51/0054* (2013.01); *H01L 51/0067* (2013.01); *H01L 51/0071* (2013.01); *H01L 51/0073* (2013.01); *H01L 51/0074* (2013.01); *H01L 51/0094* (2013.01); *H01L 51/5004* (2013.01); *H01L 51/5028* (2013.01); *C09K 2211/1007* (2013.01); *C09K 2211/1011* (2013.01); *C09K 2211/1014* (2013.01); *C09K 2211/1029* (2013.01); *C09K 2211/1059* (2013.01); *C09K 2211/1088* (2013.01); *C09K 2211/1092* (2013.01); *C09K 2211/1096* (2013.01); *H01L 51/0052* (2013.01); *H01L 51/0056* (2013.01); *H01L 51/5016* (2013.01); *H01L 51/5056* (2013.01); *H01L 51/5064* (2013.01); *H01L 51/5072* (2013.01); *H01L 51/5088* (2013.01); *H01L 51/5092* (2013.01); *H01L 51/5096* (2013.01); *H01L 2251/55* (2013.01)

(58) Field of Classification Search
CPC ............ C09K 11/06; C09K 2211/1007; C09K 2211/1011; C09K 2211/1014; C09K 2211/1029; C09K 2211/1059; C09K 2211/1088; C09K 2211/1092; C09K 2211/1096
See application file for complete search history.

(56) References Cited

U.S. PATENT DOCUMENTS

| | | | |
|---|---|---|---|
| 7,952,273 B2 | 5/2011 | Do et al. | |
| 8,643,268 B2 | 2/2014 | Ogiwara et al. | |
| 9,099,658 B2 | 8/2015 | Kawamura et al. | |
| 2002/0071963 A1 | 6/2002 | Fujii | |
| 2004/0104394 A1 | 6/2004 | Lin et al. | |
| 2005/0202277 A1 | 9/2005 | Mishima et al. | |
| 2008/0136321 A1 | 6/2008 | Do et al. | |
| 2008/0284318 A1 | 11/2008 | Deaton et al. | |
| 2009/0030202 A1 | 1/2009 | Iwakuma et al. | |
| 2012/0001536 A1 | 1/2012 | Zhang et al. | |
| 2012/0126222 A1* | 5/2012 | Ogiwara | H01L 51/5096 257/40 |
| 2012/0241732 A1* | 9/2012 | Endo | H01L 51/0072 257/40 |
| 2012/0248968 A1 | 10/2012 | Ogiwara et al. | |
| 2013/0270531 A1 | 10/2013 | Seo et al. | |
| 2013/0277654 A1* | 10/2013 | Seo | H01L 51/5016 257/40 |
| 2013/0306945 A1 | 11/2013 | Seo | |
| 2014/0034930 A1* | 2/2014 | Seo | H01L 51/0051 257/40 |
| 2014/0077172 A1 | 3/2014 | So et al. | |
| 2014/0103329 A1 | 4/2014 | Ogiwara et al. | |
| 2014/0175419 A1 | 6/2014 | Nakano et al. | |
| 2014/0183486 A1 | 7/2014 | Nakano et al. | |
| 2015/0115225 A1 | 4/2015 | Kawamura et al. | |
| 2016/0190478 A1* | 6/2016 | Nakanotani | H01L 51/5012 257/40 |

FOREIGN PATENT DOCUMENTS

| | | |
|---|---|---|
| CN | 102709485 A1 | 10/2012 |
| CN | 103280535 A | 9/2013 |
| CN | 203242670 U | 10/2013 |
| CN | 105453294 A | 3/2016 |
| EP | 2 980 877 A1 | 2/2016 |
| EP | 3 035 401 A1 | 6/2016 |
| JP | 2002-184581 A | 6/2002 |
| JP | 2003-77676 A | 3/2003 |
| JP | 2005-294249 A | 10/2005 |
| JP | 2008-147630 A | 6/2008 |
| JP | 2009-094124 A | 4/2009 |
| JP | 2013-116975 A | 6/2013 |
| JP | 5669163 B1 | 2/2015 |
| JP | 2015-179809 A | 10/2015 |
| KR | 10-2004-0023781 A | 3/2004 |
| KR | 10-2013-0116198 A | 10/2013 |
| KR | 10-2016-0044522 A | 4/2016 |
| WO | 2012/133188 A1 | 10/2012 |
| WO | 2012/153780 A1 | 11/2012 |
| WO | 2013/038650 A1 | 3/2013 |
| WO | WO 2013/154064 A1 | 10/2013 |
| WO | 2013/180241 A1 | 12/2013 |
| WO | 2015/022974 A1 | 2/2015 |
| WO | 2015/091716 A1 | 6/2015 |

OTHER PUBLICATIONS

Opposition notified issued Sep. 4, 2018 in corresponding Korean Patent No. 10-1831211, 25 pages (with unedited computer generated machine translation).
Third Party Observation issued Aug. 9, 2018 in corresponding European Patent Application No. 14874936.9, 4 pages.
Office Action dated Apr. 25, 2017 in Korean Patent Application No. 10-2015-7025439 (with English translation).
Extended European Search Report dated Aug. 30, 2016 in Patent Application No. 14874936.9.
A.K. Bansal et al., "Photodynamics of OLED Triplet Emitters Ir(ppy)$_3$ and PtOEP", Molecular Crystals and Liquid Crystals, vol. 467, XP055296871, ISSN: 1542-1406, DOI: 10.1080/15421400701220387, pp. 21-31 (2007).
Combined Chinese Office Action and Search Report dated Jun. 14, 2016 in Patent Application No. 201480017162.4 (with partial English language translation and English translation of categories of cited documents).
Computer Generated English Translation and Specification of JP Application No. 2013-168587, filed on Aug. 14, 2013. Subsequently withdrawn from issue. Provided for information only.
Computer Generated English Translation and Specification of JP Application No. 2014-038472, filed on Feb. 28, 2014. Subsequently withdrawn from issue. Provided for information only.
U.S. Appl. No. 14/911,761, filed Feb. 12, 2016, U.S. National Phase Application of PCT/JP2014/071373, Provided for information only.
Office Action dated Nov. 17, 2015 in Japanese Patent Application No. 2014-052133 (with English translaltion).
Adachi, Chihaya, ed., Yuki Hando-tai no Debaisu Bussei (Device Physics Semiconductors), Kodansha, pp. 261-268 (Mar. 22, 2012).
Adachi, Chihaya, et al., (ed.), Organic EL Symposium, proceeding for the tenth meeting, S2-5, pp. 11-12 (2010).
Tokumura, Katsumi (ed.), Yuki Hikari Kagaku Hanno-ron (Organic Photochemical Reaction Theory), Tokyo Kagaku Dojin Co., Ltd. (1973).
Combined Chinese Office Action and Search Report dated Feb. 24, 2018 in Chinese Patent Application No. 201611221800.1 (with English translation and English translation of Category of Cited Documents), 30 pages.
Japanese Office Action dated Mar. 13, 2018 in Japanese Patent Application No. 2016-054319 (with English translation), 5 pages.
Office Action dated Sep. 17, 2019 in Japanese Patent Application No. 2018-209666, 2 pages.
Office Action dated Apr. 15, 2019 in the corresponding European Application No. 14874936.9 5 pages.

(56) References Cited

OTHER PUBLICATIONS

Third Party Observation dated Apr. 15, 2019 in the corresponding European Application No. 14874936.9 5 pages.

* cited by examiner

ORGANIC ELECTROLUMINESCENT ELEMENT AND ELECTRONIC DEVICE

The present application is a continuation of U.S. patent application Ser. No. 14/777,679 filed on Sep. 16, 2015, which is a 35 U.S.C. § 371 national stage patent application of international patent application PCT/JP2014/084175, filed on Dec. 24, 2014, which claims priority to Japanese patent application JP 2014-052133, filed on Mar. 14, 2014, and Japanese patent application JP 2013-270267, filed on Dec. 26, 2013.

TECHNICAL FIELD

The present invention relates to an organic electroluminescence device and an electronic device.

BACKGROUND ART

When a voltage is applied to an organic electroluminescence device (hereinafter, occasionally referred to as "organic EL device"), holes and electrons are injected into an emitting layer respectively from an anode and a cathode. The injected holes and electrons are recombined to generate excitons in the emitting layer. According to the electron spin statistics theory, singlet excitons and triplet excitons are generated at a ratio of 25%:75%.

A fluorescent organic EL device, which uses emission caused by singlet excitons, is inferred to exhibit an internal quantum efficiency of 25% at a maximum. Although having been used in full-color displays of a mobile phone, TV and the like, a fluorescent EL device is required to use triplet excitons in addition to singlet excitons to further enhance efficiency.

In view of the above, a highly efficient fluorescent organic EL device using delayed fluorescence has been studied.

For instance, a thermally activated delayed fluorescence (TADF) mechanism has been studied. The TADF mechanism uses such a phenomenon that inverse intersystem crossing from triplet excitons to singlet excitons thermally occurs when a material having a small energy difference ($\Delta ST$) between singlet energy level and triplet energy level is used. As for thermally activated delayed fluorescence, refer to, for instance, "ADACHI, Chihaya, ed. (Mar. 22, 2012), Yuki Hando-tai no Debaisu Bussei (Device Physics of Organic Semiconductors), Kodansha, pp. 261-262."

For instance, Patent Literatures 1 to 3 disclose organic EL devices using the TADF mechanism.

Patent Literature 1 discloses an organic EL device including an emitting layer that contains a compound with a small $\Delta ST$ as a host material and a fluorescent compound as a dopant material. According to Patent Literature 1, when the TADF mechanism is generated by using a compound with a small $\Delta ST$ as a host material, the internal quantum efficiency is improved.

Patent Literatures 2 and 3 also each disclose an organic EL device including an emitting layer that contains a specific compound with a small $\Delta ST$ as a host material and a fluorescent compound as a dopant material. In Patent Literatures 2 and 3, the TADF mechanism is used to improve the performance of the organic EL device as in Patent Literature 1.

CITATION LIST

Patent Literature(S)

Patent Literature 1: International Publication No. WO2012/133188

Patent Literature 2: International Publication No. WO2013/180241

Patent Literature 3: Chinese Patent Application Publication No. 102709485

SUMMARY OF THE INVENTION

Problems to be Solved by the Invention

However, further improvement of an organic EL device in luminous efficiency is still demanded.

An object of the invention is to provide an organic electroluminescence device with improved luminous efficiency. Another object of the invention is to provide an electronic device provided with the organic electroluminescence device.

Means for Solving the Problems

According to an aspect of the invention, an organic electroluminescence device includes: an anode; an emitting layer; and a cathode, the emitting layer containing a first material, a second material and a third material, the first material being a fluorescent material, the second material being a delayed fluorescent material, the third material having a singlet energy larger than a singlet energy of the second material.

According to another aspect of the invention, an electronic device includes the organic electroluminescence device according to the above aspect.

The above aspect of the invention can provide an organic electroluminescence device with improved luminous efficiency.

DESCRIPTION OF EMBODIMENTS

An organic EL device according to an exemplary embodiment of the invention will be described below.

First Exemplary Embodiment

Arrangement(s) of Organic EL Device

Arrangement(s) of an organic EL device according to a first exemplary embodiment will be described below.

The organic EL device includes a pair of electrodes and an organic layer disposed between the electrodes. The organic layer includes a plurality of layers formed of an organic compound. The organic layer may further contain an inorganic compound.

The organic layer of the organic EL device of the exemplary embodiment includes at least one emitting layer. Specifically, for instance, the organic layer may consist of a single emitting layer, or may include layers usable in a typical organic EL device, such as a hole injecting layer, a hole transporting layer, an electron injecting layer, an electron transporting layer and a blocking layer.

Figure 1:
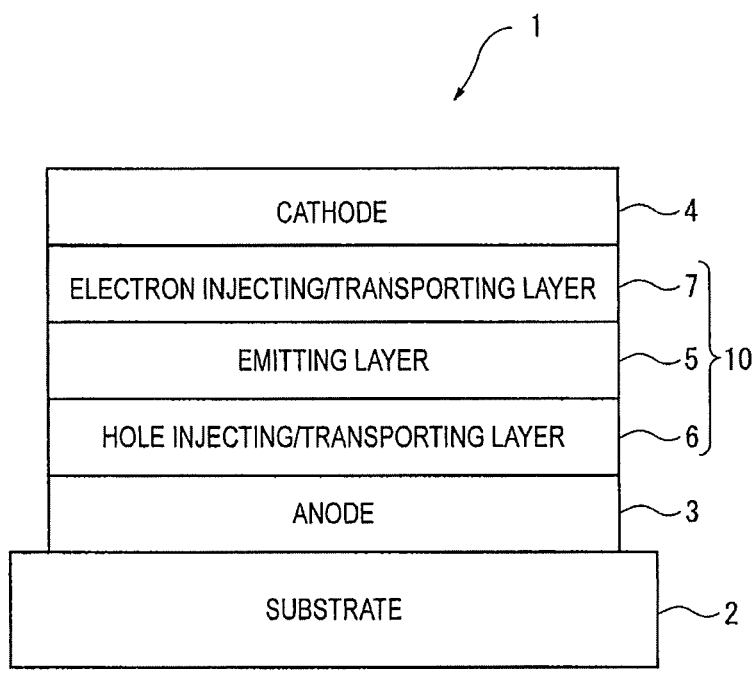
FIG. 1 schematically shows an exemplary arrangement of an organic electroluminescence device according to an exemplary embodiment.

FIG. 1 schematically shows an exemplary arrangement of an organic EL device according to the exemplary embodiment.

An organic EL device 1 includes a light-transmissive substrate 2, an anode 3, a cathode 4, and an organic layer 10 provided between the anode 3 and the cathode 4.

The organic layer 10 includes an emitting layer 5, a hole injecting/transporting layer 6 provided between the emitting layer 5 and the anode 3, and an electron injecting/transporting layer 7 provided between the emitting layer 5 and the cathode 4. In the organic EL device of the exemplary embodiment, the emitting layer 5 contains first, second and third materials. The emitting layer 5 may contain a phosphorescent metal complex. However, the organic EL device of the exemplary embodiment can exhibit an emitting performance superior to that of a typical fluorescent organic EL device even when the emitting layer 5 contains no phosphorescent metal complex.

The term "hole injecting/transporting layer" means at least one of a hole injecting layer and a hole transporting layer. The term "electron injecting/transporting layer" means at least one of an electron injecting layer and an electron transporting layer. Herein, when the hole injecting layer and the hole transporting layer are provided, the hole injecting layer is preferably provided between the anode and the hole transporting layer. When the electron injecting layer and the electron transporting layer are provided, the electron injecting layer is preferably provided between the cathode and the electron transporting layer. The hole injecting layer, the hole transporting layer, the electron transporting layer and the electron injecting layer may each consist of a single layer or may alternatively include a plurality of laminated layers.

Emitting Layer
First Material

In the exemplary embodiment, the first material is a fluorescent material.

The first material is not necessarily particularly limited, especially, in terms of luminescent color, but preferably emits a fluorescent light with a main peak wavelength of 550 nm or less, and more preferably emits a fluorescent light with a main peak wavelength of 480 nm or less. Especially, although a typical blue-emitting organic EL device entails a problem of improvement in luminous efficiency, the organic EL device of the exemplary embodiment is inferred to emit a blue light with an excellent luminous efficiency.

A main peak wavelength means a peak wavelength of luminescence spectrum exhibiting a maximum luminous intensity among luminous spectra measured using a toluene solution where the main material is dissolved at a concentration from $10^{-5}$ mol/l to $10^{-6}$ mol/l.

The first material preferably emits a blue fluorescent light. The first material preferably exhibits a high fluorescence quantum efficiency.

The first material of the exemplary embodiment may be a fluorescent material. Specific examples of the fluorescent material include a bisarylaminonaphthalene derivative, aryl-substituted naphthalene derivative, bisarylaminoanthracene derivative, aryl-substituted anthracenederivative, bisarylaminopyrene derivative, aryl-substituted pyrene derivative, bisarylaminochrysene derivative, aryl-substituted chrysene derivative, bisarylaminofluoranthene derivative, aryl-substituted fluoranthene derivative, indenoperylene derivative, acenaphthofluoranthene derivative, pyrromethene boron complex compound, compound having a pyrromethene skeleton, metal complex of a compound having a pyrromethene skeleton, diketopyrolopyrrol derivative, perylene derivative, and naphthacene derivative.

The first material of the exemplary embodiment may be a compound represented by a formula (10) below.

[Formula 1]

(10)

In the formula (10), $A_D$ is a substituted or unsubstituted aromatic hydrocarbon group having 12 to 50 carbon atoms forming the aromatic ring (i.e., ring carbon atoms). Examples of the aromatic hydrocarbon group having 12 to 50 ring carbon atoms for $A_D$ include groups derived from naphthalene, anthracene, benzanthracene, phenanthrene, chrysene, pyrene, fluoranthene, benzofluoranthene, perylene, picene, triphenylene, fluorene, benzofluorene, stilbene, naphthacene and acenaphthofluoranthene. $A_D$ may be a benzo group or a ring-expanded group prepared from an aromatic hydrocarbon having 12 to 50 ring carbon atoms.

In the formula (10), $B_D$ is represented by a formula (11) below.

In the formula (10), pa is an integer of 1 to 4, and pb is an integer of 0 to 4.

[Formula 2]

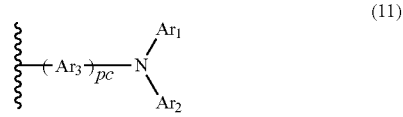

(11)

In the formula (11), $Ar_1$, $Ar_2$ and $Ar_3$ each independently represent a substituent selected from the group consisting of a substituted or unsubstituted aromatic hydrocarbon group having 6 to 50 ring carbon atoms, substituted or unsubstituted alkyl group having 1 to 50 carbon atoms, substituted or unsubstituted alkenyl group, substituted or unsubstituted alkynyl group, and substituted or unsubstituted heterocyclic group having 5 to 50 atoms forming a ring (i.e., ring atoms), and pc is an integer of 0 to 4. A wavy line in the formula (11) shows a bonding position with the aromatic hydrocarbon group represented by $A_D$.

In the formulae (10) and (11), a plurality of $A_D$ may be mutually the same or different, a plurality of $B_D$ may be mutually the same or different, a plurality of $Ar_1$ may be mutually the same or different, a plurality of $Ar_2$ may be mutually the same or different, a plurality of $Ar_3$ may be mutually the same or different, and a plurality of pc may be mutually the same or different.

Examples of the compound represented by the formula (10) include the following compounds, but the first material is not limited thereto. In the following compounds, $A_{D1}$ to $A_{D4}$ each independently represent the same as $A_D$, and $B_{D1}$ to $B_{D4}$ each independently represent the same as $B_D$.

[Formula 3]

$$A_D \quad A_{D1}\!-\!A_{D2} \quad A_{D1}\!-\!A_{D2}\!-\!A_{D3}$$

$$A_{D1}\!-\!A_{D2}\!-\!A_{D3}\!-\!A_{D4} \quad A_{D1}\!-\!A_{D2}\!-\!A_{D3} \quad B_{D1}\!-\!A_D$$
$$\qquad\qquad\qquad\qquad\qquad\quad |$$
$$\qquad\qquad\qquad\qquad\qquad A_{D4}$$

$$\qquad\qquad\qquad\qquad\qquad\qquad\quad B_{D4}$$
$$\qquad\qquad\qquad\qquad\qquad\qquad\quad |$$
$$B_{D1}\!-\!A_D \quad B_{D1}\!-\!A_D\!-\!B_{D3} \quad B_{D1}\!-\!A_D\!-\!B_{D3}$$
$$\quad |\qquad\qquad\quad |\qquad\qquad\qquad |$$
$$\;B_{D2}\qquad\quad\; B_{D2}\qquad\qquad\;\; B_{D2}$$

[Formula 4]

$$B_{D1}\!-\!A_{D1}\!-\!A_{D2} \quad B_{D1}\!-\!A_{D1}\!-\!A_{D2}$$
$$\qquad\qquad\qquad\qquad\qquad\quad |$$
$$\qquad\qquad\qquad\qquad\qquad B_{D2}$$

$$\qquad\qquad\qquad\qquad\qquad\qquad\quad B_{D3}$$
$$\qquad\qquad\qquad\qquad\qquad\qquad\quad |$$
$$B_{D1}\!-\!A_{D1}\!-\!A_{D2}\!-\!B_{D2} \quad B_{D1}\!-\!A_{D1}\!-\!A_{D2}$$
$$\qquad\qquad\qquad\qquad\qquad\qquad\;\; |$$
$$\qquad\qquad\qquad\qquad\qquad\qquad B_{D2}$$

$$\qquad\qquad\qquad\qquad\qquad B_{D1}\;\; B_{D3}$$
$$\qquad\qquad\qquad\qquad\qquad\;\;\backslash\;\;/$$
$$B_{D1}\!-\!A_{D1}\!-\!A_{D2}\!-\!B_{D3} \quad A_{D1}\!-\!A_{D2}$$
$$\qquad\qquad\qquad\qquad\qquad\;\;/\;\;\backslash$$
$$\qquad\qquad\qquad\qquad\qquad B_{D4}\;\; B_{D2}$$

$$\quad\; B_{D3}$$
$$\quad\;\; |$$
$$B_{D1}\!-\!A_{D1}\!-\!A_{D2}\!-\!B_{D4} \quad B_{D1}\!-\!A_{D1}\!-\!A_{D2}\!-\!B_{D3}$$
$$\quad\;\; |\qquad\qquad\qquad\qquad\qquad\;\; |\quad\;\; |$$
$$\;\; B_{D2}\qquad\qquad\qquad\qquad\quad B_{D2}\; B_{D4}$$

[Formula 5]

$$B_{D1}\!-\!A_{D1}\!-\!A_{D2}\!-\!A_{D3} \quad A_{D1}\!-\!A_{D3}\!-\!A_{D3}$$
$$\qquad\qquad\qquad\qquad\qquad\quad |$$
$$\qquad\qquad\qquad\qquad\qquad B_{D1}$$

$$B_{D1}\!-\!A_{D1}\!-\!A_{D2}\!-\!A_{D3} \quad B_{D1}\!-\!A_{D1}\!-\!A_{D2}\!-\!A_{D3}$$
$$\quad\;\; |\qquad\qquad\qquad\qquad\qquad\qquad\quad |$$
$$\;\; B_{D2}\qquad\qquad\qquad\qquad\qquad\quad B_{D2}$$

$$\qquad\qquad\qquad\qquad\qquad\qquad\quad B_{D3}$$
$$\qquad\qquad\qquad\qquad\qquad\qquad\quad |$$
$$B_{D1}\!-\!A_{D1}\!-\!A_{D2}\!-\!A_{D3}\!-\!B_{D2} \quad B_{D1}\!-\!A_{D1}\!-\!A_{D2}\!-\!A_{D3}$$
$$\qquad\qquad\qquad\qquad\qquad\qquad\qquad\qquad\;\; |$$
$$\qquad\qquad\qquad\qquad\qquad\qquad\qquad\quad B_{D2}$$

$$\qquad B_{D3}\qquad\qquad\qquad\qquad\qquad\; B_{D3}$$
$$\qquad\;\; |\qquad\qquad\qquad\qquad\qquad\qquad |$$
$$B_{D1}\!-\!A_{D1}\!-\!A_{D2}\!-\!A_{D3} \quad B_{D1}\!-\!A_{D1}\!-\!A_{D2}\!-\!A_{D3}$$
$$\qquad\;\; |\qquad\qquad\qquad\qquad\qquad\qquad |$$
$$\qquad B_{D2}\qquad\qquad\qquad\qquad\qquad B_{D2}$$

$$B_{D1}\!-\!A_{D1}\!-\!A_{D2}\!-\!A_{D3}\!-\!B_{D3}$$
$$\qquad\;\; |$$
$$\qquad B_{D2}$$

[Formula 6]

$$\quad\; B_{D3}\qquad\qquad\qquad\qquad B_{D3}\; B_{D4}$$
$$B_{D1}\;\;\;|\qquad\qquad\qquad\qquad\quad\;\;\backslash\;/$$
$$\;\backslash A_{D1}\!-\!A_{D2}\!-\!A_{D3} \quad B_{D1}\!-\!A_{D1}\!-\!A_{D2}\!-\!A_{D3}$$
$$\;/\quad |\qquad\qquad\qquad\qquad\qquad\qquad |$$
$$B_{D4}\; B_{D2}\qquad\qquad\qquad\qquad\qquad B_{D2}$$

$$\qquad B_{D3}\;\;\;\;\; B_{D4}\qquad\qquad\qquad\;\; B_{D4}$$
$$\qquad\;\; |\qquad\quad\; |\qquad\qquad\qquad\qquad |$$
$$B_{D1}\!-\!A_{D1}\!-\!A_{D2}\!-\!A_{D3} \quad B_{D1}\!-\!A_{D1}\!-\!A_{D2}\!-\!A_{D3}$$
$$\qquad\;\; |\qquad\qquad\qquad\qquad\qquad\;\; |\quad\;\;\; |$$
$$\qquad B_{D2}\qquad\qquad\qquad\qquad\quad B_{D2}\; B_{D3}$$

$$\qquad\qquad\qquad B_{D4}$$
$$\qquad\qquad\qquad\;\; |$$
$$B_{D1}\!-\!A_{D1}\!-\!A_{D2}\!-\!A_{D3} \quad B_{D1}\!-\!A_{D1}\!-\!A_{D2}\!-\!A_{D3}\!-\!B_{D4}$$
$$\qquad\;\; |\qquad\;\; |\qquad\qquad\qquad\qquad |\quad\;\;\; |$$
$$\qquad B_{D2}\; B_{D3}\qquad\qquad\qquad\quad B_{D2}\; B_{D3}$$

$$\qquad\qquad\qquad B_{D4}\qquad\qquad\quad\;\; B_{D3}$$
$$\qquad\qquad\qquad\;\;\;\backslash\;B_{D3}\qquad\qquad\;\; |$$
$$B_{D1}\!-\!A_{D1}\!-\!A_{D2}\qquad\quad B_{D1}\!-\!A_{D1}\!-\!A_{D2}\!-\!A_{D3}\!-\!B_{D3}$$
$$\qquad\;\; |\;\;\;/\qquad\qquad\qquad\qquad\; |$$
$$\qquad B_{D2}\; A_{D3}\qquad\qquad\qquad\; B_{D2}$$

[Formula 7]

$$\qquad\quad\; B_{D4}\; B_{D3}$$
$$\qquad\qquad\;\;\backslash\;/$$
$$A_{D1}\!-\!A_{D2}\!-\!A_{D3}$$
$$\qquad\;/\;\;\backslash$$
$$\;\;\; B_{D1}\; B_{D2}$$

$$B_{D1}\!-\!A_{D1}\!-\!A_{D2}\!-\!A_{D3}\!-\!A_{D4} \quad A_{D1}\!-\!A_{D2}\!-\!A_{D3}\!-\!A_{D4}$$
$$\qquad\qquad\qquad\qquad\qquad\qquad\qquad\quad |$$
$$\qquad\qquad\qquad\qquad\qquad\qquad\quad B_{D1}$$

$$B_{D1}\!-\!A_{D1}\!-\!A_{D2}\!-\!A_{D3}\!-\!A_{D4} \quad B_{D1}\!-\!A_{D1}\!-\!A_{D2}\!-\!A_{D3}\!-\!A_{D4}$$
$$\qquad\;\; |\qquad\qquad\qquad\qquad\qquad\qquad\qquad\qquad\;\; |$$
$$\qquad B_{D2}\qquad\qquad\qquad\qquad\qquad\qquad\quad B_{D2}$$

$$B_{D1}\!-\!A_{D1}\!-\!A_{D2}\!-\!A_{D3}\!-\!A_{D4}$$
$$\qquad\qquad\qquad\;\; |$$
$$\qquad\qquad\quad B_{D2}$$

$$B_{D1}\!-\!A_{D1}\!-\!A_{D2}\!-\!A_{D3}\!-\!A_{D4}\!-\!B_{D2}$$

$$\qquad B_{D3}\qquad\qquad\qquad\qquad\qquad\qquad B_{D3}$$
$$\qquad\;\; |\qquad\qquad\qquad\qquad\qquad\qquad\;\;\; |$$
$$B_{D1}\!-\!A_{D1}\!-\!A_{D2}\!-\!A_{D3}\!-\!A_{D4} \quad B_{D1}\!-\!A_{D1}\!-\!A_{D2}\!-\!A_{D3}\!-\!A_{D4}$$
$$\qquad\;\; |\qquad\qquad\qquad\qquad\qquad\qquad\qquad\qquad |$$
$$\qquad B_{D2}\qquad\qquad\qquad\qquad\qquad\qquad\quad B_{D2}$$

$$\qquad\qquad\qquad B_{D3}$$
$$\qquad\qquad\qquad\;\; |$$
$$B_{D1}\!-\!A_{D1}\!-\!A_{D2}\!-\!A_{D3}\!-\!A_{D4}$$
$$\qquad\;\; |$$
$$\qquad B_{D2}$$

$$B_{D1}\!-\!A_{D1}\!-\!A_{D2}\!-\!A_{D3}\!-\!A_{D4}\!-\!B_{D3}$$
$$\qquad\;\; |$$
$$\qquad B_{D2}$$

$$\qquad\qquad\qquad B_{D3}\qquad\qquad\qquad\qquad\qquad\qquad\; B_{D3}$$
$$\qquad\qquad\qquad\;\; |\qquad\qquad\qquad\qquad\qquad\qquad\;\; |$$
$$B_{D1}\!-\!A_{D1}\!-\!A_{D2}\!-\!A_{D3}\!-\!A_{D4} \quad B_{D1}\!-\!A_{D1}\!-\!A_{D2}\!-\!A_{D3}\!-\!A_{D4}$$
$$\qquad\qquad\qquad\;\; |\qquad\qquad\qquad\qquad\qquad\qquad\;\; |$$
$$\qquad\qquad\quad B_{D2}\qquad\qquad\qquad\qquad\qquad\quad B_{D2}$$

[Formula 8]

$$A_{D1}\;\; B_{D3}\qquad\qquad\qquad\qquad B_{D1}\; B_{D3}$$
$$\;\;\backslash\;/\qquad\qquad\qquad\qquad\qquad\;\;\backslash\;/$$
$$A_{D2}\!-\!A_{D3}\!-\!A_{D4} \quad A_{D1}\!-\!A_{D2}\!-\!A_{D3}\!-\!A_{D4}$$
$$\;/\;\;\backslash\qquad\qquad\qquad\qquad\qquad\;/\;\;\backslash$$
$$B_{D1}\; B_{D2}\qquad\qquad\qquad\qquad\; B_{D4}\; B_{D2}$$

$$\qquad B_{D3}\;\; B_{D4}\qquad\qquad\qquad\quad B_{D3}\;\; B_{D4}$$
$$\qquad\;\; |\qquad |\qquad\qquad\qquad\qquad\;\; |\qquad |$$
$$B_{D1}\!-\!A_{D1}\!-\!A_{D2}\!-\!A_{D3}\!-\!A_{D4} \quad B_{D1}\!-\!A_{D1}\!-\!A_{D2}\!-\!A_{D3}\!-\!A_{D4}$$
$$\qquad\;\; |\qquad\qquad\qquad\qquad\qquad\qquad\qquad\;\; |$$
$$\qquad B_{D2}\qquad\qquad\qquad\qquad\qquad\qquad\quad B_{D2}$$

$$\qquad B_{D3}\qquad\;\; B_{D4}\qquad\qquad\qquad\;\; B_{D3}\; B_{D4}$$
$$\qquad\;\; |\qquad\qquad |\qquad\qquad\qquad\qquad\;\; |\quad\;\;\; |$$
$$B_{D1}\!-\!A_{D1}\!-\!A_{D2}\!-\!A_{D3}\!-\!A_{D4} \quad B_{D1}\!-\!A_{D1}\!-\!A_{D2}\!-\!A_{D3}\!-\!A_{D4}$$
$$\qquad\;\; |\qquad\qquad\qquad\qquad\qquad\qquad\qquad\;\; |$$
$$\qquad B_{D2}\qquad\qquad\qquad\qquad\qquad\qquad\quad B_{D2}$$

$$\qquad\qquad\qquad\qquad\quad B_{D4}$$
$$\qquad\qquad\qquad\qquad\quad\;\; |$$
$$B_{D1}\!-\!A_{D1}\!-\!A_{D2}\!-\!A_{D3}\!-\!A_{D4}\!-\!B_{D3}$$
$$\qquad\;\; |$$
$$\qquad B_{D2}$$

$$\qquad\qquad\qquad B_{D3}$$
$$\qquad\qquad\qquad\;\; |$$
$$B_{D1}\!-\!A_{D1}\!-\!A_{D2}\!-\!A_{D3}\!-\!A_{D4}$$
$$\qquad\;\; |\qquad\;\; |$$
$$\qquad B_{D2}\; B_{D4}$$

[Formula 9]

$$\qquad\qquad\qquad B_{D3}\qquad\qquad\qquad\qquad\; B_{D3}\;\;\; B_{D4}$$
$$\qquad\qquad\qquad\;\; |\qquad\qquad\qquad\qquad\qquad |\qquad\; |$$
$$B_{D1}\!-\!A_{D1}\!-\!A_{D2}\!-\!A_{D3}\!-\!A_{D4} \quad B_{D1}\!-\!A_{D1}\!-\!A_{D2}\!-\!A_{D3}\!-\!A_{D4}$$
$$\qquad\;\; |\qquad\qquad |\qquad\qquad\qquad\qquad\;\; |$$
$$\qquad B_{D2}\;\;\; B_{D4}\qquad\qquad\qquad\qquad B_{D2}$$

$$\qquad\qquad\qquad B_{D3}\;\;\; B_{D4}\qquad\qquad\quad B_{D1}\;\; B_{D3}$$
$$\qquad\qquad\qquad\;\; |\qquad\; |\qquad\qquad\qquad\;\;\backslash\;/$$
$$B_{D1}\!-\!A_{D1}\!-\!A_{D2}\!-\!A_{D3}\!-\!A_{D4} \quad A_{D1}\!-\!A_{D2}\!-\!A_{D3}\!-\!A_{D4}$$
$$\qquad\;\; |\qquad\qquad\qquad\qquad\qquad\;\;/\;\;\backslash$$
$$\qquad B_{D2}\qquad\qquad\qquad\qquad\quad B_{D4}\; B_{D2}$$

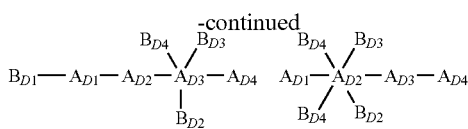

The aromatic hydrocarbon group for $A_D$ is preferably an aromatic hydrocarbon group having 12 to 30 ring carbon atoms, more preferably an aromatic hydrocarbon group having 12 to 24 ring carbon atoms, and further preferably an aromatic hydrocarbon having 18 to 20 ring carbon atoms. Examples of the aromatic hydrocarbon group for $A_D$ include a naphthylphenyl group, naphthyl group, acenaphthylenyl group, anthryl group, benzoanthryl group, aceanthryl group, phenanthryl group, benzo[c]phenanthryl group, phenalenyl group, fluorenyl group, picenyl group, pentaphenyl group, pyrenyl group, chrysenyl group, benzo[g]chrysenyl group, s-indacenyl group, as-indacenyl group, fluoranthenyl group, benzo[k]fluoranthenyl group, triphenylenyl group, benzo[b]triphenylenyl group, benzofluorenyl group, styrylphenyl group, naphthacenyl group and perylenyl group, and benzo groups and ring-expanded groups of these groups. The aromatic hydrocarbon group for $A_D$ is preferably any one of an anthryl group, picenyl group, pyrenyl group, chrysenyl group, fluoranthenyl group, benzo[k]fluoranthenyl group, benzofluorenyl group, styrylphenyl group, naphthacenyl group and perylenyl group, and benzo groups and ring-expanded groups of these groups, more preferably any one of an anthryl group, pyrenyl group, chrysenyl group, benzo[k]fluoranthenyl group, benzofluorenyl group, styrylphenyl group and acenaphtho[1,2-k]fluoranthenyl group, and benzo groups and ring-expanded groups of these groups, and especially preferably any one of an anthryl group, pyrenyl group, chrysenyl group, benzo[k]fluoranthenyl group, benzofluorenyl group, acenaphtho[1,2-k]fluoranthenyl group and naphthacenyl group.

The aromatic hydrocarbon group(s) (hereinafter, occasionally referred to as aryl group) for $Ar_1$, $Ar_2$ and $Ar_3$ is preferably each independently an aromatic hydrocarbon group having 6 to 24 ring carbon atoms, and more preferably an aromatic hydrocarbon group having 6 to 12 ring carbon atoms. The aromatic hydrocarbon group(s) for $Ar_1$, $Ar_2$ and $Ar_3$ may each independently be any one of a phenyl group, naphthylphenyl group, biphenylyl group, terphenylyl group, naphthyl group, acenaphthylenyl group, anthryl group, benzoanthryl group, aceanthryl group, phenanthryl group, benzo[c]phenanthryl group, phenalenyl group, fluorenyl group, picenyl group, pentaphenyl group, pyrenyl group, chrysenyl group, benzo[g]chrysenyl group, s-indacenyl group, as-indacenyl group, fluoranthenyl group, benzo[k]fluoranthenyl group, triphenylenyl group, benzo[b]triphenylenyl group, benzofluorenyl group, styrylphenyl group, naphthacenyl group and perylenyl group, and benzo groups and ring-expanded groups of these groups, among which a phenyl group, biphenyl group, terphenylyl group and naphthyl group are preferable, phenyl group, biphenyl group and terphenylyl group are more preferable, and a phenyl group is especially preferable.

Examples of the substituted aromatic hydrocarbon group include a phenylnaphthyl group, naphthylphenyl group, tolyl group, xylyl group, silylphenyl group, trimethylsilylphenyl group, 9,9-dimethylfluorenyl group, 9,9-diphenylfluorenyl group, 9,9'-spirobifluorenyl group and cyanophenyl group, among which, for instance, a tolyl group, xylyl group, trimethylsilylphenyl group, 9,9-dimethylfluorenyl group, 9,9-diphenylfluorenyl group, 9,9'-spirobifluorenyl group, cyanophenyl group and silylphenyl group are preferable.

The alkyl group(s) for $Ar_1$, $Ar_2$ and $Ar_3$ is preferably each independently an alkyl group having 1 to 10 carbon atoms, and more preferably an alkyl group having 1 to 5 carbon atoms. Examples of the alkyl group(s) for $Ar_1$ and $Ar_2$ include a methyl group, ethyl group, n-propyl group, isopropyl group, n-butyl group, isobutyl group, s-butyl group, t-butyl group, pentyl group (including isomers thereof), hexyl group (including isomers thereof), heptyl group (including isomers thereof), octyl group (including isomers thereof), nonyl group (including isomers thereof), decyl group (including isomers thereof), undecyl group (including isomers thereof) and dodecyl group (including isomers thereof), among which a methyl group, ethyl group, n-propyl group, isopropyl group, n-butyl group, isobutyl group, s-butyl group, t-butyl group and pentyl group (including isomers thereof) are preferable, a methyl group, ethyl group, n-propyl group, isopropyl group, n-butyl group, isobutyl group, s-butyl group and t-butyl group are more preferable, and a methyl group, ethyl group, isopropyl group and t-butyl group are especially preferable.

The alkyl group(s) for $Ar_1$, $Ar_2$ and $Ar_3$ may each independently be a cycloalkyl group having 3 to 50 ring carbon atoms. The cycloalkyl group(s) for $Ar_1$, $Ar_2$ and $Ar_3$ is preferably each independently a cycloalkyl group having 3 to 6 ring carbon atoms, and more preferably a cycloalkyl group having 5 or 6 ring carbon atoms. Examples of the cycloalkyl group(s) for $Ar_1$, $Ar_2$ and $Ar_3$ include a cyclopropyl group, cyclobutyl group, cyclopentyl group, cyclohexyl group, cycloheptyl group, cyclooctyl group and adamantyl group, among which a cyclopentyl group and cyclohexyl group are preferable.

The alkenyl group(s) for $Ar_1$, $Ar_2$ and $Ar_3$ is preferably each independently an alkenyl group having 2 to 20 carbon atoms, and more preferably an alkenyl group having 2 to 10 carbon atoms. Examples of the alkenyl group(s) for $Ar_1$, $Ar_2$ and $Ar_3$ include a vinyl group, allyl group, 1-butenyl group, 2-butenyl group, 3-butenyl group, 1,3-butanedienyl group, 1-methylvinyl group, 1-methylallyl group, 1,1-dimethylallyl group, 2-methylallyl group and 1,2-dimethylallyl group.

Examples of the substituted alkenyl group include a styryl group, 2,2-diphenylvinyl group, 1,2-diphenylvinyl group, 1-phenylallyl group, 2-phenylallyl group, 3-phenylallyl group, 3,3-diphenylallyl group, 1-phenyl-1-butenyl group and 3-phenyl-1-butenyl group.

The alkynyl group(s) for $Ar_1$, $Ar_2$ and $Ar_3$ is preferably each independently an alkynyl group having 2 to 20 carbon atoms, and more preferably an alkynyl group having 2 to 10 carbon atoms. The alkynyl group(s) for $Ar_1$, $Ar_2$ and $Ar_3$ may be a propargyl group or a 3-pentynyl group.

The heterocyclic group(s) for $Ar_1$, $Ar_2$ and $Ar_3$ is preferably each independently a heterocyclic group having 5 to 24 ring atoms, and more preferably a heterocyclic group having 5 to 18 ring atoms. The heterocyclic group(s) for $Ar_1$, $Ar_2$ and $Ar_3$ may be a heterocyclic group having 1 to 5 hetero atoms. Examples of the hetero atom include nitrogen atom, oxygen atom and sulfur atom. The heterocyclic group(s) for $Ar_1$, $Ar_2$ and $Ar_3$ may each independently be any one of a pyrrolyl group, furyl group, thienyl group, pyridyl group, pyridazynyl group, pyrimidinyl group, pyrazinyl group, triazinyl group, imidazolyl group, oxazolyl group, thiazolyl group, pyrazolyl group, isooxazolyl group, isothiazolyl group, oxadiazolyl group, thiadiazolyl group, triazolyl group, tetrazolyl group, indolyl group, isoindolyl group, benzofuranyl group, isobenzofuranyl group, benzothiophenyl group, isobenzothiophenyl group, indolizinyl group, quinolizinyl group, quinolyl group, isoquinolyl group, cinnoline group, phthalazinyl group, quinazolinyl group, quinoxalinyl group, benzimidazolyl group, benzoxazolyl group, benzothiazolyl group, indazolyl group, benzisoxazolyl group, benzisothiazolyl group, dibenzofuranyl group, dibenzothiophenyl group, carbazolyl group, phenanthridinyl group, acridinyl group, phenanthrolinyl group, phenazinyl group, phenothiazinyl group, phenoxazinyl group and xanthenyl group, among which a furyl group, thienyl group, pyridyl group, pyridazynyl group, pyrimidinyl group, pyrazinyl group, triazinyl group, benzofuranyl group, benzothiophenyl group, dibenzofuranyl group and dibenzothiophenyl group are preferable, and a benzofuranyl group, benzothiophenyl group, dibenzofuranyl group and dibenzothiophenyl group are more preferable.

Regarding the compound represented by the formula (10), an intended substituent meant by "substituted or unsubstituted" is preferably selected from the group consisting of an alkyl group having 1 to 50 (preferably 1 to 10, more preferably 1 to 5) carbon atoms, an alkenyl group having 2 to 20 (preferably 2 to 10) carbon atoms, an alkynyl group having 2 to 20 (preferably 2 to 10) carbon atoms, a cycloalkyl having 3 to 50 (preferably 3 to 6, more preferably 5 or 6) ring carbon atoms, an aromatic hydrocarbon group having 6 to 50 (preferably 6 to 24, more preferably 6 to 12) ring carbon atoms, an aralkyl group having 1 to 50 (preferably 1 to 10, more preferably 1 to 5) carbon atoms containing an aromatic hydrocarbon group having 6 to 50 (preferably 6 to 24, more preferably 6 to 12) ring carbon atoms, an amino group, a monoalkylamino or dialkylamino group having an alkyl group having 1 to 50 (preferably 1 to 10, more preferably 1 to 5) carbon atoms, a monoarylamino or diarylamino group having an aromatic hydrocarbon group having 6 to 50 (preferably 6 to 24, and more preferably 6 to 12) ring carbon atoms, an alkoxy group having an alkyl group having 1 to 50 (preferably 1 to 10, more preferably 1 to 5) carbon atoms, an aryloxy group having an aromatic hydrocarbon group having 6 to 50 (preferably 6 to 24, and more preferably 6 to 12) ring carbon atoms, an alkylthio group having an alkyl group having 1 to 50 (preferably 1 to 10, more preferably 1 to 5) carbon atoms, an arylthio group having an aromatic hydrocarbon group having 6 to 50 (preferably 6 to 24, and more preferably 6 to 12) ring carbon atoms, a monosubstituted, disubstituted or trisubstituted silyl group having a group selected from an alkyl group having 1 to 50 (preferably 1 to 10, more preferably 1 to 5) carbon atoms and an aromatic hydrocarbon group having 6 to 50 (preferably 6 to 24, more preferably 6 to 12) ring carbon atoms, a heterocyclic group having 5 to 50 (preferably 5 to 24, more preferably 5 to 18) ring atoms and 1 to 5 (preferably 1 to 3, more preferably 1 or 2) hetero atoms (e.g., a nitrogen atom, oxygen atom and sulfur atom), a haloalkyl group having 1 to 50 carbon atoms (preferably 1 to 10, and more preferably 1 to 5 carbon atoms), a halogen atom (e.g., a fluorine atom, chlorine atom, bromine atom or iodine atom, preferably a fluorine atom), a cyano group, and a nitro group.

Among the above substituents, a substituent selected from the group consisting of an alkyl group having 1 to 5 carbon atoms, cycloalkyl group having 5 or 6 carbon atoms, aromatic hydrocarbon group having 6 to 12 ring carbon atoms, and heterocyclic group having 5 to 24 ring atoms and 1 to 3 hetero atoms (at least one of a nitrogen atom, oxygen atom and sulfur atom) is particularly preferable.

The alkyl group having 1 to 50 carbon atoms meant by "substituted or unsubstituted" is the same as the alkyl group(s) for $Ar_1$, $Ar_2$ and $Ar_3$. The alkenyl group having 2 to 20 carbon atoms meant by "substituted or unsubstituted" is the same as the alkenyl group(s) for $Ar_1$, $Ar_2$ and $Ar_3$.

The alkynyl group having 2 to 20 carbon atoms meant by "substituted or unsubstituted" is the same as the alkynyl group(s) for $Ar_1$, $Ar_2$ and $Ar_3$.

The cycloalkyl group having 3 to 50 ring carbon atoms meant by "substituted or unsubstituted" is the same as the cycloalkyl group(s) for $Ar_1$, $Ar_2$ and $Ar_3$.

The aromatic hydrocarbon group having 6 to 50 ring carbon atoms meant by "substituted or unsubstituted" is the same as the aromatic hydrocarbon group(s) for $Ar_1$, $Ar_2$ and $Ar_3$.

When the substituent meant by "substituted or unsubstituted" is an aralkyl group having 6 to 50 ring carbon atoms, the aralkyl group contains an aromatic hydrocarbon group having 6 to 50 ring carbon atoms and an alkyl group having 1 to 50 carbon atoms, and respective specific examples of the alkyl group moiety and the aromatic hydrocarbon group moiety are the same as those of the above alkyl group and the above aromatic hydrocarbon group.

When the substituent meant by "substituted or unsubstituted" is the monoalkylamino or dialkylamino group, specific examples of the alkyl group moiety are the same as those of the above alkyl group.

When the substituent meant by "substituted or unsubstituted" is the monoarylamino or diarylamino group, specific examples of the aryl group (aromatic hydrocarbon group) moiety are the same as those of the above aromatic hydrocarbon group.

When the substituent meant by "substituted or unsubstituted" is the alkoxy group, specific examples of the alkyl group moiety are the same as those of the above alkyl group, and the alkoxy group is preferably, for instance, a methoxy group or an ethoxy group.

When the substituent meant by "substituted or unsubstituted" is the aryloxy group, specific examples of the aryl group (aromatic hydrocarbon group) moiety are the same as those of the above aromatic hydrocarbon group, and the aryloxy group may be a phenoxy group.

When the substituent meant by "substituted or unsubstituted" is the alkylthio group, specific examples of the alkyl group moiety are the same as those of the above alkyl group.

When the substituent meant by "substituted or unsubstituted" is the arylthio group, specific examples of the aryl group (aromatic hydrocarbon group) moiety are the same as those of the above aromatic hydrocarbon group.

When the substituent meant by "substituted or unsubstituted" is the monosubstituted, disubstituted or trisubstituted silyl group, the silyl group may be an alkylsilyl group having 1 to 50 carbon atoms or an arylsilyl group having 6 to 50 ring carbon atoms. Examples of the alkylsilyl group having 1 to 50 carbon atoms include a monoalkylsilyl group, dialkylsilyl group and trialkylsilyl group. Specific examples of each alkyl group in the alkylsilyl group having 1 to 50 carbon atoms are the same as those of the above alkyl group. Examples of the arylsilyl group having 6 to 50 ring carbon atoms include a monoarylsilyl group, diarylsilyl group and triarylsilyl group. Specific examples of each aryl group in the arylsilyl group having 6 to 50 ring carbon atoms, which are the same as those of the above aryl group, may include a trimethylsilyl group, triethylsilyl group, t-butyldimethylsilyl group, vinyldimethylsilyl group, propyldimethylsilyl group, isopropyldimethylsilyl group, triphenylsilyl group, phenyldimethylsilyl group, t-butyldiphenylsilyl group and tritolylsilyl group.

When the substituent meant by "substituted or unsubstituted" is the heterocyclic group, the heterocyclic group is the same as the hetrocyclic group(s) for $Ar_1$, $Ar_2$ and $Ar_3$.

When the substituent meant by "substituted or unsubstituted" is the haloalkyl group, the haloalkyl group may be a group obtained by halogenating the above alkyl group, specific examples of which include a trifluoromethyl group.

The first material of the exemplary embodiment may be a compound represented by a formula (12) below.

[Formula 10]

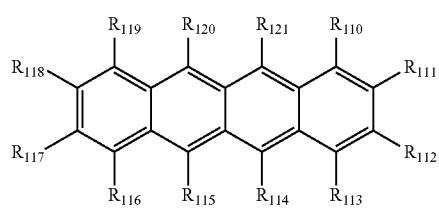

(12)

In the formula (12), $R_{110}$ to $R_{121}$ each independently represent a hydrogen atom or a substituent, the substituent being selected from the group consisting of a halogen atom, a cyano group, a substituted or unsubstituted alkyl group having 1 to 50 carbon atoms, a substituted or unsubstituted cycloalkyl group having 3 to 30 ring carbon atoms, a substituted or unsubstituted alkenyl group having 2 to 20 carbon atoms, a substituted or unsubstituted alkynyl group having 2 to 20 carbon atoms, a substituted or unsubstituted alkoxy group having 1 to 50 carbon atoms, a substituted or unsubstituted alkylthio group having 1 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted trialkylsilyl group, a substituted or unsubstituted arylalkylsilyl group, a substituted or unsubstituted triarylsilyl group, a substituted or unsubstituted diarylphosphine oxide group, an amino group, a monoalkylamino or dialkylamino group having a substituted or unsubstituted alkyl group having 1 to 50 carbon atoms, a substituted or unsubstituted aromatic hydrocarbon group having 6 to 30 ring carbon atoms, and a substituted or unsubstituted heterocyclic group having 5 to 30 ring atoms.

Second Material

In the exemplary embodiment, the second material is a delayed fluorescent material.

Delayed Fluorescence

Delayed fluorescence (thermally activated delayed fluorescence) is explained in "ADACHI, Chihaya, ed., *Yuki Hando-tai no Debaisu Bussei* (*Device Physics of Organic Semiconductors*), Kodansha, pp. 261-268." According to this literature, when an energy gap $\Delta E_{13}$ between the singlet state and the triplet state of a fluorescent material is reduced, inverse energy transfer from the triplet state, a low transition probability of which is usually low, to the singlet state occurs with a high efficiency to cause thermally activated delayed fluorescence (TADF). Further, FIG. 10.38 in this literature illustrates a mechanism for causing delayed fluorescence. The second material of the exemplary embodiment is a compound capable of thermally activated delayed fluorescence caused by this mechanism.

Occurrence of delayed fluorescence emission can be determined by transient PL measurement.

Figure 2:
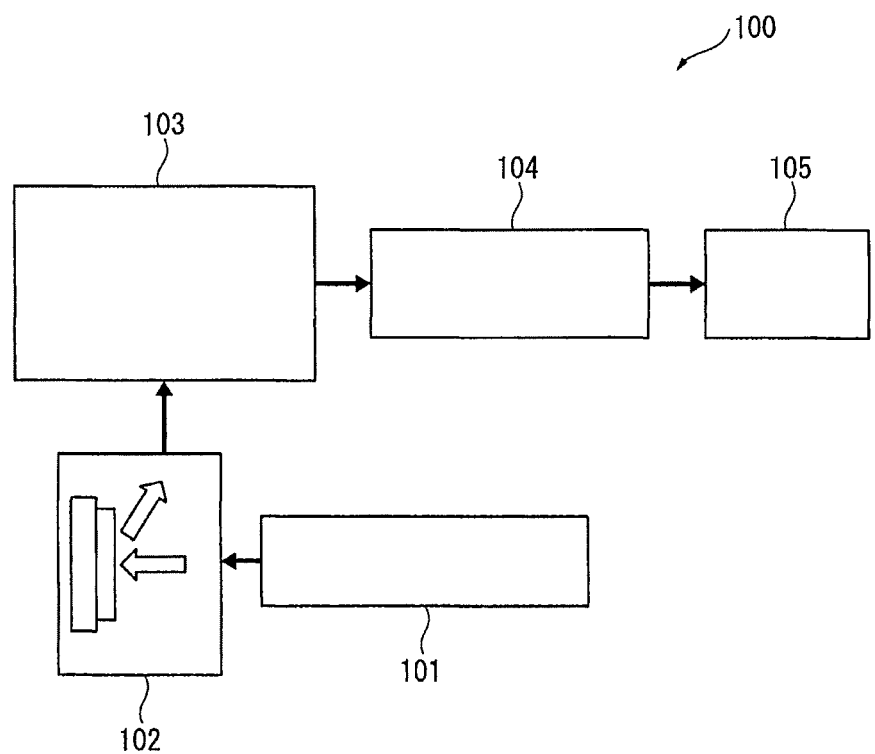
FIG. 2 schematically shows a device for measuring transient PL.

FIG. 2 schematically shows a device for measuring transient PL.

A transient PL measuring device 100 of the exemplary embodiment includes: a pulse laser 101 capable of emitting light with a predetermined wavelength; a sample chamber 102 for housing a measurement sample; a spectrometer 103 that disperses light emitted from the measurement sample; a streak camera 104 for forming a two-dimensional image; and a personal computer 105 that analyzes the two-dimensional image imported thereinto. It should be noted that transient PL may be measured by a device different from one described in the exemplary embodiment.

The sample to be housed in the sample chamber 102 is prepared by forming a thin film, which is made of a matrix material doped with a doping material at a concentration of 12 mass %, on a quartz substrate.

The thus-obtained thin film sample is housed in the sample chamber 102, and is irradiated with a pulse laser emitted from the pulse laser 101 to be excited. The emitted excitation light is taken in a 90-degree direction, and is dispersed by the spectrometer 103. A two-dimensional image of the light is formed through the streak camera 104. In the thus-obtained two-dimensional image, an ordinate axis corresponds to time, an abscissa axis corresponds to wavelength, and a bright spot corresponds to luminous intensity. The two-dimensional image is taken at a predetermined time axis, thereby obtaining an emission spectrum with an ordinate axis representing luminous intensity and an abscissa axis representing wavelength. Further, the two-dimensional image is taken at a wavelength axis, thereby obtaining a decay curve (transient PL) with an ordinate axis representing the logarithm of luminous intensity and an abscissa axis representing time.

For instance, a thin film sample A was prepared using a reference compound H1 below as a matrix material and a reference compound D1 below as a doping material, and transient PL was measured.

[Formula 11]

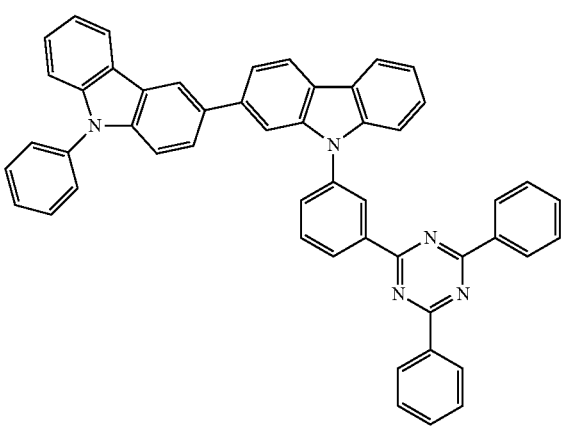

(Reference Compound H1)

(Compound D1)

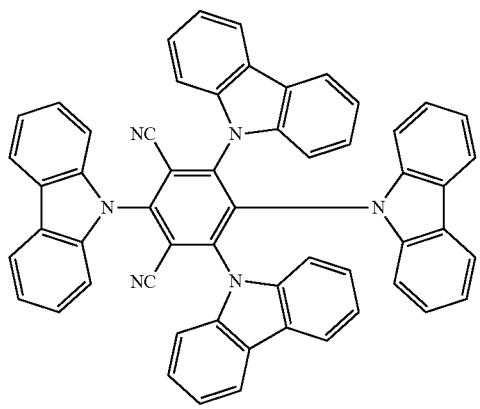

The behavior of delayed fluorescence can be analyzed based on the decay curve obtained by the transient PL measurement. The transient PL is a process where a sample is irradiated with a pulse laser to be excited, and a decay behavior (transient characteristics) of PL emission after the irradiation is measured. PL emission using a TADF material is divided into an emission component from singlet excitons generated by the first PL excitation and an emission component from singlet excitons generated via triplet excitons. The lifetime of the singlet excitons generated by the first PL excitation is in a nano-second order and considerably short. Emission from these singlet excitons thus decays immediately after the irradiation with the pulse laser.

In contrast, delayed fluorescence, which is emission from the singlet excitons generated via long-life triplet excitons, decays slowly. There is thus a large difference in time between emission from the singlet excitons generated by the first PL excitation and emission from the singlet excitons generated via triplet excitons. Therefore, a luminous intensity resulting from the delayed fluorescence can be obtained.

Respective decay curves of the thin film sample A and a thin film sample B were analyzed. The thin film sample B was prepared in the same manner as described above using a reference compound H2 below as a matrix material and the reference compound D1 as a doping material.

Figure 3:
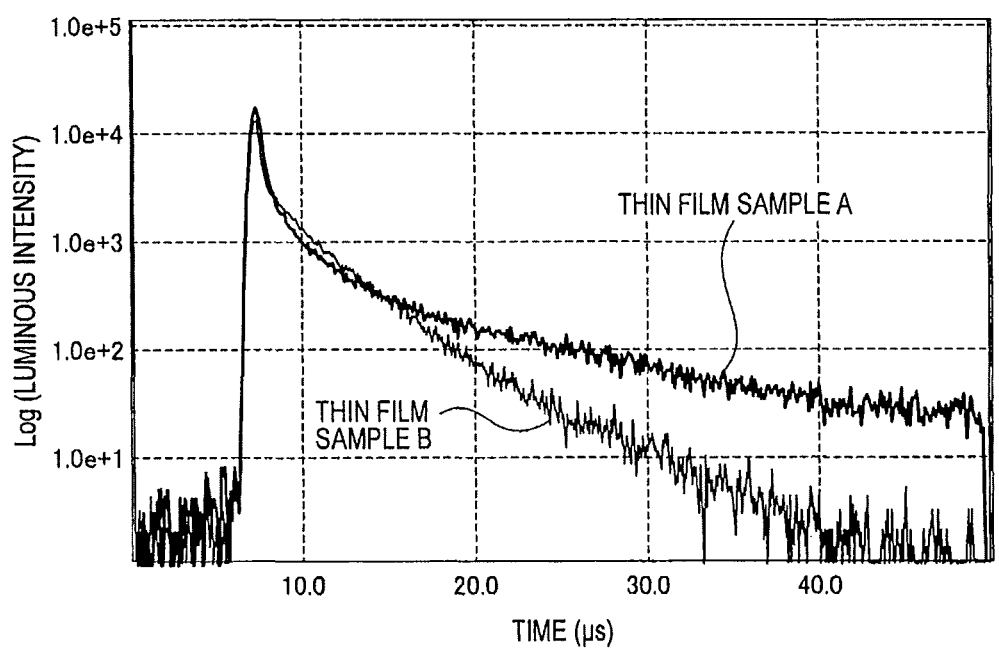
FIG. 3 shows examples of a transient PL decay curve.

FIG. 3 shows a decay curve obtained from transient PL measured using each of the thin film samples A and B.

[Formula 12]

(Reference Compound H2)

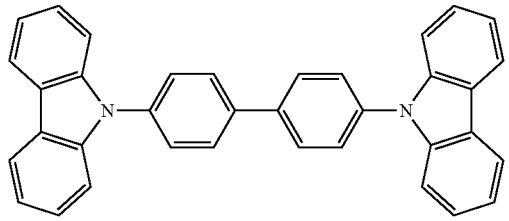

As described above, an emission decay curve with an ordinate axis representing luminous intensity and an abscissa axis representing time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

In the exemplary embodiment, the luminescence amount of the delayed fluorescence can be obtained using the device shown in FIG. 2. Emission from the second material includes Prompt emission and Delay emission. Prompt emission is observed immediately after the second material is brought into an excited state, in other words, after the second material is excited with a pulse beam (a beam emitted from a pulse laser) having a wavelength absorbable by the second material. Delay emission is observed not immediately after the excitation with the pulse beam but after a while. In the exemplary embodiment, the amount of Delay emission is 5% or more relative to the amount of the Prompt emission.

The amount of Prompt emission and the amount of Delay emission can be obtained in the same method as a method described in "Nature 492, 234-238, 2012 (Reference Literature 1)." The amount of Prompt emission and the amount of Delay emission may be calculated using a device different from one described in Reference Literature 1.

Further, for measurement of delayed fluorescence, a sample prepared by the following method is usable. For instance, a sample is prepared by co-depositing a compound TH-2 (described later) as the second material on a quartz substrate so that the second material accounts for 12 mass % of the deposition to form a 100-nm-thick thin film.

[Formula 13]

TH-2

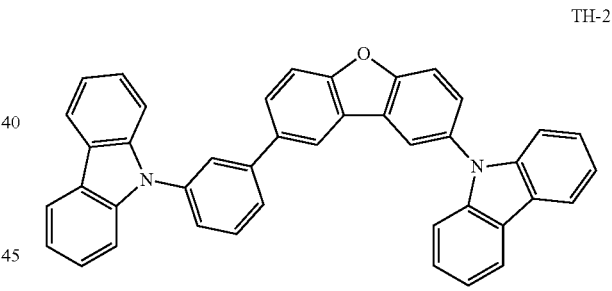

In the exemplary embodiment, the second material preferably has a moiety represented by a formula (2) below and a moiety represented by a formula (2Y) below in one molecule.

[Formula 14]

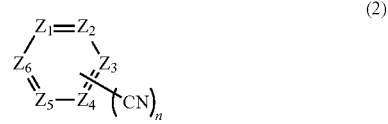

(2)

In the formula (2), CN is a cyano group.

n is an integer of 1 or more. n is preferably an integer of 1 to 5, and more preferably 2 to 4.

$Z_1$ to $Z_6$ each independently represent a nitrogen atom, a carbon atom bonded to CN, or a carbon atom bonded to another atom in the molecule of the second material. For instance, when $Z_1$ is a carbon atom bonded to CN, at least one of the other five ($Z_2$ to $Z_6$) should be a carbon atom bonded to another atom in the molecule of the second material. The another atom may be an atom in the moiety represented by the formula (2Y), or may be an atom in a linking group or a substituent between the moieties.

The second material of the exemplary embodiment may contain a six-membered ring including $Z_1$ to $Z_6$ as the moiety, or may contain a fused ring including the six-membered ring further fused with a ring as the moiety.

[Formula 15]

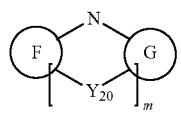

(2Y)

In the formula (2Y), F and G each independently represent a cyclic structure.

m is 0 or 1.

When m is 1, $Y_{20}$ is a single bond, oxygen atom, sulfur atom, selenium atom, carbon atom, silicon atom or germanium atom.

When m is 0 in the formula (2Y), the formula (2Y) is represented by a formula (20Y) below.

[Formula 16]

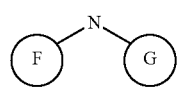

(20Y)

In the formula (20Y), a cyclic structure F and a cyclic structure G are respectively the same as the cyclic structure F and the cyclic structure G in the formula (2Y).

When m is 1 in the formula (2Y), the formula (2Y) is represented by any one of formulae (22) to (28) below.

[Formula 17]

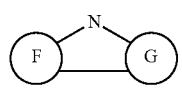 (22)

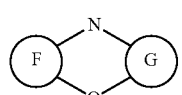 (23)

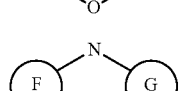 (24)

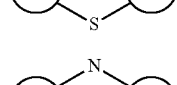 (25)

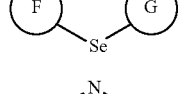 (26)

-continued

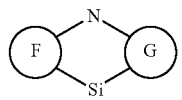 (27)

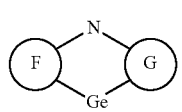 (28)

In each of the formulae (22) to (28), a cyclic structure F and a cyclic structure G are respectively the same as the cyclic structure F and the cyclic structure G in the formula (2Y).

In the exemplary embodiment, the cyclic structure F and the cyclic structure G are each preferably a five- or six-membered ring, which is preferably an unsaturated ring, and more preferably an unsaturated six-membered ring.

The second material of the exemplary embodiment is preferably a compound represented by a formula (20) below.

[Formula 18]

 (20)

In the formula (20), A is represented by the formula (2), in which: CN is a cyano group; n is an integer of 1 or more; $Z_1$ to $Z_6$ each independently represent a nitrogen atom, a carbon atom bonded to CN, a carbon atom bonded to R, a carbon atom bonded to L, or a carbon atom bonded to D; at least one of $Z_1$ to $Z_6$ is the carbon atom bonded to CN and at least another one thereof is the carbon atom bonded to L or D; R each independently represent a hydrogen atom or a substituent, the substituent being selected from the group consisting of a halogen atom, substituted or unsubstituted aryl group having 6 to 30 ring carbon atoms, substituted or unsubstituted aromatic heterocyclic group having 5 to 30 ring atoms, substituted or unsubstituted alkyl group having 1 to 30 carbon atoms, substituted or unsubstituted alkylsilyl group having 3 to 30 carbon atoms, substituted or unsubstituted arylsilyl group having 6 to 60 ring carbon atoms, substituted or unsubstituted alkoxy group having 1 to 30 carbon atoms, substituted or unsubstituted aryloxy group having 6 to 30 ring carbon atoms, substituted or unsubstituted alkylamino group having 2 to 30 carbon atoms, substituted or unsubstituted arylamino group having 6 to 60 ring carbon atoms, substituted or unsubstituted alkylthio group having 1 to 30 carbon atoms, and substituted or unsubstituted arylthio group having 6 to 30 ring carbon atoms.

In the formula (20), D is represented by the formula (2Y), in which: the cyclic structure F and the cyclic structure G may be substituted or unsubstituted; m is 0 or 1; and when m is 1, $Y_{20}$ is a single bond, oxygen atom, sulfur atom, selenium atom, carbonyl group, $CR_{21}R_{22}$, $SiR_{23}R_{24}$ or $GeR_{25}R_{26}$, and $R_{21}$ to $R_{26}$ are each the same as the groups listed for R. When m is 1 in the formula (2Y), the formula (2Y) is represented by any one of the formulae (22) to (25) and formulae (21Y) to (24Y) below.

[Formula 19]

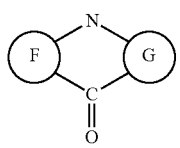 (21Y)

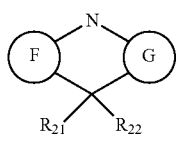 (22Y)

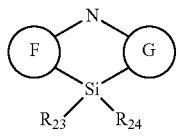 (23Y)

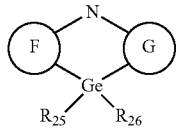 (24Y)

In the formula (20), (i) when L is interposed between A and D, L is a single bond, a substituted or unsubstituted aromatic hydrocarbon group having 6 to 14 ring carbon atoms, a substituted or unsubstituted aromatic heterocyclic group having 5 to 14 ring atoms, $CR_{81}R_{82}$, $NR_{83}$, O, S, $SiR_{84}R_{85}$, $CR_{86}R_{87}$-$CR_{88}R_{89}$, $CR_{90}$=$CR_{91}$, a substituted or unsubstituted aliphatic hydrocarbon ring group, or a substituted or unsubstituted aliphatic heterocyclic group, and $R_{81}$ to $R_{91}$ each independently represent the same as R described above.

In the formula (20), (ii) when L is present at a terminal end in the molecule of the second material, L represents the same as R described above.

In the formula (20), f is an integer of 1 or more, e and g are each independently an integer of 0 or more, a plurality of A may be mutually the same or different, a plurality of D may be mutually the same or different, and a plurality of L may be mutually the same or different.

The formula (20) is represented by, for instance, formulae (201) to (220) below.

TABLE 1

| Formula No. | e, f and g in Formula (20) | Formula |
|---|---|---|
| (201) | e = 0, f = 1, g = 0 | A-L-D |
| (202) | e = 0, f = 1, g = 0 | A-D |
| (203) | e = 0, f = 1, g = 1 | A-L-D-L-A |
| (204) | e = 0, f = 1, g = 1 | A-D-A |
| (205) | e = 1, f = 1, g = 0 | D-L-A-L-D |
| (206) | e = 1, f = 1, g = 0 | D-A-D |

TABLE 2

| Formula No. | e, f and g in Formula (20) | Formula |
|---|---|---|
| (207) | e = 1, f = 1, g = 1 | D-L-A-L-D-L-A |
| (208) | e = 1, f = 1, g = 1 | D-A-D-A |
| (209) | e = 1, f = 2, g = 0 | D-L-A-L-D-L-A-L-D |

TABLE 2-continued

| Formula No. | e, f and g in Formula (20) | Formula |
|---|---|---|
| (210) | e = 1, f = 2, g = 0 | D-A-D-A-D |
| (211) | e = 0, f = 2, g = 1 | A-L-D-L-A-L-D-L-A |
| (212) | e = 0, f = 2, g = 1 | A-D-A-D-A |

TABLE 3

| Formula No. | e, f and g in Formula (20) | Formula |
|---|---|---|
| (213) | e = 2, f = 1, g = 0 | D—L—A—L—D<br>               |<br>               L<br>               |<br>               D |
| (214) | e = 2, f = 1, g = 0 | D—A—D<br>     |<br>     D |
| (215) | e = 3, f = 1, g = 0 | D<br>|<br>L<br>|<br>D—L—A—L—D<br>       |<br>       L<br>       |<br>       D |
| (216) | e = 3, f = 1, g = 0 | D<br>|<br>D—A—D<br>    |<br>    D |

TABLE 4

| Formula No. | e, f and g in Formula (20) | Formula |
|---|---|---|
| (217) | e = 0, f = 1, g = 2 | A—L—D—L—A<br>       |<br>       L<br>       |<br>       A |
| (218) | e = 0, f = 1, g = 2 | A—D—A<br>    |<br>    A |
| (219) | e = 0, f = 1, g = 3 | A<br>|<br>L<br>|<br>A—L—D—L—A<br>       |<br>       L<br>       |<br>       A |
| (220) | e = 0, f = 1, g = 3 | A<br>|<br>A—D—A<br>    |<br>    A |

In a bracketed repeating unit attached with a repeating unit number f in the formula (20), D may be bonded to A via L, or A may be bonded to A via L. For instance, the second material may have a branched structure as represented by formulae (221) to (228) below.

[Formula 20]

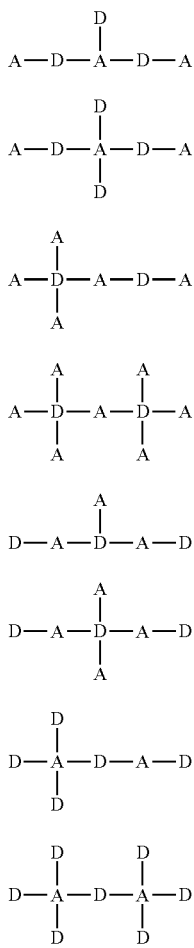

(221)
(222)
(223)
(224)
(225)
(226)
(227)
(228)

The second material of the exemplary embodiment is not limited to the compounds represented by the formulae (201) to (228). It should be noted that when L is omitted in the formulae (201) to (228), L is a single bond between A and D, or a hydrogen atom present at a terminal end in the molecule of the second material.

In order to keep ΔST of one molecule small, L is preferably not a fused aromatic ring in terms of molecular design, but L may be a fused aromatic ring as long as thermally activated delayed fluorescence is achieved. Further, since a molecular design where A and D are accurately situated in one molecule is required, the second material of the exemplary embodiment is preferably a low-molecule material. Specifically, the second material of the exemplary embodiment has a molecular weight of 5000 or less, and more preferably 3000 or less. The second material of the exemplary embodiment preferably has the moieties of the formulae (2) and (2Y).

The organic EL device containing the second material emits light using the thermally activated delayed fluorescence mechanism.

In the exemplary embodiment, the formula (2Y) is preferably represented by at least one of formulae (2a) and (2x) below.

[Formula 21]

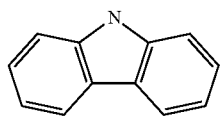

(2a)

[Formula 22]

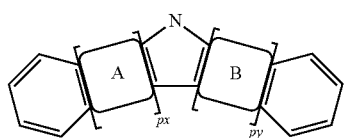

(2x)

In the formula (2x), A and B each independently represent a cyclic structure represented by a formula (2c) below or a cyclic structure represented by a formula (2d) below. Each of the cyclic structure A and the cyclic structure B is fused to an adjacent cyclic structure at any position. px and py are each independently an integer of 0 to 4 and respectively represent the number of the cyclic structure A and the number of the cyclic structure B. When px is an integer of 2 to 4, a plurality of cyclic structures A may be mutually the same or different. When py is an integer of 2 to 4, a plurality of cyclic structures B may be mutually the same or different. Accordingly, for instance, when px is 2, the cyclic structures A may be either two cyclic structures represented by the formula (2c) or two cyclic structures represented by the formula (2d), or may alternatively be a combination of one cyclic structure represented by the formula (2c) and one cyclic structure represented by the formula (2d).

[Formula 23]

(2c)

[Formula 24]

(2d)

In the formula (2d), $Z_7$ is a carbon atom, nitrogen atom, sulfur atom or oxygen atom.

When px is 0 and py is an integer of c in the formula (2x), the formula (2x) is represented by a formula (2b) below.

[Formula 25]

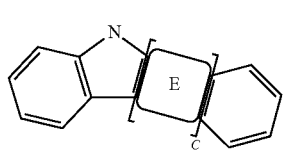

(2b)

In the formula (2b), c is an integer of 1 to 4. When c is an integer of 2 to 4, a plurality of cyclic structures E may be mutually the same or different. In the formula (2b), E represents a cyclic structure represented by the formula (2c) or a cyclic structure represented by the formula (2d). The cyclic structure E is fused to an adjacent cyclic structure at any position. Accordingly, for instance, when c is 2, the two cyclic structures E may be either two cyclic structures represented by the formula (2c) or two cyclic structures represented by the formula (2d) or may alternatively be a combination of one cyclic structure represented by the formula (2c) and one cyclic structure represented by the formula (2d).

When the moieties of the formula (2) and the formula (2Y) are simultaneously present in one molecule, the molecule can be effectively designed to have a small ΔST.

The second material of the exemplary embodiment preferably has a structure represented by a formula (2e) below in the molecule.

[Formula 26]

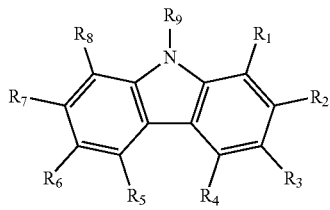

(2e)

In the formula (2e), $R_1$ to $R_9$ each independently represent a hydrogen atom, a substituent, or a single bond bonded to another atom in the molecule of the second material, the substituent being selected from the group consisting of a halogen atom, substituted or unsubstituted aryl group having 6 to 30 ring carbon atoms, substituted or unsubstituted aromatic heterocyclic group having 5 to 30 ring atoms, substituted or unsubstituted alkyl group having 1 to 30 carbon atoms, substituted or unsubstituted alkylsilyl group having 3 to 30 carbon atoms, substituted or unsubstituted arylsilyl group having 6 to 60 ring carbon atoms, substituted or unsubstituted alkoxy group having 1 to 30 carbon atoms, substituted or unsubstituted aryloxy group having 6 to 30 ring carbon atoms, substituted or unsubstituted alkylamino group having 2 to 30 carbon atoms, substituted or unsubstituted arylamino group having 6 to 60 ring carbon atoms, substituted or unsubstituted alkylthio group having 1 to 30 carbon atoms, and substituted or unsubstituted arylthio group having 6 to 30 ring carbon atoms. It should be noted that at least one of $R_1$ to $R_9$ is a single bond bonded to another atom in the molecule of the second material.

In the formula (2e), at least one of combinations of substituents selected from $R_1$ to $R_9$ may be mutually bonded to form a cyclic structure, In other words, in the formula (2e) where $R_1$ to $R_8$ are individually bonded to carbon atoms of the six-membered ring and $R_9$ is bonded to a nitrogen atom of the five-membered ring, a cyclic structure may be formed by adjacent substituents selected from $R_1$ to $R_8$ bonded to adjacent carbon atoms and $R_9$ bonded to the nitrogen atom of the five-membered ring. Specifically, in the formula (2e), at least one of combinations of substituents, namely, a combination of $R_1$ and $R_2$, a combination of $R_2$ and $R_3$, a combination of $R_3$ and $R_4$, a combination of $R_4$ and $R_5$, a combination of $R_5$ and $R_6$, a combination of $R_6$ and $R_7$, a combination of $R_7$ and $R_8$, a combination of $R_8$ and $R_9$, and a combination of $R_1$ and $R_9$, may be mutually bonded to form a cyclic structure.

In the exemplary embodiment, the cyclic structure formed by bonding the substituents is preferably a fused ring. For instance, in the formula (2e), the thus-formed cyclic structure may be a fused six-membered cyclic structure.

The second material of the exemplary embodiment preferably has a structure represented by a formula (2y) below in the molecule.

[Formula 27]

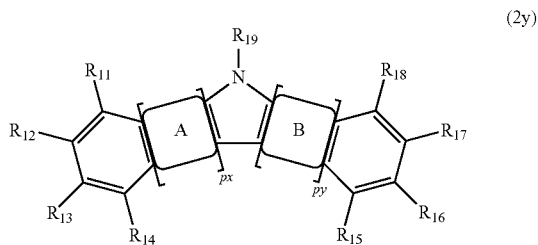

(2y)

$R_{11}$ to $R_{19}$ in the formula (2y) each independently represent the same as $R_1$ to $R_9$ in the formula (2e). It should be noted that at least one of $R_{11}$ to $R_{19}$ is a single bond bonded to another atom in the molecule of the second material. In the formula (2y), at least one of combinations of substituents selected from $R_{11}$ to $R_{19}$ may be mutually bonded to form a cyclic structure. In the formula (2y), A and B each independently represent a cyclic structure represented by a formula (2g) below or a cyclic structure represented by a formula (2h) below. Each of the cyclic structure A and the cyclic structure B is fused to an adjacent cyclic structure at any position. px, which represents the number of the cyclic structure(s) A, is an integer of 0 to 4. When px is an integer of 2 to 4, a plurality of cyclic structures A may be mutually the same or different. When py is an integer of 2 to 4, a plurality of cyclic structures B may be mutually the same or different. py, which represents the number of the cyclic structure(s) B, is an integer of 0 to 4. Accordingly, for instance, when px is 2, the two cyclic structures A may be either two cyclic structures represented by the formula (2g) or two cyclic structures represented by the formula (2h), or may alternatively be a combination of one cyclic structure represented by the formula (2g) and one cyclic structure represented by the formula (2h).

[Formula 28]

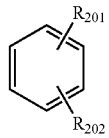

(2g)

[Formula 29]

(2h)

In the formula (2g), $R_{201}$ and $R_{202}$ each independently represent the same as $R_1$ to $R_9$ described above and may be mutually bonded to form a cyclic structure. $R_{201}$ and $R_{202}$ are individually bonded to carbon atoms forming the six-membered ring of the formula (2g).

In the formula (2h), $Z_8$ represents $CR_{203}R_{204}$, $NR_{205}$, a sulfur atom, or an oxygen atom, and $R_{202}$ to $R_{205}$ each independently represent the same as the substituents for $R_1$ to $R_9$ described above.

In the formula (2y), at least one of combinations of substituents selected from $R_{11}$ to $R_{19}$ and $R_{201}$ to $R_{205}$ may be mutually bonded to form a cyclic structure.

When px is 0 and py is an integer of c in the formula (2y), the formula (2y) is represented by a formula (2f) below.

[Formula 30]

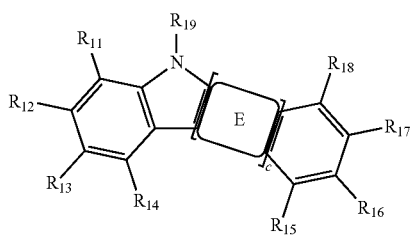

(2f)

$R_{11}$ to $R_{19}$ in the formula (2f) each independently represent the same as $R_1$ to $R_9$ in the formula (2e). It should be noted that at least one of $R_{11}$ to $R_{19}$ is a single bond bonded to another atom in the molecule of the second material. In the formula (2f), at least one of combinations of substituents selected from $R_{11}$ to $R_{19}$ may be mutually bonded to form a cyclic structure. In the formula (2f), E represents a cyclic structure represented by the formula (2g) or a cyclic structure represented by the formula (2h). The cyclic structure E is fused to an adjacent cyclic structure at any position. c, which represents the number of the cyclic structure(s) E, is an integer of 1 to 4. When c is an integer of 2 to 4, a plurality of cyclic structures E may be mutually the same or different. Accordingly, for instance, when c is 2, the two cyclic structures E may be either two cyclic structures represented by the formula (2g) or two cyclic structures represented by the formula (2h), or may alternatively be a combination of one cyclic structure represented by the formula (2g) and one cyclic structure represented by the formula (2h).

The second material of the exemplary embodiment is preferably represented by a formula (2A) below.

[Formula 31]

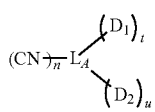

(2A)

In the formula (2A), n is an integer of 1 or more, t is an integer of 1 or more, and u is an integer of 0 or more. $L_A$ is a substituted or unsubstituted aromatic hydrocarbon ring having 6 to 30 ring carbon atoms or aromatic heterocycle having 6 to 30 ring atoms. CN is a cyano group. $D_1$ and $D_2$ are each independently represented by the formula (2Y), in which: the cyclic structure F and the cyclic structure G may be substituted or unsubstituted; m is 0 or 1; and when m is 1, $Y_{20}$ is a single bond, oxygen atom, sulfur atom, selenium atom, carbonyl group, $CR_{21}R_{22}$, $SiR_{23}R_{24}$ or $GeR_{25}R_{26}$, and $R_{21}$ to $R_{26}$ are each the same as R described above. When m is 1, the formula (2Y) is represented by any one of the formulae (22) to (25) and the formulae (21Y) to (24Y). $D_1$ and $D_2$ may be mutually the same or different. When t is 2 or more, a plurality of $D_1$ may be mutually the same or different. When u is 2 or more, a plurality of $D_2$ may be mutually the same or different.

In the exemplary embodiment, $L_A$ is preferably a substituted or unsubstituted aromatic hydrocarbon ring having 6 to 14 ring carbon atoms. Examples of the aromatic hydrocarbon ring having 6 to 14 ring carbon atoms include benzene, naphthalene, fluorene and phenanthrene. $L_A$ is further preferably an aromatic hydrocarbon ring having 6 to 10 ring carbon atoms.

Examples of the aromatic heterocycle having 6 to 30 ring atoms for $L_A$ include pyridine, pyrimidine, pyrazine, quinoline, quinazoline, phenanthroline, benzofuran and dibenzofuran.

In the exemplary embodiment, in the formula (2A), $D_1$ or $D_2$ may be bonded to a first one of the carbon atoms forming the aromatic hydrocarbon ring represented by $L_A$, and CN may be bonded to a second one adjacent to the first one. For instance, in the second material of the exemplary embodiment, D may be bonded to a first carbon atom $C_1$, and a cyano group may be bonded to a second carbon atom $C_2$ adjacent to the first carbon atom $C_1$ as shown in a moiety represented by a formula (2B) below. D in the formula (2B) represents the same as $D_1$ or $D_2$. In the formula (2B), a wavy line(s) shows a bonding position with another structure or an atom.

[Formula 32]

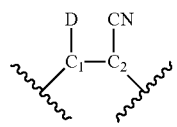

(2B)

When $D_1$ or $D_2$ having a structure represented by the formula (2a) or (2b) and the cyano group are adjacently bonded to the aromatic hydrocarbon ring represented by $L_A$, a value of ΔST of the compound can be reduced.

In the exemplary embodiment, t is preferably an integer of 2 or more. When 2 or more $D_1$ are bonded to the aromatic hydrocarbon ring represented by $L_A$, a plurality of $D_1$ may be the same or different in structure.

The second material of the exemplary embodiment is preferably represented by a formula (21) below.

[Formula 33]

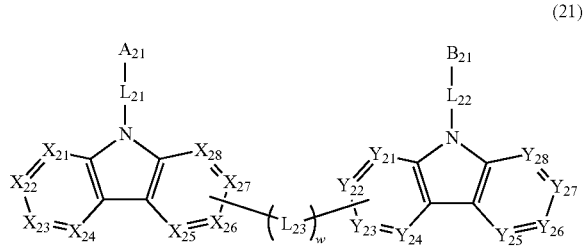

(21)

In the formula (21), $A_{21}$ and $B_{21}$ each independently represent a substituted or unsubstituted aromatic hydrocarbon group having 6 to 30 ring carbon atoms or a substituted or unsubstituted aromatic heterocyclic having 5 to 30 ring atoms.

$X_{21}$ to $X_{28}$ and $Y_{21}$ to $Y_{28}$ each independently represent a nitrogen atom, a carbon atom bonded to $R^D$, or a carbon atom bonded to $L_{23}$. It should be noted that at least one of $X_{25}$ to $X_{28}$ is a carbon atom bonded to $L_{23}$, and at least one of $Y_{21}$ to $Y_{24}$ is a carbon atom bonded to $L_{23}$.

$R^D$ each independently represent a hydrogen atom or a substituent, the substituent being selected from the group consisting of a halogen atom, substituted or unsubstituted aromatic hydrocarbon group having 6 to 30 ring carbon atoms, substituted or unsubstituted aromatic heterocyclic group having 5 to 30 ring atoms, substituted or unsubstituted alkyl group having 1 to 30 carbon atoms, and substituted or unsubstituted silyl group.

$L_{21}$ and $L_{22}$ each independently represent a single bond or a linking group. The linking group for $L_{21}$ and $L_{22}$ is any one of a substituted or unsubstituted aromatic hydrocarbon group having 6 to 30 ring carbon atoms, substituted or unsubstituted heterocyclic group having 5 to 30 ring atoms, multiple linking group including 2 to 4 groups selected from the above aromatic hydrocarbon groups, multiple linking group including bonded 2 to 4 groups selected from the above heterocyclic groups, and multiple linking group including bonded 2 to 4 groups selected from the above aromatic hydrocarbon groups and heterocyclic groups.

$L_{23}$ represents a substituted or unsubstituted monocyclic hydrocarbon group having 6 or less ring carbon atoms or a substituted or unsubstituted monocyclic heterocyclic group having 6 or less ring atoms.

w is an integer of 0 to 3. When w is 0, at least one of $X_2$ to $X_{28}$ and at least one of $Y_{21}$ to $Y_{24}$ are directly bonded.

It should be noted that the monocyclic hydrocarbon group is not a fused ring but a group derived from a single hydrocarbon ring (aliphatic cyclic hydrocarbon or aromatic hydrocarbon), and the monocyclic heterocyclic group is a group derived from a single heterocycle.

Further, the formula (21) satisfies at least one of the following conditions (i) and (ii): (i) at least one of $A_{21}$ and $B_{21}$ is a cyano-substituted aromatic hydrocarbon group having 6 to 30 ring carbon atoms or a cyano-substituted aromatic heterocyclic group having 6 to 30 ring atoms; and (i) at least one of $X_{21}$ to $X_{24}$ and $Y_{25}$ to $Y_{28}$ is a carbon atom bonded to $R^D$, and at least one of $R^D$ is a cyano-substituted aromatic hydrocarbon group having 6 to 30 ring carbon atoms or a cyano-substituted aromatic heterocyclic group having 6 to 30 ring atoms.

It should be noted that a plurality of $R^D$ may be mutually the same or different.

In the formula (21), when the aromatic hydrocarbon group having 6 to 30 ring carbon atoms or the aromatic heterocyclic group having 6 to 30 ring atoms represented by $A_{21}$ and $B_{21}$ is substituted, the substituent is preferably at least one group selected from the group consisting of a cyano group, halogen atom, alkyl group having 1 to 20 carbon atoms, cycloalkyl group having 3 to 20 carbon atoms, alkoxy group having 1 to 20 carbon atoms, haloalkyl group having 1 to 20 carbon atoms, haloalkoxy group having 1 to 20 carbon atoms, alkylsilyl group having 1 to 10 carbon atoms, aryl group having 6 to 30 ring carbon atoms, aryloxy group having 6 to 30 ring carbon atoms, aralkyl group having 6 to 30 carbon atoms, and heterocyclic group having 5 to 30 ring atoms. When $A_{21}$ and $B_{21}$ have a plurality of substituents, the substituents may be mutually the same or different.

The formula (21) preferably satisfies the condition (i) but not the condition (ii).

Alternatively, the formula (21) preferably satisfies the condition (ii) but not the condition (i).

Further, the formula (21) preferably satisfies the conditions (i) and (ii).

In the formula (21), at least one of $A_{21}$ and $B_{21}$ is preferably any one of a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, and a cyano-substituted triphenylenyl group.

In the formula (21), at least one of $X_{21}$ to $X_{24}$ and $Y_{25}$ to $Y_{28}$ is $CR^D$, and at least one of $R^D$ for $X_{21}$ to $X_{24}$ and $Y_{25}$ to $Y_{28}$ is preferably any one of a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, and a cyano-substituted triphenylenyl group.

In the formula (21), $X_{26}$ and $Y_{23}$ are preferably bonded to each other via $L_{23}$ or directly bonded to each other.

In the formula (21), $X_{26}$ and $Y_{22}$ are preferably bonded to each other via $L_{23}$ or directly bonded to each other.

In the formula (21), $X_{27}$ and $Y_{23}$ are preferably bonded to each other via $L_{23}$ or directly bonded to each other.

In the general formula (21), w is preferably 0.

Alternatively, in the general formula (21), w is preferably 1.

In the formula (21), $L_{21}$ and $L_{22}$ each represent a single bond or a substituted or unsubstituted aromatic hydrocarbon group having 6 to 30 ring carbon atoms.

Specific examples of the second material of the exemplary embodiment are shown below. It should be noted that the second material according to the invention may be different from these specific examples.

[Formula 34]

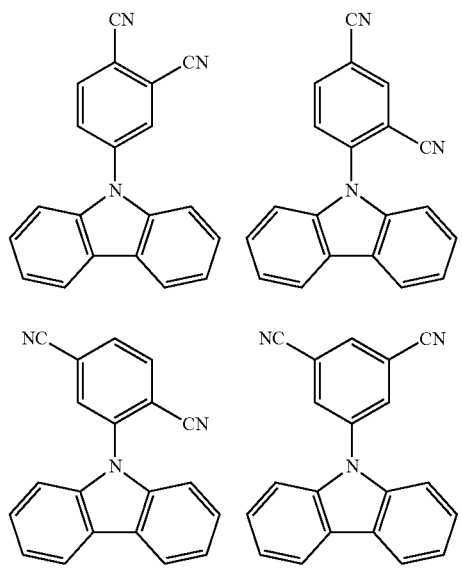

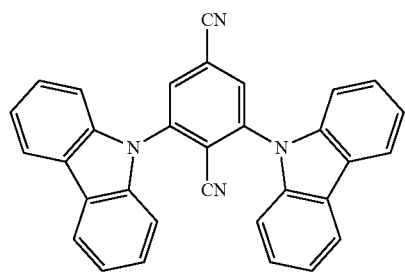
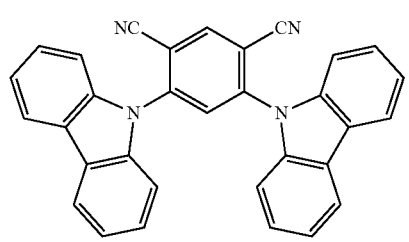
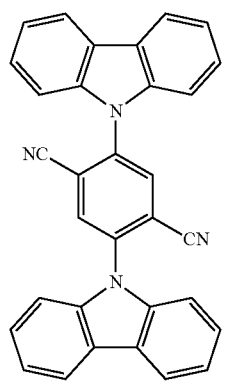
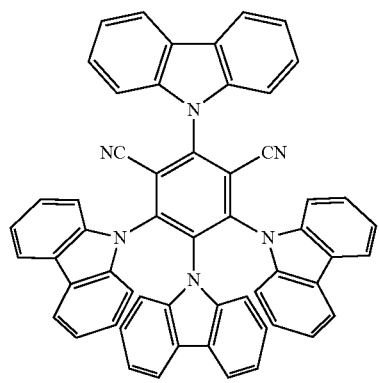
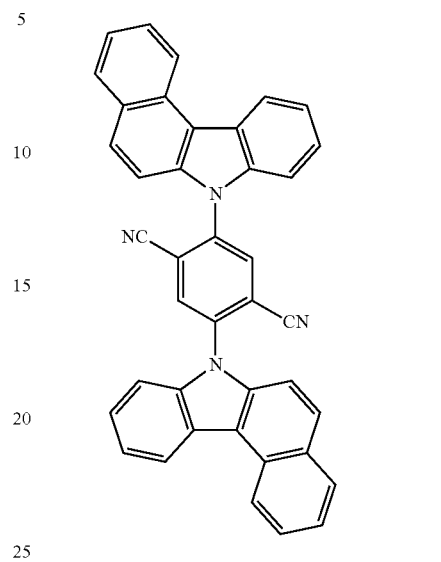
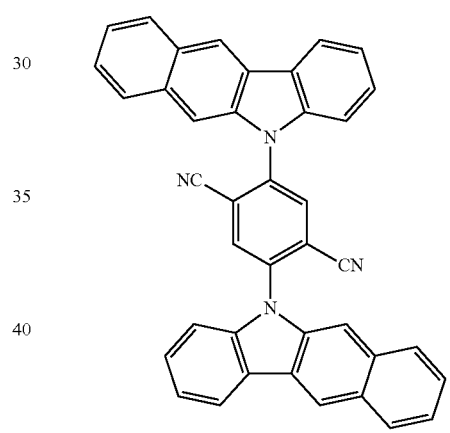
[Formula 35]
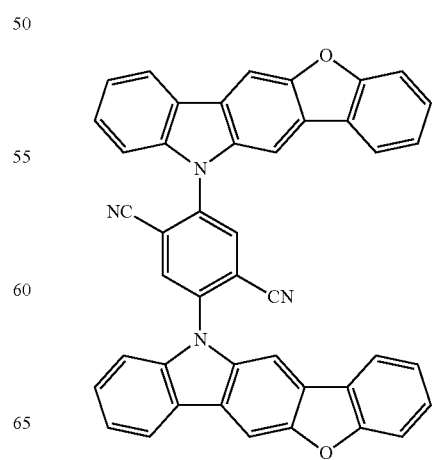
[Formula 36]

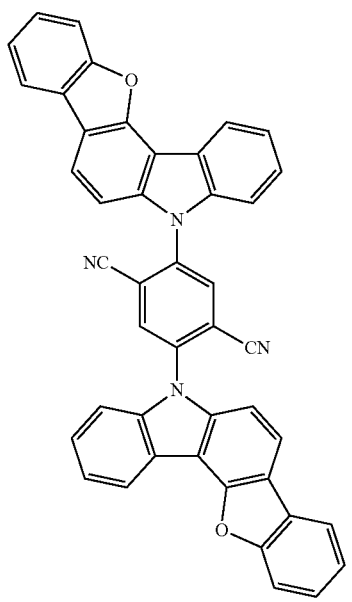
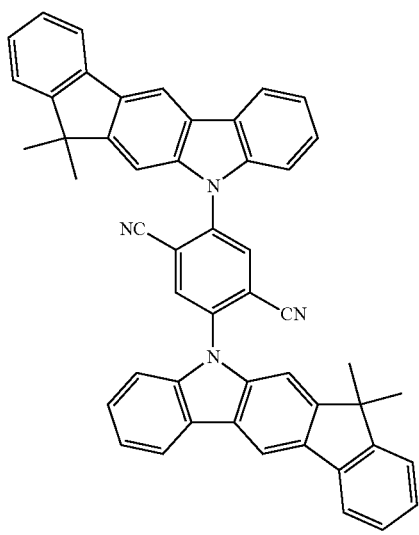
[Formula 37]
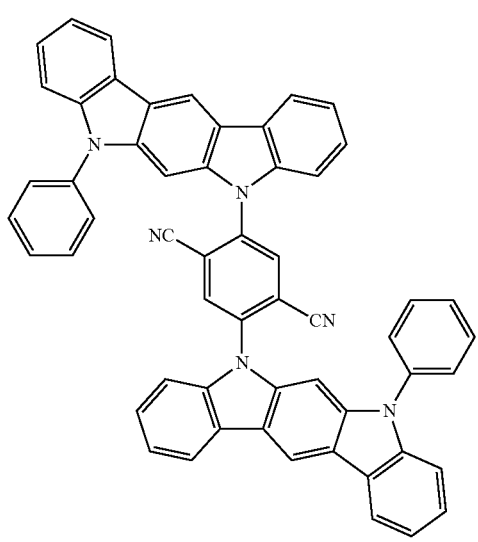
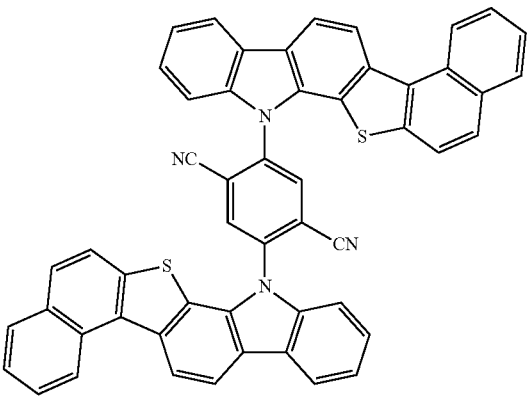
[Formula 38]
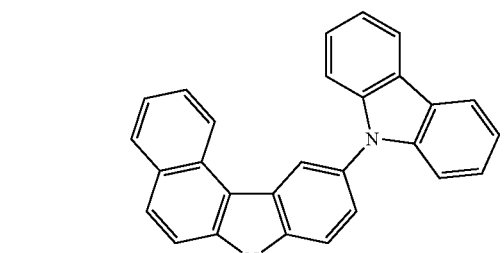
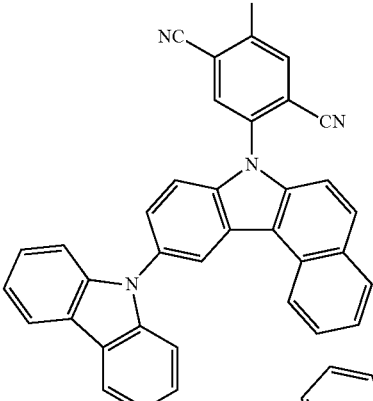
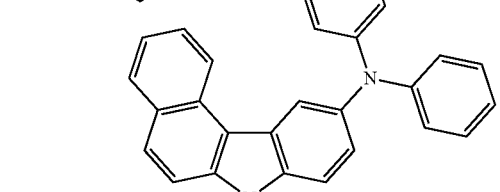
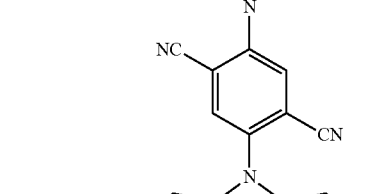
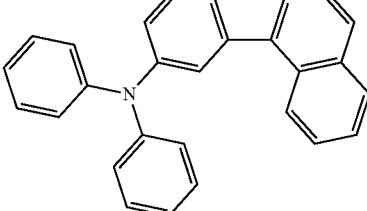

[Formula 39]
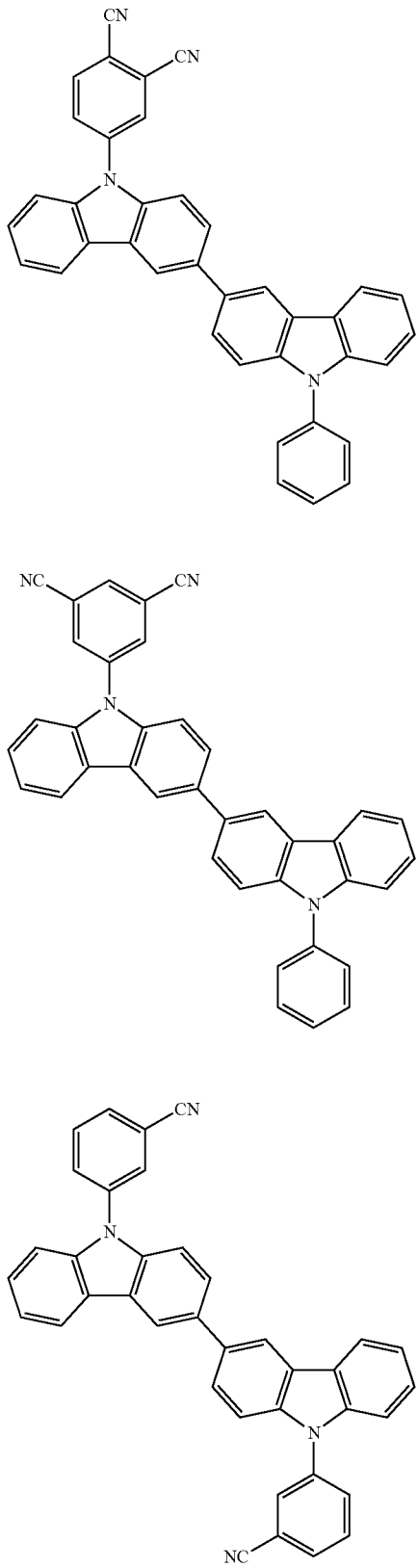
[Formula 40]
[Formula 41]
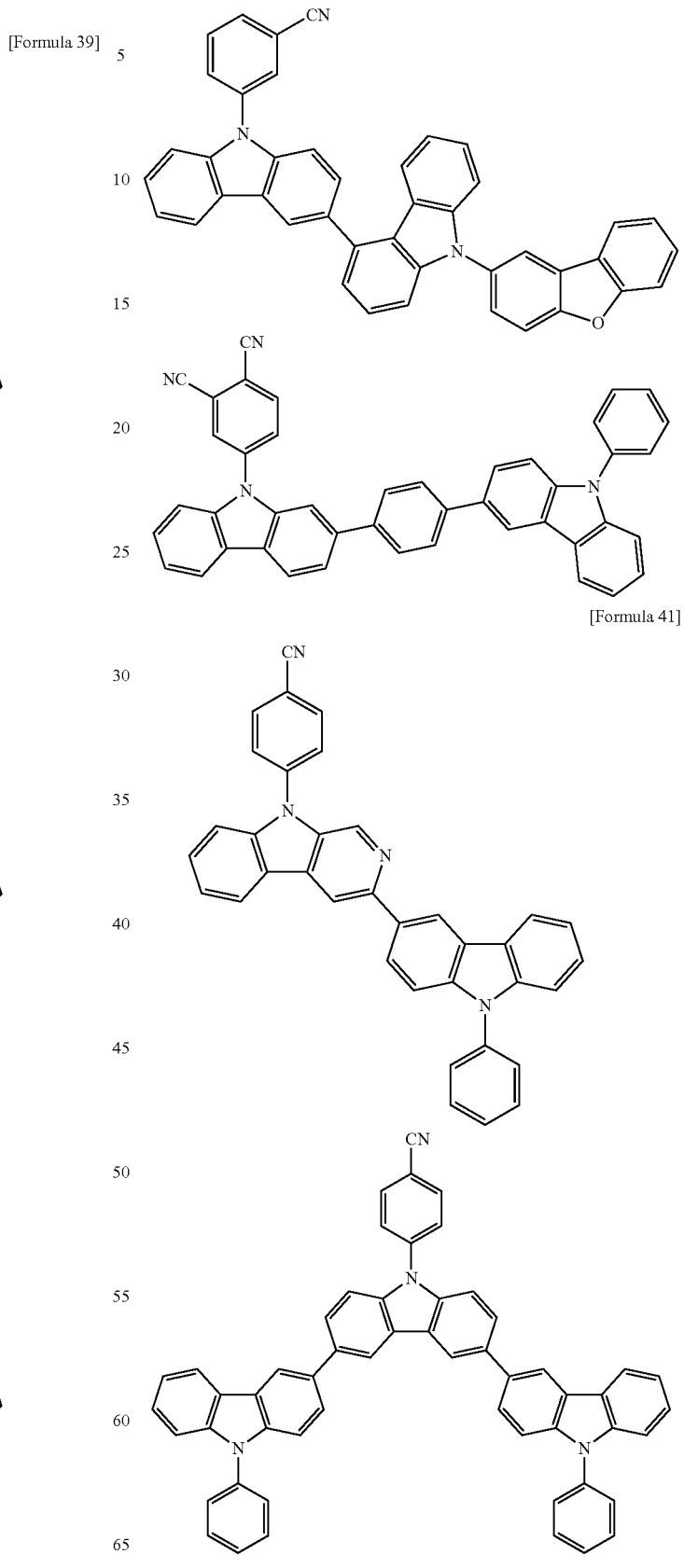

Method of Preparing Second Material

The second material may be prepared by reacting a commercially available compound having the moiety represented by the formula (2), in which at least one of $Z_1$ to $Z_6$ is a carbon atom bonded to a halogen atom, with a compound represented by the formula (2Y), in which a hydrogen atom is bonded to a nitrogen atom bonded to the cyclic structures F and G, under the presence of a catalyst such as tetrakis(triphenylphosphine)palladium and base.

Third Material

The third material of the exemplary embodiment has a singlet energy larger than that of the second material.

In the exemplary embodiment, the third material preferably has at least one of a moiety represented by a formula (31) below and a moiety represented by a formula (32) below in one molecule.

[Formula 42]

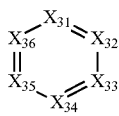
(31)

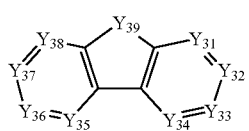
(32)

In the formula (31), $X_{31}$ to $X_{36}$ each independently represent a nitrogen atom, or a carbon atom bonded to another atom in the molecule of the third material, and at least one of $X_{31}$ to $X_{36}$ is the carbon atom bonded to another atom in the molecule of the third material.

In the formula (32), $Y_{31}$ to $Y_{38}$ each independently represent a nitrogen atom, or a carbon atom bonded to another atom in the molecule of the third material, at least one of $Y_{31}$ to $Y_{38}$ is the carbon atom bonded to another atom in the molecule of the third material, and $Y_{39}$ represents a nitrogen atom, oxygen atom or sulfur atom.

In the exemplary embodiment, the moiety represented by the formula (31) is preferably in the form of at least one group selected from the group consisting of formulae (33) and (34) below and contained in the third material.

For the third material, bonding positions are preferably both situated in meta positions as shown in the formulae (33) and (34) to keep an energy gap $Eg_{77K}(M3)$ at 77 [K] high.

[Formula 43]

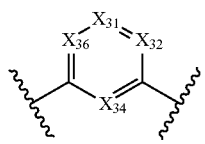
(33)

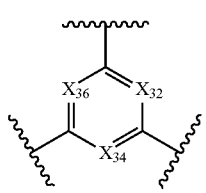
(34)

In the formulae (33) and (34), $X_{31}$, $X_{32}$, $X_{34}$ and $X_{36}$ each independently represent a nitrogen atom or $CR_{31}$, $R_{31}$ being a hydrogen atom or a substituent, the substituent being selected from the group consisting of a halogen atom, a cyano group, a substituted or unsubstituted alkyl group having 1 to 30 carbon atoms, a substituted or unsubstituted cycloalkyl group having 3 to 30 ring carbon atoms, a substituted or unsubstituted trialkylsilyl group, a substituted or unsubstituted arylalkylsilyl group, a substituted or unsubstituted triarylsilyl group, a substituted or unsubstituted diaryl phosphine oxide group, a substituted or unsubstituted aromatic hydrocarbon group having 6 to 30 ring carbon atoms, and a substituted or unsubstituted heterocyclic group having 5 to 30 ring atoms, the substituted or unsubstituted aromatic hydrocarbon group having 6 to 30 ring carbon atoms being a non-fused ring.

In the formulae (33) and (34), a wavy line(s) shows a bonding position with another atom or another structure in the molecule of the third material.

In the exemplary embodiment, $R_{31}$ is preferably a hydrogen atom or a substituent, the substituent being selected from the group consisting of a halogen atom, cyano group, substituted or unsubstituted alkyl group having 1 to 30 carbon atoms, substituted or unsubstituted aromatic hydrocarbon group having 6 to 30 ring carbon atoms, and substituted or unsubstituted heterocyclic group having 5 to 30 ring atoms. $R_{31}$ is more preferably a hydrogen atom, cyano group, substituted or unsubstituted aromatic hydrocarbon group having 6 to 30 ring carbon atoms, or substituted or unsubstituted heterocyclic group having 5 to 30 ring atoms.

In the exemplary embodiment, $X_{31}$, $X_{32}$, $X_{34}$ and $X_{36}$ in the formula (33) each independently represent $CR_{31}$.

In the exemplary embodiment, $X_{32}$, $X_{34}$ and $X_{36}$ in the formula (34) each independently represent $CR_{31}$.

In the exemplary embodiment, the moiety represented by the formula (32) is preferably in the form of at least one group selected from the group consisting of formulae (35), (36), (37), (38), (39) and (30a) below and contained in the third material.

For the third material, bonding positions are preferably situated as shown in the formulae (35), (36), (37), (38), (39) and (30a) to keep the energy gap $Eg_{77K}$ at 77 [K] high.

[Formula 44]

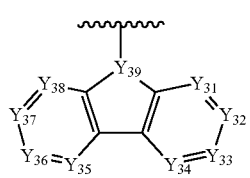
(35)

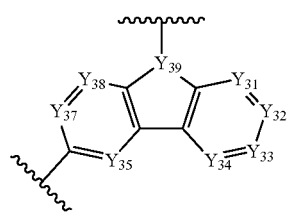
(36)

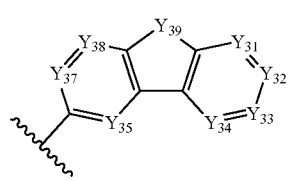
(37)

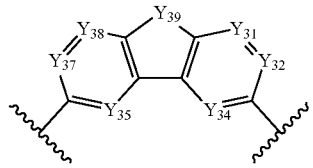

[Formula 45]

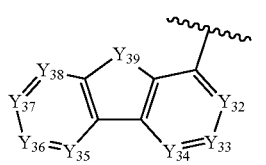

(38)

(39)

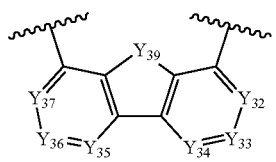

(30a)

In the formulae (35) to (39) and (30a), $Y_{31}$ to $Y_{38}$ each independently represent a nitrogen atom or $CR_{32}$, $R_{32}$ being a hydrogen atom or a substituent, the substituent being selected from the group consisting of a halogen atom, a cyano group, a substituted or unsubstituted alkyl group having 1 to 30 carbon atoms, a substituted or unsubstituted cycloalkyl group having 3 to 30 ring carbon atoms, a substituted or unsubstituted trialkylsilyl group, a substituted or unsubstituted arylalkylsilyl group, a substituted or unsubstituted triarylsilyl group, a substituted or unsubstituted diaryl phosphine oxide group, a substituted or unsubstituted aromatic hydrocarbon group having 6 to 30 ring carbon atoms, and a substituted or unsubstituted heterocyclic group having 5 to 30 ring atoms, the substituted or unsubstituted aromatic hydrocarbon group having 6 to 30 ring carbon atoms being a non-fused ring.

In the formulae (35) and (36), $Y_{39}$ represents a nitrogen atom.

In the formulae (37) to (39) and (30a), $Y_{39}$ represents $NR_{33}$, an oxygen atom or a sulfur atom, $R_{33}$ being a substituent that is selected from the group consisting of a cyano group, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, a substituted or unsubstituted aryl group having 6 to 30 ring carbon atoms, and a substituted or unsubstituted heterocyclic group having 5 to 30 ring atoms, the substituted or unsubstituted aromatic hydrocarbon group having 6 to 30 ring carbon atoms being a non-fused ring.

In the formulae (35) to (39) and (30a), a wavy line(s) shows a bonding position with another atom or another structure in the molecule of the third material.

In the exemplary embodiment, $R_{32}$ is preferably a hydrogen atom or a substituent, the substituent being selected from the group consisting of a halogen atom, cyano group, substituted or unsubstituted alkyl group having 1 to 30 carbon atoms, substituted or unsubstituted aromatic hydrocarbon group having 6 to 30 ring carbon atoms, and substituted or unsubstituted heterocyclic group having 5 to 30 ring atoms. $R_{32}$ is more preferably a hydrogen atom or a substituted or unsubstituted alkyl group having 1 to 30 carbon atoms.

In the exemplary embodiment, $Y_{31}$ to $Y_{38}$ in the formula (35) each independently represent $CR_{32}$.

In the formulae (36) and (37), $Y_{31}$ to $Y_{35}$, $Y_{37}$ and $Y_{38}$ preferably each independently represent $CR_{32}$.

In the formula (38), $Y_{31}$, $Y_{32}$, $Y_{34}$, $Y_{35}$, $Y_{37}$ and $Y_{38}$ preferably each independently represent $CR_{32}$.

In the formula (39), $Y_{32}$ to $Y_{38}$ preferably each independently represent $CR_{32}$.

In the formula (30a), $Y_{32}$ to $Y_{37}$ preferably each independently represent $CR_{32}$.

In the above case, a plurality of $R_{32}$ may be mutually the same or different.

In the exemplary embodiment, the third material preferably contains a group represented by a formula (30b) below.

For the third material, a bonding position is preferably situated as shown in the formula (30b) to keep the energy gap $Eg_{77K}$ at 77 [K] high.

[Formula 46]

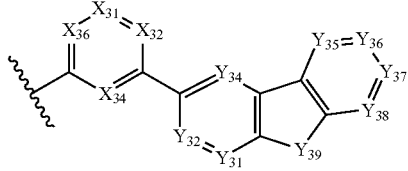

(30b)

In the formula (30b): $X_{31}$, $X_{32}$, $X_{34}$ and $X_{36}$ each independently represent a nitrogen atom or $CR_{31}$; $Y_{31}$, $Y_{32}$ and $Y_{34}$ to $Y_{38}$ each independently represent a nitrogen atom, $CR_{32}$ or a carbon atom bonded to another atom in the molecule of the third material; $R_{31}$ and $R_{32}$ each independently represent a hydrogen atom or a substituent, the substituent being selected from the group consisting of a halogen atom, cyano group, substituted or unsubstituted alkyl group having 1 to 30 carbon atoms, substituted or unsubstituted cycloalkyl group having 3 to 30 ring carbon atoms, substituted or unsubstituted trialkylsilyl group, substituted or unsubstituted arylalkylsilyl group, substituted or unsubstituted triarylsilyl group, substituted or unsubstituted diaryl phosphine oxide group, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; $Y_{39}$ represents $NR_{33}$, an oxygen atom or a sulfur atom, $R_{33}$ being a substituent that is selected from the group consisting of a cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; $X_{32}$ and $Y_{34}$ may be cross-linked via an oxygen atom, sulfur atom or $CR_{51}R_{52}$; $X_{34}$ and $Y_{32}$ may be cross-linked via an oxygen atom, sulfur atom or $CR_{53}R_{54}$; and $R_{51}$ to $R_{54}$ each independently represent the same as $R_{33}$ being the substituent.

In the formula (30b), a wavy line(s) shows a bonding position with another atom or another structure in the molecule of the third material.

For instance, when $X_{32}$ and $Y_{34}$ are cross-linked via an oxygen atom, sulfur atom or $CR_{51}R_{52}$ in the formula (30b), the formula (30b) is represented by a formula (30b-1) below.

[Formula 47]

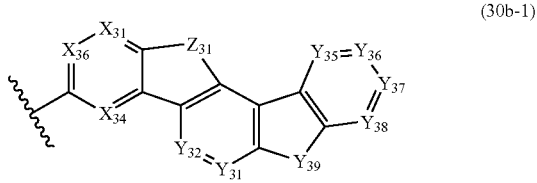

(30b-1)

It should be noted that $Z_{31}$ is an oxygen atom, sulfur atom or $CR_{51}R_{52}$ in the formula (30b-1).

In the exemplary embodiment, the third material preferably contains a group represented by a formula (30c) below.

For the third material, a bonding position is preferably situated as shown in the formula (30c) to keep the energy gap $Eg_{77K}$ at 77 [K] high.

[Formula 48]

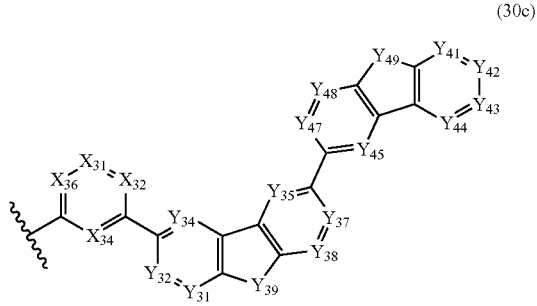

(30c)

In the formula (30c): $X_{31}$, $X_{32}$, $X_{34}$ and $X_{36}$ each independently represent a nitrogen atom or $CR_{31}$; $Y_{31}$, $Y_{32}$, $Y_{34}$, $Y_{35}$, $Y_{37}$ and $Y_{38}$ each independently represent a nitrogen atom or $CR_{32}$; $Y_{41}$ to $Y_{45}$, $Y_{47}$ and $Y_{48}$ each independently represent a nitrogen atom, $CR_{34}$ or a carbon atom bonded to another atom in the molecule of the third material; $R_{31}$, $R_{32}$ and $R_{34}$ each independently represent a hydrogen atom or a substituent, the substituent being selected from the group consisting of a halogen atom, cyano group, substituted or unsubstituted alkyl group having 1 to 30 carbon atoms, substituted or unsubstituted cycloalkyl group having 3 to 30 ring carbon atoms, substituted or unsubstituted trialkylsilyl group, substituted or unsubstituted arylalkylsilyl group, substituted or unsubstituted triarylsilyl group, substituted or unsubstituted diaryl phosphine oxide group, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; $Y_{39}$ represents $NR_{33}$, an oxygen atom or a sulfur atom; $Y_{49}$ represents $NR_{35}$, an oxygen atom or a sulfur atom; $R_{33}$ and $R_{35}$ each independently represent a substituent that is selected from the group consisting of a cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; $X_{32}$ and $Y_{34}$ may be cross-linked via an oxygen atom, sulfur atom or $CR_{51}R_{52}$; $X_{34}$ and $Y_{32}$ may be cross-linked via an oxygen atom, sulfur atom or $CR_3R_{54}$; and $R_{51}$ to $R_{54}$ each independently represent the same as $R_{33}$ and $R_{35}$ each being the substituent.

In the formula (30c), a wavy line(s) shows a bonding position with another atom or another structure in the molecule of the third material.

For instance, when $X_{32}$ and $Y_{34}$ are cross-linked via an oxygen atom, sulfur atom or $CR_{51}R_{52}$ in the formula (30c), the formula (30c) is represented by a formula (30c-1) below.

[Formula 49]

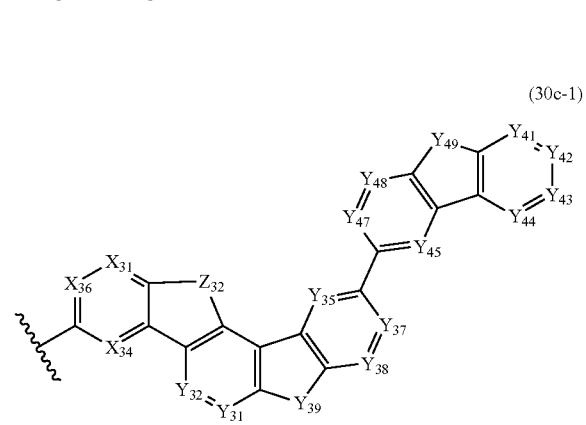

(30c-1)

It should be noted that $Z_{32}$ is an oxygen atom, sulfur atom or $CR_{51}R_{52}$ in the formula (30c-1).

In the exemplary embodiment, the third material preferably contains a group represented by a formula (30d) below.

For the third material, bonding positions are preferably situated as shown in the formula (30d) to keep the energy gap $Eg_{77K}$ at 77 [K] high.

[Formula 50]

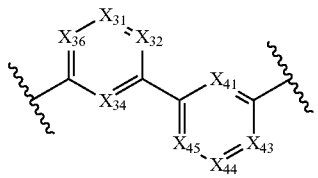

(30d)

In the formula (30d): $X_{31}$, $X_{32}$, $X_{34}$ and $X_{36}$ each independently represent a nitrogen atom or $CR_{31}$; $X_{41}$, $X_{43}$, $X_{44}$ and $X_{45}$ each independently represent a nitrogen atom or $CR_{36}$; $R_{31}$ and $R_{36}$ each independently represent a substituent that is selected from the group consisting of a halogen atom, cyano group, substituted or unsubstituted alkyl group having 1 to 30 carbon atoms, substituted or unsubstituted cycloalkyl group having 3 to 30 ring carbon atoms, substituted or unsubstituted trialkylsilyl group, substituted or unsubstituted arylalkylsilyl group, substituted or unsubstituted triarylsilyl group, substituted or unsubstituted diaryl phosphine oxide group, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; $X_{32}$ and $X_{41}$ may be cross-linked via an oxygen atom, sulfur atom or $CR_{55}R_{56}$; $X_{34}$ and $X_{45}$ may be cross-linked via an oxygen atom, sulfur atom or $CR_{57}R_{58}$; and $R_{55}$ to $R_{58}$ each independently represent a substituent that is selected from the group consisting of a halogen atom, cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring.

In the formula (30d), a wavy line(s) shows a bonding position with another atom or another structure in the molecule of the third material.

For instance, when $X_{32}$ and $X_{41}$ are cross-linked via an oxygen atom, sulfur atom or $CR_{55}R_{56}$ in the formula (30d), the formula (30d) is represented by a formula (30d-1) below.

[Formula 51]

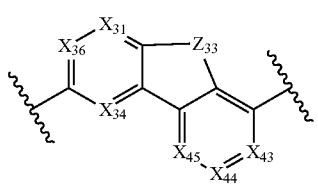

(30d-1)

It should be noted that $Z_{33}$ is an oxygen atom, sulfur atom or $CR_{55}R_{56}$ in the formula (30d-1).

In the exemplary embodiment, the third material preferably contains a group represented by a formula (30e) below.

For the third material, a bonding position is preferably situated as shown in the formula (30e) to keep the energy gap $Eg_{77K}$ at 77 [K] high.

[Formula 52]

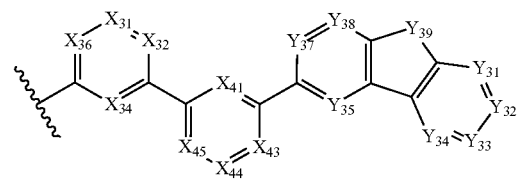

(30e)

In the formula (30e): $X_{31}$, $X_{32}$, $X_{34}$ and $X_{36}$ each independently represent a nitrogen atom or $CR_{31}$; $X_{41}$, $X_{43}$, $X_{44}$ and $X_{45}$ each independently represent a nitrogen atom or $CR_{36}$; $Y_{31}$ to $Y_{35}$, $Y_{37}$ and $Y_{38}$ each independently represent a nitrogen atom, $CR_{32}$ or a carbon atom bonded to another atom in the molecule of the third material; $R_{31}$, $R_{32}$ and $R_{36}$ each independently represent a hydrogen atom or a substituent, the substituent being selected from the group consisting of a halogen atom, cyano group, substituted or unsubstituted alkyl group having 1 to 30 carbon atoms, substituted or unsubstituted cycloalkyl group having 3 to 30 ring carbon atoms, substituted or unsubstituted trialkylsilyl group, substituted or unsubstituted arylalkylsilyl group, substituted or unsubstituted triarylsilyl group, substituted or unsubstituted diaryl phosphine oxide group, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; $Y_{39}$ represents $NR_{33}$, an oxygen atom or a sulfur atom, $R_{33}$ being a substituent that is selected from the group consisting of a cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; $X_{32}$ and $X_{41}$ may be cross-linked via an oxygen atom, sulfur atom or $CR_{55}R_{56}$; $X_{34}$ and $X_{45}$ may be cross-linked via an oxygen atom, sulfur atom or $CR_{57}R_{58}$; $X_{41}$ and $Y_{37}$ may be cross-linked via an oxygen atom, sulfur atom or $CR_{59}R_{60}$; $X_{43}$ and $Y_{35}$ may be cross-linked via an oxygen atom, sulfur atom or $CR_{61}R_{62}$; and $R_{55}$ to $R_{62}$ each independently represent the same as $R_{33}$ being the substituent.

In the formula (30e), a wavy line(s) shows a bonding position with another atom or another structure in the molecule of the third material.

For instance, when $X_{32}$ and $X_{41}$ are cross-linked via an oxygen atom, sulfur atom or $CR_{55}R_{56}$ in the formula (30e), the formula (30e) is represented by a formula (30e-1) below.

[Formula 53]

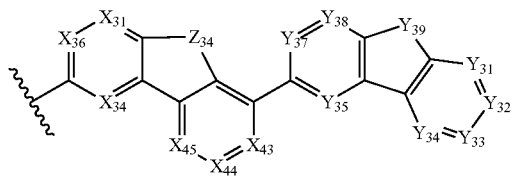

(30e-1)

It should be noted that $Z_{34}$ is an oxygen atom, sulfur atom or $CR_{55}R_{56}$ in the formula (30e-1).

For instance, when $X_{41}$ and $Y_{37}$ are cross-linked via an oxygen atom, sulfur atom or $CR_{59}R_{60}$ in the formula (30e), the formula (30e) is represented by a formula (30e-2) below.

[Formula 54]

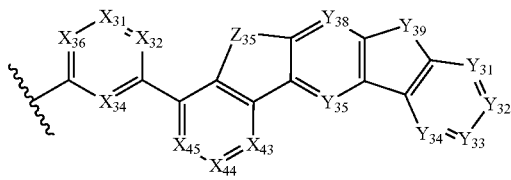

(30e-2)

It should be noted that $Z_{35}$ is an oxygen atom, sulfur atom or $CR_{59}R_{60}$ in the formula (30e-2).

In the exemplary embodiment, the third material preferably contains a group represented by a formula (30f) below.

For the third material, a bonding position is preferably situated as shown in the formula (30f) to keep the energy gap $Eg_{77K}$ at 77 [K] high.

[Formula 55]

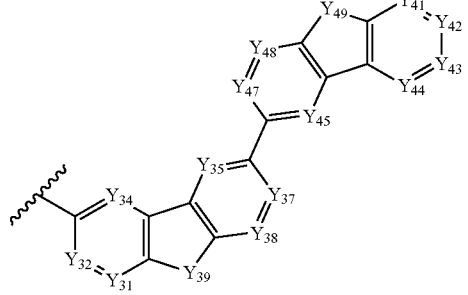

(30f)

In the formula (30f): $Y_{31}$, $Y_{32}$, $Y_{34}$, $Y_{35}$, $Y_{37}$ and $Y_{38}$ each independently represent a nitrogen atom or $CR_{32}$; $Y_{41}$ to $Y_{45}$, $Y_{47}$ and $Y_{48}$ each independently represent a nitrogen atom, $CR_{34}$ or a carbon atom bonded to another atom in the molecule of the third material; $R_{32}$ and $R_{34}$ each independently represent a hydrogen atom or a substituent, the substituent being selected from the group consisting of a halogen atom, cyano group, substituted or unsubstituted alkyl group having 1 to 30 carbon atoms, substituted or unsubstituted cycloalkyl group having 3 to 30 ring carbon atoms, substituted or unsubstituted trialkylsilyl group, substituted or unsubstituted arylalkylsilyl group, substituted or unsubstituted triarylsilyl group, substituted or unsubstituted diaryl phosphine oxide group, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; $Y_{39}$ represents $NR_{33}$, an oxygen atom or a sulfur atom; $Y_{49}$ represents $NR_{35}$, an oxygen atom or a sulfur atom; and $R_{33}$ and $R_{35}$ each independently represent a hydrogen atom or a substituent, the substituent being selected from the group consisting of a cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring.

In the formula (30f), a wavy line(s) shows a bonding position with another atom or another structure in the molecule of the third material.

In the exemplary embodiment, the third material may contain at least one of groups represented by formulae (30g), (30h) and (30i) below.

[Formula 56]

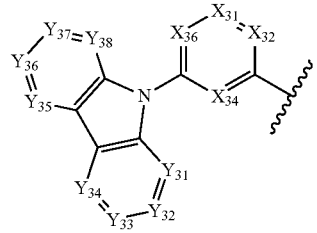

(30g)

[Formula 57]

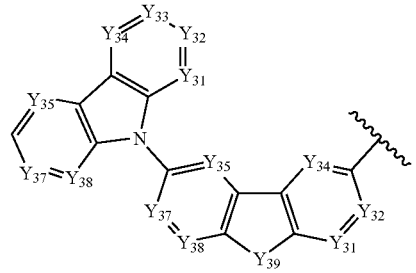

(30h)

-continued

[Formula 58]

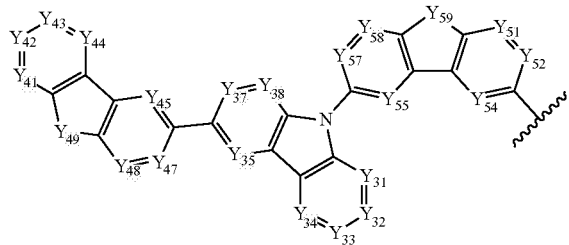

(30i)

In the formulae (30g), (30h) and (30i): $Y_{31}$ to $Y_{38}$, $Y_{41}$ to $Y_{48}$ and $Y_{51}$ to $Y_{58}$ each independently represent a nitrogen atom, $CR_{37}$ or a carbon atom bonded to another atom in the molecule of the third material; $R_{37}$ each independently represent a hydrogen atom or a substituent, the substituent being selected from the group consisting of a halogen atom, cyano group, substituted or unsubstituted alkyl group having 1 to 30 carbon atoms, substituted or unsubstituted cycloalkyl group having 3 to 30 ring carbon atoms, substituted or unsubstituted trialkylsilyl group, substituted or unsubstituted arylalkylsilyl group, substituted or unsubstituted triarylsilyl group, substituted or unsubstituted diaryl phosphine oxide group, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring; and $Y_{49}$ and $Y_{59}$ each independently represent $NR_{38}$, an oxygen atom or a sulfur atom, $R_{38}$ being each independently a hydrogen atom or a substituent, the substituent being selected from the group consisting of a halogen atom, cyano group, substituted or unsubstituted alkyl group having 1 to 20 carbon atoms, substituted or unsubstituted cycloalkyl group having 3 to 20 ring carbon atoms, substituted or unsubstituted alkoxy group having 1 to 20 carbon atoms, substituted or unsubstituted aryloxy group having 6 to 30 ring carbon atoms, substituted or unsubstituted alkylthio group having 1 to 20 carbon atoms, substituted or unsubstituted arylthio group having 6 to 30 ring carbon atoms, substituted or unsubstituted alkylsilyl group having 3 to 50 carbon atoms, substituted or unsubstituted arylsilyl group having 6 to 50 ring carbon atoms, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms being a non-fused ring.

In the formulae (30g), (30h) and (30i), a wavy line(s) shows a bonding position with another atom or another structure in the molecule of the third material.

In the formulae (32), (35), (36), (37), (38), (39), (30a), (30b), (30c), (30e), (30f), (30h) and (30i), when $Y_{39}$ and $Y_{49}$ are each independently an oxygen atom or a sulfur atom, an ionization potential Ip is increased, which is preferable for the third material. When $Y_{39}$ and $Y_{49}$ are each an oxygen atom, the ionization potential Ip is further increased, which is further preferable.

In the exemplary embodiment, the third material is also preferably an aromatic hydrocarbon compound or an aromatic heterocyclic compound.

Method of Preparing Third Material

The third material represented by the formula may be prepared by a method described in WO2012/153780 A1 or WO 2013/038650 A1.

Specific examples of the substituent for the third material of the exemplary embodiment are shown below, but the invention is not limited thereto.

Specific examples of the aromatic hydrocarbon group (aryl group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group, among which a phenyl group, biphenyl group, terphenyl group, quarterphenyl group, naphthyl group, triphenylenyl group and fluorenyl group may be preferable.

Specific examples of the substituted aromatic hydrocarbon group include a tolyl group, xylyl group and 9,9-dimethylfluorenyl group.

As is understood from the specific examples, the aryl group includes both fused aryl group and non-fused aryl group.

Preferable examples of the aromatic hydrocarbon group include a phenyl group, biphenyl group, terphenyl group, quarterphenyl group, naphthyl group, triphenylenyl group and fluorenyl group.

For an organic EL device including a blue-emitting layer, the aromatic hydrocarbon group as a substituent in the third material is preferably a non-fused aromatic hydrocarbon group.

Specific examples of the aromatic heterocyclic group (heteroaryl group, heteroaromatic ring group and heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothiophenyl group, dibenzothiophenyl group, azadibenzothiophenyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothiophenyl group, carbazolyl group, pyridyl group, pyrimidinyl group, triazinyl group, azadibenzofuranyl group and azadibenzothiophenyl group may be preferable.

The aromatic heterocyclic group is preferably any one of a dibenzofuranyl group, dibenzothiophenyl group, carbazolyl group, pyridyl group, pyrimidinyl group, triazinyl group, azadibenzofuranyl group and azadibenzothiophenyl group, and further preferably any one of a dibenzofuranyl group, dibenzothiophenyl group, azadibenzofuranyl group and azadibenzothiophenyl group.

Specific examples of the trialkylsilyl group include a trimethylsilyl group and a triethylsilyl group. Specific examples of the substituted or unsubstituted arylalkylsilyl group include a diphenylmethylsilyl group, ditolylmethylsilyl group and phenyldimethylsilyl group. Specific examples of the substituted or unsubstituted triarylsilyl group include a triphenylsilyl group and a tritolylsilyl group.

Specific examples of the diaryl phosphine oxide group include a diphenyl phosphine oxide group and ditolyl phosphine oxide group.

When $R_1$, $R_a$, $Ar_1$, $Ar_2$, $Ar_3$ and $Ar_4$ are substituted, examples of the substituents include a substituted or unsubstituted alkyl group having 1 to 30 carbon atoms, substituted or unsubstituted cycloalkyl group having 3 to 30 ring carbon atoms, substituted or unsubstituted trialkylsilyl group, substituted or unsubstituted arylalkylsilyl group, substituted or unsubstituted triarylsilyl group, substituted or unsubstituted diaryl phosphine oxide group, substituted or unsubstituted aromatic hydrocarbon ring group having 6 to 30 ring carbon atoms, and substituted or unsubstituted aromatic heterocyclic group having 5 to 30 ring atoms, among which a substituted or unsubstituted aromatic hydrocarbon ring group having 6 to 30 ring carbon atoms and substituted or unsubstituted aromatic heterocyclic group having 5 to 30 ring atoms are preferable. Specific examples of the aromatic hydrocarbon ring group include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group and fluoranthenyl group. Specific examples of the aromatic heterocyclic group include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothiophenyl group, dibenzothiophenyl group, azadibenzothiophenyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group.

For an organic EL device including a blue-emitting layer, the aromatic heterocyclic group as a substituent in the third material is preferably a non-fused aromatic heterocyclic group.

Specific examples of the third material of the exemplary embodiment are shown below. It should be noted that the third material according to the invention may be different from these specific examples.

[Formula 59]

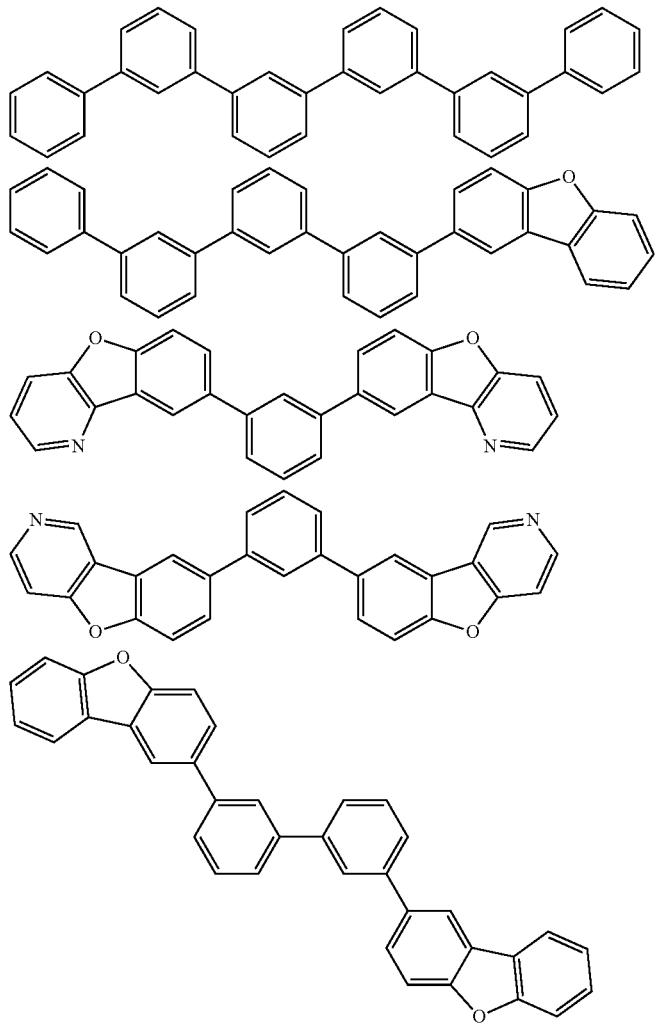

-continued
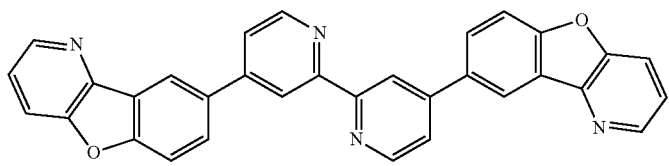
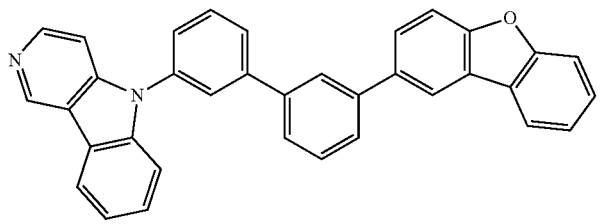
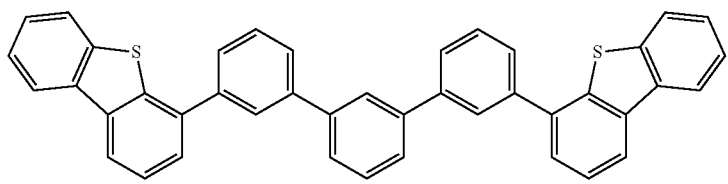
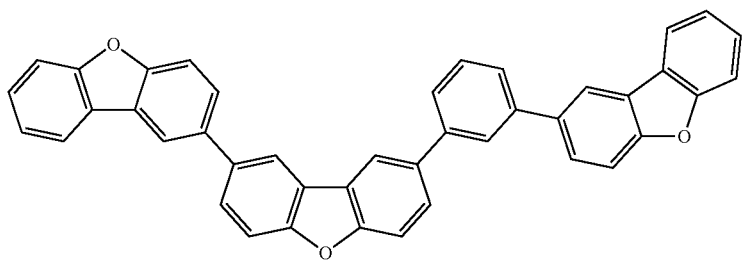
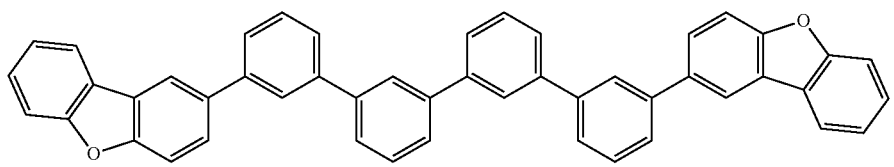
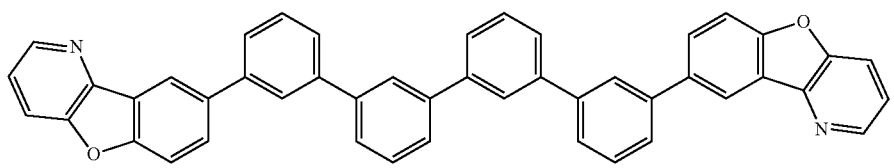
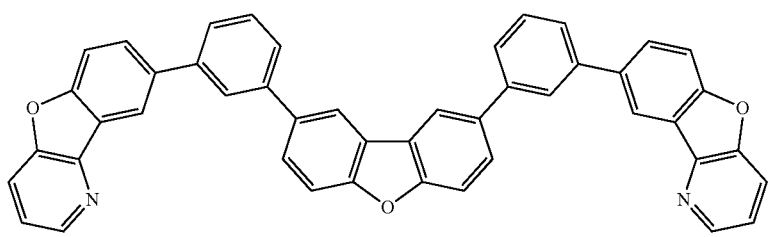
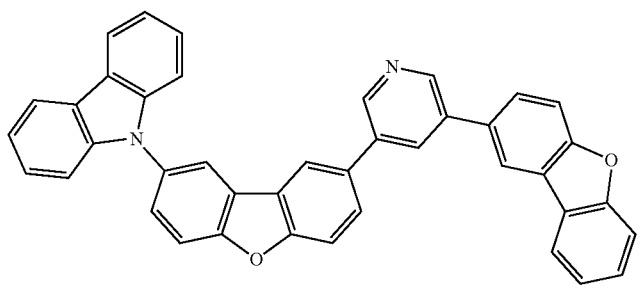
[Formula 60]

[Formula 61]
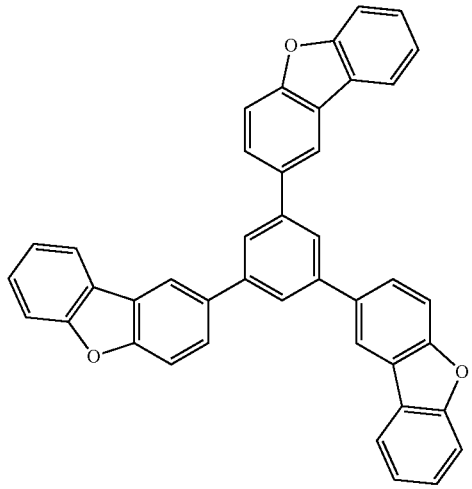
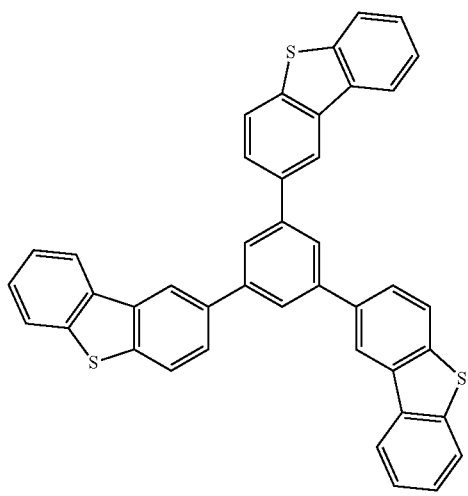
[Formula 62]
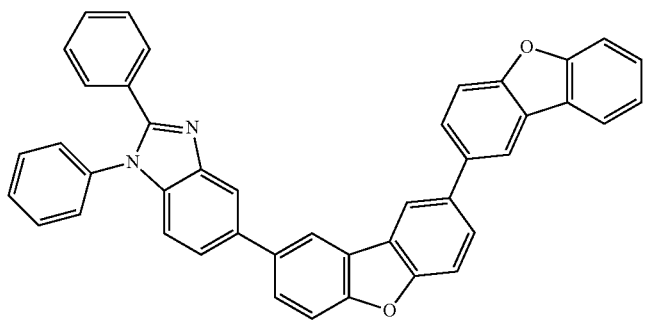
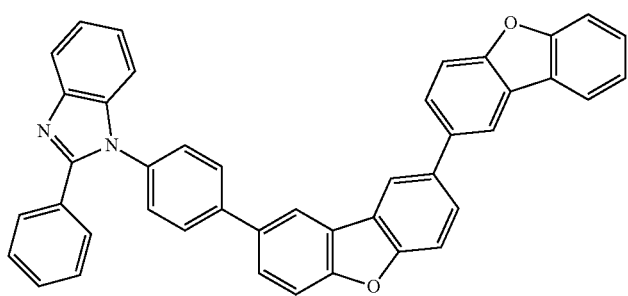

-continued

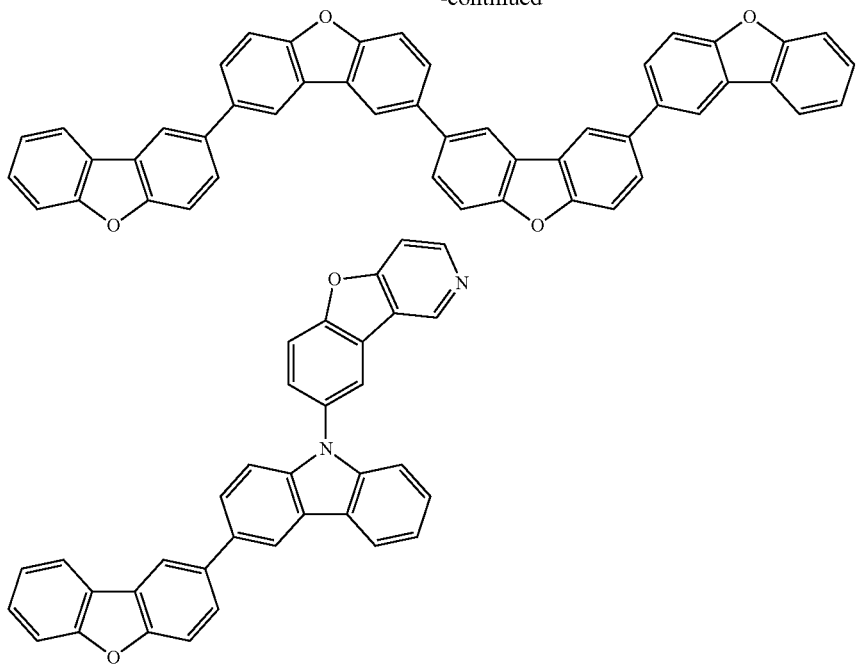

Relationship Between First Material, Second Material and Third Material in Emitting Layer In the exemplary embodiment, the third material is inferred to function as a dispersant that suppresses molecular association of the second material of the exemplary embodiment with another in the emitting layer.

The second material of the exemplary embodiment is a thermally activated delayed fluorescent material, and thus is likely to undergo molecular association. An excitation energy of a molecular assembly (i.e., singlet energy and triplet energy) is small as compared with an excitation energy of a monomer. Therefore, it is predicted that an increase in the concentration of the second material in the thin film should result in energy loss attributed to molecular association.

Accordingly, especially when the emitting layer contains a blue-emitting fluorescent material with a large excitation energy, the third material contributes to suppressing the energy loss attributed to molecular association, which results in improvement in the efficiency of the organic EL device. Similarly, when the emitting layer contains a luminescent material emitting light with a wavelength ranging from a red-light wavelength range to a yellow-light wavelength range, the third material contributes to improving a carrier balance factor, which results in improvement in the efficiency of the organic EL device.

Typical fluorescent organic EL device and phosphorescent organic EL device seem not to be improved in luminous efficiency by adding the third material, which has a function different from a function as a host material and a function as a luminescent material, to the emitting layer as in the exemplary embodiment. In contrast, the thermally activated delayed fluorescent organic EL device of the exemplary embodiment has a potential for a significant change in a carrier balance factor, because, while the thermally activated delayed fluorescent material with a relatively small singlet energy causes carrier transport in the emitting layer, the third material with a singlet energy larger than that of the second material is unlikely to cause carrier transport. This results in contribution to improvement in the efficiency of the organic EL device.

Since the singlet energy of the third material is larger than that of the second material, the excited third material is unstable as compared with the first material and the second material. Accordingly, the third material preferably has no influence on generation of excitons and carrier transport in the emitting layer. For a typical organic EL device, such a third material is a unique material in view of criteria for selecting a material to be contained in the emitting layer. While the emitting layer of a typical florescent organic EL device selectively contains a material with high electrical and optical functions, the emitting layer of the exemplary embodiment contains the third material that has no influence on generation of excitons and carrier transport.

In the exemplary embodiment, a singlet energy EgS(M2) of the second material is preferably larger than the singlet energy EgS(M1) of the first material.

In other words, a relationship of EgS(M1)<EgS(M2)<EgS(M3) is preferably satisfied.

In the exemplary embodiment, it is preferable that an energy gap $Eg_{77K}$(M2) at 77 [K] of the second material is larger than an energy gap $Eg_{77K}$(M1) at 77 [K] of the first material, and an energy gap $Eg_{77K}$(M3) at 77 [K] of the third material is larger than the energy gap $Eg_{77K}$(M2) at 77 [K] of the second material.

In other words, a relationship of $Eg_{77K}$(M1)<$Eg_{77K}$(M2)<$Eg_{77K}$(M3) is preferably satisfied.

In the exemplary embodiment, a difference ΔST(M2) between the singlet energy EgS(M2) of the second material and the energy gap $Eg_{77K}$(M2) at 77 [K] of the second material preferably satisfies a relationship of a numerical formula (Numerical Formula 1) below.

$$\Delta ST(M2)=EgS(M2)-Eg_{77K}(M2)<0.3 \text{ [eV]} \quad \text{(Numerical Formula 1)}$$

ΔST(M2) is preferably less than 0.2 [eV].

In the exemplary embodiment, a difference ΔST(M1) between the singlet energy EgS(M1) of the first material and the energy gap $Eg_{77K}(M1)$ at 77 [K] of the first material preferably satisfies a relationship of a numerical formula (Numerical Formula 2) below.

$$\Delta ST(M1)=EgS(M1)-Eg_{77K}(M1)>0.3 \text{ [eV]} \quad \text{(Numerical Formula 2)}$$

In the exemplary embodiment, a difference $\Delta ST(M3)$ between the singlet energy $EgS(M3)$ of the third material and the energy gap $Eg_{77K}(M3)$ at 77[K] of the third material preferably satisfies a relationship of a numerical formula (Numerical Formula 3) below.

$$\Delta ST(M3)=EgS(M3)-Eg_{77K}(M3)>0.3 \text{ [eV]} \quad \text{(Numerical Formula 3)}$$

In the exemplary embodiment, the $Eg_{77K}(M3)$ at 77 [K] of the third material is preferably 2.9 eV or more. When the $Eg_{77K}(M3)$ of the third material is in the above range, the third material is unlikely to affect generation of excitons and carrier transport in the emitting layer.

ΔST

From a quantum chemical viewpoint, decrease in the energy difference (ΔST) between the singlet energy EgS and the triplet energy EgT can be achieved by a small exchange interaction therebetween. Physical details of the relationship between ΔST and the exchange interaction are described, for instance, in Reference Document 1 and Reference Document 2 below.

Reference Document 2: ADACHI, Chihaya, et al. (ed.), Organic EL Symposium, proceeding for the tenth meeting, S2-5, pp. 11-12

Reference Document 3: TOKUMURA, Katsumi (ed.) (1973), *Yuki Hikari Kagaku Hanno-ron* (*Organic Photochemical Reaction Theory*), Tokyo Kagaku Dojin Co., Ltd.

Such a material can be synthesized according to molecular design based on quantum calculation. Specifically, the material is a compound in which a LUMO electron orbit and a HOMO electron orbit are localized to avoid overlapping.

Examples of the compound having a small ΔST used as the second material of the exemplary embodiment include compounds in which a donor element is bonded to an acceptor element in a molecule and ΔST is in a range of 0 eV or more and less than 0.3 eV in view of electrochemical stability (oxidation-reduction stability).

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that ΔST can be further reduced by the interaction of the molecules. In such a case, ΔST can be extremely small in a range of 0 eV to 0.2 eV.

TADF Mechanism

In the organic EL device of the exemplary embodiment, the second material is preferably a compound having a small $\Delta ST(M2)$ so that inverse intersystem crossing from the triplet energy level of the second material to the singlet energy level thereof is easily caused by a heat energy given from the outside. An energy state conversion mechanism to perform spin exchange from the triplet state of electrically excited excitons within the organic EL device to the singlet state by inverse intersystem crossing is referred to as a TADF mechanism.

Figure 4:
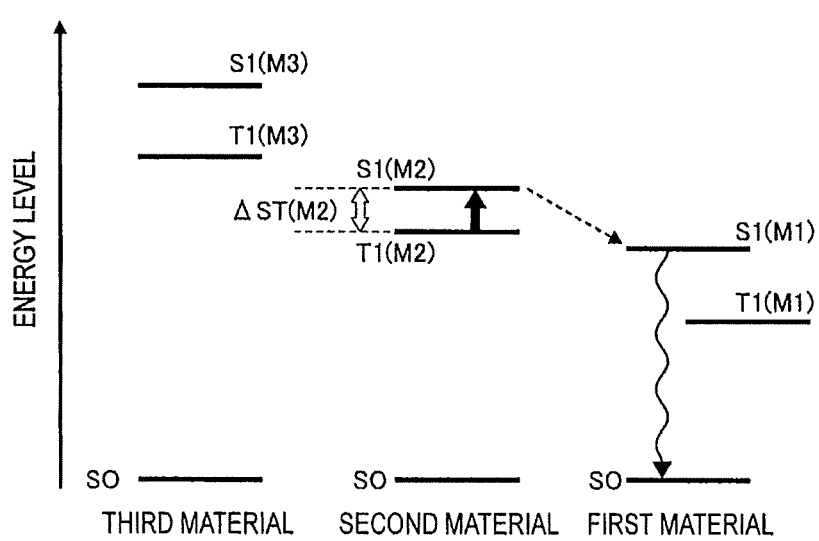
FIG. 4 shows a relationship of energy levels of first, second and third materials in an emitting layer and energy transfer thereamong.

FIG. 4 shows an example of a relationship of energy levels of the first, second and third materials in the emitting layer. In FIG. 4, S0 represents a ground state, S1(M1) represents a lowest singlet state of the first material, T1(M1) represents a lowest triplet state of the first material, S1(M2) represents a lowest singlet state of the second material, T1(M2) represents a lowest triplet state of the second material, S1(M3) represents a lowest singlet state of the third material, and T1(M3) represents a lowest triplet state of the third material. A dashed arrow directed from S1(M2) to S1(M1) in FIG. 4 represents Förster energy transfer from the lowest singlet state of the second material to the lowest singlet state of the first material.

As shown in FIG. 4, when a material having a small $\Delta ST(M2)$ is used as the second material, inverse intersystem crossing from the lowest triplet state T1(M2) to the lowest singlet state S1(M2) can be caused by a heat energy. Consequently, Förster energy transfer from the lowest singlet state S1(M2) of the second material to the lowest singlet state S1(M1) of the first material is caused. As a result, fluorescence from the lowest singlet state S1(M1) of the first material can be observed. It is inferred that the internal quantum efficiency can be theoretically raised up to 100% also by using delayed fluorescence by the TADF mechanism.

Relationship between Triplet Energy and Energy Gap at 77 [K]

Description will be made on a relationship between a triplet energy and an energy gap at 77 [K]. In the exemplary embodiment, the energy gap at 77 [K] is different from a typical triplet energy in some aspects.

For the first material and the third material (measurement targets), the triplet energy is measured as follows. Specifically, a compound to be measured is dissolved in EPA (diethylether:isopentane:ethanol=5:5:2 in volume ratio) at a concentration of 10 μmol/L, and the resulting solution is set in a quartz cell to provide a measurement sample. A phosphorescence spectrum (ordinate axis: phosphorescent luminous intensity, abscissa axis: wavelength) of the measurement sample is measured at a low temperature (77 [K]), a tangent is drawn at the rise of the phosphorescence spectrum on the short-wavelength side, and an energy amount calculated by the following conversion equation 1 based on a wavelength value $\lambda_{edge}$ [nm] of an intersection between the tangent and the abscissa axis is defined as the energy gap $Eg_{77K}$ at 77 [K].

$$Eg_{77K} \text{ [eV]}=1239.85/\lambda_{edge} \quad \text{Conversion Equation 1:}$$

For phosphorescence measurement, a spectrophotofluorometer body F-4500 (manufactured by Hitachi High-Technologies Corporation) is usable. It should be noted that the phosphorescence measuring device may be different from the above device.

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is hot included in the above-mentioned maximum closest to the short-wavelength side of the spectrum. The tangent drawn at a point of the maximum spectral value being the closest to the short-wavelength side and having the maximum inclination is defined as a tangent to the rise of the phosphorescence spectrum on the short-wavelength side.

For the second material (measurement target), the triplet energy is measured as follows. A compound to be measured (the second material) and a compound TH-2 are co-deposited on a quartz substrate to prepare a sample sealed in an NMR tube. It should be noted that the sample is prepared under the following conditions: quartz substrate/TH-2: second material (film thickness: 100 nm, concentration of second material: 12 mass %).

A phosphorescence spectrum (ordinate axis: phosphorescent luminous intensity, abscissa axis: wavelength) of the measurement sample is measured at a low temperature (77 [K]), a tangent is drawn at the rise of the phosphorescence spectrum on the short-wavelength side, and an energy amount calculated by the following conversion equation 2 based on a wavelength value $\lambda_{edge}$ [nm] of an intersection between the tangent and the abscissa axis is defined as the energy gap $Eg_{77K}$ at 77 [K].

$$Eg_{77K} [eV]=1239.85/\lambda_{edge} \qquad \text{Conversion Equation 2:}$$

For phosphorescence measurement, a spectrophotofluorometer body F-4500 (manufactured by Hitachi High-Technologies Corporation) is usable. It should be noted that the phosphorescence measuring device may be different from the above device.

The tangent to the rise of the phosphorescence spectrum on the short-wavelength side is drawn in the same manner as those of the phosphorescence spectra of the first and second materials.

In the exemplary embodiment, a compound having a small AST is preferably usable as the second material. When AST is small, intersystem crossing and inverse intersystem crossing are likely to occur even at a low temperature (77 [K]), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy EgT, but a value measured in the following manner is referred to as an energy gap $Eg_{77K}$ in order to differentiate the measured energy from the typical triplet energy in a strict meaning.

Singlet Energy EgS

The singlet energy EgS is measured as follows.

A 10-μmol/L toluene solution of a compound to be measured is prepared and put in a quartz cell. An absorption spectrum (ordinate axis: luminous intensity, abscissa axis: intensity) of the thus-obtained sample is measured at a room temperature (300 K). A tangent is drawn at the rise on the long-wavelength side, and a singlet energy is calculated by substituting a wavelength value $\lambda_{edge}$ [nm] of an intersection between the tangent and the abscissa axis into the following conversion equation 3.

$$EgS [eV]=1239.85/\lambda_{edge} \qquad \text{Conversion Equation 3:}$$

In Example, the absorption spectrum is measured using a spectrophotometer manufactured by Hitachi, Ltd. (device name: U3310). It should be noted that the absorption spectrum measuring device may be different from the above device.

In the exemplary embodiment, a difference between the singlet energy EgS and the energy gap $Eg_{77K}$ is defined as ΔST.

In the exemplary embodiment, an ionization potential Ip(M3) of the third material and an ionization potential Ip(M2) of the second material preferably satisfy a relationship of a numerical formula (Numerical Formula 4) below. When this relationship is satisfied, the third material is unlikely to affect generation of excitons and carrier transport in the emitting layer.

$$Ip(M3) \geq Ip(M2) \qquad \text{(Numerical Formula 4)}$$

In the exemplary embodiment, the ionization potential Ip(M3) of the third material is preferably 6.3 eV or more. When the ionization potential Ip(M3) of the third material is in the above range, the third material is unlikely to affect generation of excitons and carrier transport in the emitting layer.

It should be noted that an ionization potential can be measured using a photoelectron spectroscopy device under the atmosphere. Specifically, a material is irradiated with light and the amount of electrons generated by charge separation is measured. The measuring device may be a photoelectron spectroscopy device manufactured by RIKEN KEIKI Co., Ltd. (device name: AC-3).

In the exemplary embodiment, an electron affinity Af(M3) of the third material and an electron affinity Af(M2) of the second material preferably satisfy a relationship of a numerical formula (Numerical Formula 5) below. When this relationship is satisfied, the third material is unlikely to affect generation of excitons and carrier transport in the emitting layer.

$$Af(M3) \geq Af(M2) \qquad \text{(Numerical Formula 5)}$$

In the exemplary embodiment, the electron affinity Af(M3) of the third material is preferably 2.8 eV or more. When the electron affinity Af(M3) of the third material is in the above range, the third material is unlikely to affect generation of excitons and carrier transport in the emitting layer.

The electron affinity can be calculated by a numerical formula (Numerical Formula 8) below from the measurement values of the ionization potential Ip and singlet energy EgS of the compound measured in the above manner.

$$Af=Ip-EgS \qquad \text{(Numerical Formula 8)}$$

Film Thickness of Emitting Layer

A film thickness of the emitting layer of the organic EL device of the exemplary embodiment is preferably in a range from 5 nm to 50 nm, more preferably in a range from 7 nm to 50 nm, and most preferably in a range from 10 nm to 50 nm. The thickness of less than 5 nm may cause difficulty in forming the emitting layer and in controlling chromaticity, while the thickness of more than 50 nm may raise drive voltage.

Content Ratio of Materials in Emitting Layer

In the emitting layer of the organic EL device of the exemplary embodiment, it is preferable that the content ratio of the first emitting layer is in a range from 0.01 mass % to 10 mass %, the content ratio of the second material is in a range from 1 mass % to 75 mass %, and the content ratio of the third material is in a range from 1 mass % to 75 mass %. An upper limit of the total of the respective content ratios of the first to third materials in the emitting layer is 100 mass %. It should be noted that the emitting layer of the exemplary embodiment may further contain another material in addition to the first to third materials.

Substrate

A substrate is used as a support for the organic EL device. For instance, glass, quartz, plastics and the like are usable as the substrate. A flexible substrate is also usable. The flexible substrate is a bendable substrate, which is exemplified by a plastic substrate formed of polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, alloy, an electrically conductive compound and a mixture thereof, which have a large work function, specifically, of 4.0 eV or more, is preferably usable as the anode formed on the substrate. Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), or nitrides of a metal material (e.g., titanium nitride) are usable.

The above materials are typically deposited as a film by sputtering. For instance, indium zinc oxide can be deposited as a film by sputtering using a target that is obtained by adding zinc oxide in a range from 1 mass % to 10 mass % to indium oxide. Moreover, for instance, indium oxide containing tungsten oxide and zinc oxide can be deposited as a film by sputtering using a target that is obtained by adding tungsten oxide in a range from 0.5 mass % to 5 mass % and zinc oxide in a range from 0.1 mass % to 1 mass % to indium oxide. In addition, vapor deposition, coating, ink jet printing, spin coating and the like may be used for forming a film.

Among EL layers formed on the anode, a hole injecting layer formed adjacent to the anode is formed of a composite material that facilitates injection of holes irrespective of the work function of the anode. Accordingly, a material usable as an electrode material (e.g., metal, alloy, an electrically conductive compound, a mixture thereof, and elements belonging to Groups 1 and 2 of the periodic table of the elements) is usable as the material for the anode.

The elements belonging to Groups 1 and 2 of the periodic table of the elements, which are materials having a small work function, namely, an alkali metal such as lithium (Li) and cesium (Cs) and an alkaline earth metal such as magnesium (Mg), calcium (Ca) and strontium (Sr), alloy thereof (e.g., MgAg, AlLi), a rare earth metal such as europium (Eu) and ytterbium (Yb), and alloy thereof are also usable as the material for the anode. When the anode is formed of the alkali metal, alkaline earth metal and alloy thereof, vapor deposition and sputtering are usable. Further, when the anode is formed of silver paste and the like, coating, ink jet printing and the like are usable.

Cathode

Metal, alloy, an electrically conductive compound, a mixture thereof and the like, which have a small work function, specifically, of 3.8 eV or less, is preferably usable as a material for the cathode. Specific examples of the material for the cathode include: the elements belonging to Groups 1 and 2 of the periodic table of the elements, namely, an alkali metal such as lithium (Li) and cesium (Cs) and an alkaline earth metal such as magnesium (Mg), calcium (Ca) and strontium (Sr); alloy thereof (e.g., MgAg, AlLi); a rare earth metal such as europium (Eu) and ytterbium (Yb); and alloy thereof.

When the cathode is formed of the alkali metal, alkaline earth metal and alloy thereof, vapor deposition and sputtering are usable. Moreover, when the anode is formed of silver paste and the like, coating, ink jet printing and the like are usable.

By providing an electron injecting layer, various conductive materials such as Al, Ag, ITO, graphene and indium tin oxide containing silicon or silicon oxide are usable for forming the cathode irrespective of the magnitude of the work function. The conductive materials can be deposited as a film by sputtering, ink jet printing, spin coating and the like.

Hole Injecting Layer

A hole injecting layer is a layer containing a highly hole-injectable substance. Examples of the highly hole-injectable substance include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f: 20,30-h]quinoxaline-2,3,6,7,10,11-hexacarbonitrile (HAT-CN).

Moreover, a high-molecule compound (e.g., an oligomer, dendrimer and polymer) is also usable as the highly hole-injectable substance. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamido] (abbreviation: PTPDMA), and poly[N,N'-bis(4-butylphenyl)-N,N'-bis(phenyl)benzidine] (abbreviation: Poly-TPD). Furthermore, the examples of the high-molecule compound include a high-molecule compound added with an acid such as poly(3,4-ethylene dioxythiophene)/poly(styrene sulfonic acid) (PEDOT/PSS), and polyaniline/poly(styrene sulfonic acid) (PAni/PSS).

Hole Transporting Layer

A hole transporting layer is a layer containing a highly hole-transportable substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

A hole transporting layer is a layer containing a highly hole-transportable substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

However, any substance having a hole transporting performance higher than an electron transporting performance may be used in addition to the above substances. A highly hole-transportable substance may be provided in the form of a single layer or a laminated layer of two or more layers of the above substance.

When the hole transporting layer includes two or more layers, one of the layers with a larger energy gap is preferably provided closer to the emitting layer. Examples of such a material include HT-2, which is used in Examples described later.

Electron Transporting Layer

An electron transporting layer is a layer containing a highly electron-transportable substance. As the electron transporting layer, 1) a metal complex such as an aluminum complex, beryllium complex and zinc complex, 2) heteroaromatic compound such as an imidazole derivative, benzimidazole derivative, azine derivative, carbazole derivative, and phenanthroline derivative, and 3) a high-molecule compound are usable. Specifically, as a low-molecule organic compound, a metal complex such as Alq, tris(4-methyl-8-quinolinato)aluminum (abbreviation: Almq3), bis(10-hydroxybenzo[h]quinolinato)beryllium (abbreviation: BeBq2), BAlq, Znq, ZnPBO and ZnBTZ are usable. In addition to the metal complex, a heteroaromatic compound such as 2-(4-biphenyl)-5-(4-tert-butylphenyl)-1,3,4-oxadiazole (abbreviation: PBD), 1,3-bis[5-(ptert-butyl-phenyl)-1,3,4-oxadiazole-2-yl]benzene (abbreviation: OXD-7), 3-(4-tert-butylphenyl)-4-phenyl-5-(4-biphenyl)-1,2,4-triazole (abbreviation: TAZ), 3-(4-tert-butylphenyl)-4-(4-ethylphenyl)-5-(4-biphenyl)-1,2,4-triazole (abbreviation: p-EtTAZ), bathophenanthroline (abbreviation: BPhen), bathocuproine (abbreviation: BCP), and 4,4'-bis(5-methyl-benzoxazole-2-yl)stilbene (abbreviation: BzOs) are usable. In the exemplary embodiment, a benzimidazole compound is suitably usable. The above-described substances mostly have an electron mobility of $10^{-6}$ cm$^2$/(V·s) or more. However, any substance having an electron transporting performance higher than a hole transporting performance may be used for the electron transporting layer in addition to the above substances. The electron transporting layer may be provided in the form of a single layer or a laminated layer of two or more layers of the above substance(s).

Moreover, a high-molecule compound is also usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

An electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF2), and lithium oxide (LiOx). In addition, a compound containing an alkali metal, alkaline earth metal and a compound thereof in the electron transportable substance, specifically, a compound containing magnesium (Mg) in Alq and the like may be used. With this compound, electrons can be more efficiently injected from the cathode.

Alternatively, a composite material provided by mixing an organic compound with an electron donor may be used for the electron injecting layer. The composite material exhibits excellent electron injecting performance and electron transporting performance since the electron donor generates electron in the organic compound. In this arrangement, the organic compound is preferably a material exhibiting an excellent transforming performance of the generated electrons. Specifically, for instance, the above-described substance for the electron transporting layer (e.g., the metal complex and heteroaromatic compound) is usable. The electron donor may be any substance exhibiting an electron donating performance to the organic compound. Specifically, an alkali metal, alkaline earth metal and a rare earth metal are preferable, examples of which include lithium, cesium, magnesium, calcium, erbium and ytterbium. Moreover, an alkali metal oxide and alkaline earth metal oxide are preferable, examples of which include lithium oxide, calcium oxide, and barium oxide. Further, Lewis base such as magnesium oxide is also usable. Furthermore, tetrathiafulvalene (abbreviation: TTF) is also usable.

Layer Formation Method(s)

A method for forming each layer of the organic EL device is subject to no limitation except for the above particular description. However, known methods of dry film-forming such as vacuum deposition, sputtering, plasma or ion plating and wet film-forming such as spin coating, dipping, flow coating or ink jet are applicable.

Film Thickness

The thickness of each organic layer of the organic EL device in the exemplary embodiment is subject to no limitation except for the thickness particularly described above. However, the thickness is typically preferably in a range of several nanometers to 1 µm because an excessively thin film is likely to entail defects such as a pin hole while an excessively thick film requires high applied voltage and deteriorates efficiency.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, the "ring carbon atoms" do not include carbon(s) contained in the substituent. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When the benzene ring and/or the naphthalene ring is substituted by, for instance, an alkyl group, the number of carbon atoms of the alkyl group is not included in the number of the ring carbon atoms. When a fluorene ring is substituted by, for instance, a fluorene ring (e.g., a spirofluorene ring), the number of carbon atoms of the fluorene ring as a substituent is not counted in the number of the ring carbon atoms for the fluorene ring.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., a hydrogen atom for terminating the atoms forming the ring) and atoms included in a substituent substituting the ring are not counted in the number of the ring atoms. Unless specifically described, the same applies to the "ring atoms" described later. For instance, a pyridine ring has 6 ring atoms, a quinazoline ring has 10 ring atoms, and a furan ring has 5 ring atoms. Hydrogen atoms respectively bonded to the pyridine ring and the quinazoline ring and atoms forming the substituents are not counted in the number of the ring atoms. When a fluorene ring is substituted by, for instance, a fluorene ring (e.g., a spirofluorene ring), the number of atoms of the fluorene ring as a substituent is not included in the number of the ring atoms for the fluorene ring.

Next, each of substituents described in the above formulae will be described.

In the exemplary embodiment, examples of the aromatic hydrocarbon group group having 6 to 30 ring carbon atoms include a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, and more preferably 6 to 12 ring carbon atoms. Among the above aryl group, a phenyl group, biphenyl group, naphthyl group, phenanthryl group, terphenyl group, and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms later described in the exemplary embodiment.

The heterocyclic group (occasionally, referred to as heteroaryl group, heteroaromatic ring group or aromatic heterocyclic group) having 5 to 30 ring atoms preferably contains at least one atom selected from the group consisting of nitrogen, sulfur, oxygen, silicon, selenium atom and germanium atom, and more preferably contains at least one atom selected from the group consisting of nitrogen, sulfur and oxygen.

Examples of the heterocyclic group (heteroaryl group) having 5 to 30 ring atoms in the exemplary embodiment include a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazolyl group is preferably substituted by a substituted or unsubstituted aryl group having 6 to 30 ring carbon atoms or a substituted or unsubstituted heterocyclic group having 5 to 30 ring atoms in the exemplary embodiment.

In the exemplary embodiment, the heterocyclic group may be a group derived from any one of moieties represented by formulae (XY-1) to (XY-18).

[Formula 63]

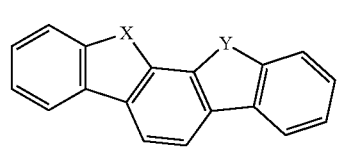

(XY-1)

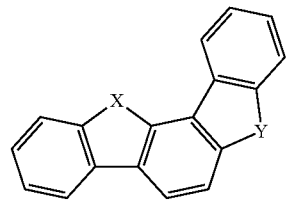

(XY-2)

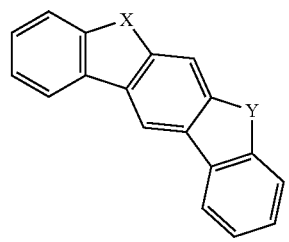

(XY-3)

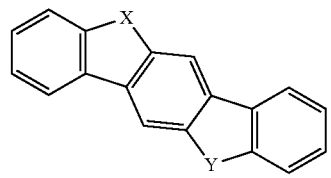

(XY-4)

-continued (XY-5) 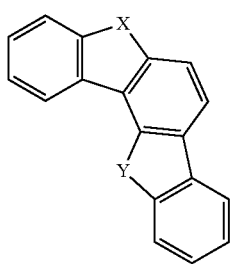

(XY-6) 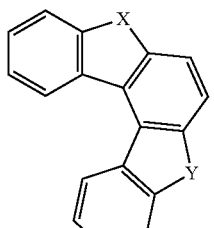

[Formula 64]

(XY-7) 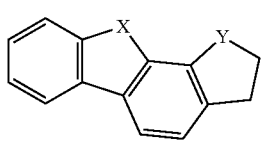

(XY-8) 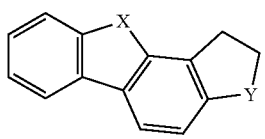

(XY-9) 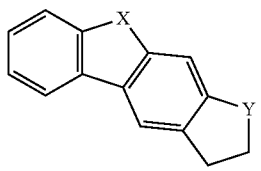

(XY-10) 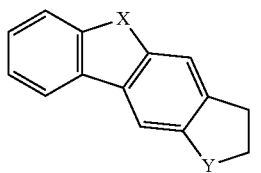

(XY-11) 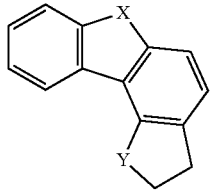

(XY-12) 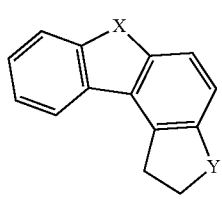

[Formula 65]

(XY-13) 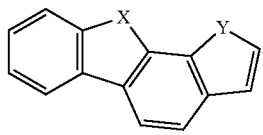

(XY-14) 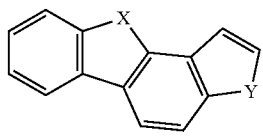

(XY-15) 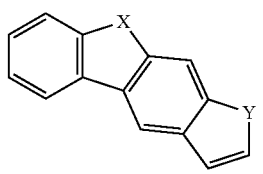

(XY-16) 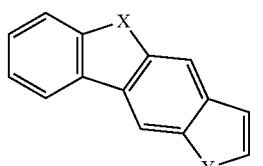

(XY-17) 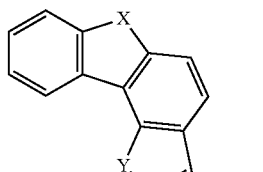

(XY-18) 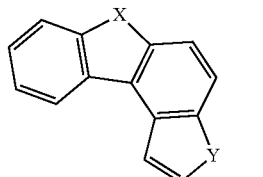

In the formulae (XY-1) to (XY-18), X and Y each independently represent a hetero atom, and preferably represent an oxygen atom, sulfur atom, selenium atom, silicon atom or germanium atom. The moieties represented by the formulae (XY-1) to (XY-18) may each be bonded in any position to be a heterocyclic group, which may be substituted.

In the exemplary embodiment, examples of the substituted or unsubstituted carbazolyl group may include a group in which a carbazole ring is further fused with a ring(s) as shown in the following formulae. Such a group may be substituted. The group may be bonded in any position as desired.

[Formula 66]

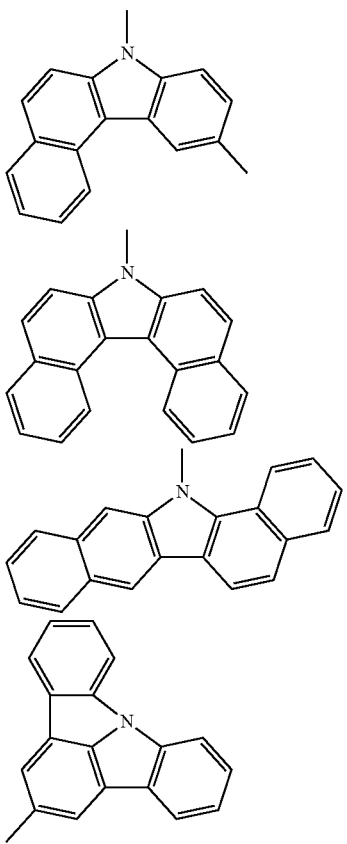

The alkyl group having 1 to 30 carbon atoms in the exemplary embodiment is preferably linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group, and neopentyl group are particularly preferable.

Examples of the cycloalkyl group in the exemplary embodiment include a cyclopropyl group, cyclobutyl group, cyclopentyl group, cyclohexyl group, 4-methylcyclohexyl group, adamantyl group and norbornyl group. The cycloalkyl group preferably has 3 to 10 ring carbon atoms, more preferably 5 to 8 ring carbon atoms. Among the above cycloalkyl group, a cyclopentyl group and a cyclohexyl group are particularly preferable.

A halogenated alkyl group provided by substituting the alkyl group with a halogen atom is exemplified by a halogenated alkyl group provided by substituting the alkyl group having 1 to 30 carbon atoms with one or more halogen groups. Specific examples of the halogenated alkyl group includes a fluoromethyl group, difluoromethyl group, trifluoromethyl group, fluoroethyl group, trifluoromethylmethyl group, trifluoroethyl group, and pentafluoroethyl group.

The alkylsilyl group having 3 to 30 carbon atoms in the exemplary embodiment is exemplified by a trialkylsilyl group having the above alkyl group having 1 to 30 carbon atoms. Specific examples of the trialkylsilyl group include a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups in the trialkylsilyl group may be mutually the same or different.

Examples of the arylsilyl group having 6 to 30 ring carbon atoms in the exemplary embodiment include a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the aryl group having 6 to 30 ring carbon atoms. The dialkylarylsilyl group preferably has 8 to 30 carbon atoms.

The alkyldiarylsilyl group is exemplified by an alkyldiarylsilyl group having one of the examples of the alkyl group having 1 to 30 carbon atoms and two of the aryl group having 6 to 30 ring carbon atoms. The dialkylarylsilyl group preferably has 13 to 30 carbon atoms.

The triarylsilyl group is exemplified by a triarylsilyl group having three of the aryl group having 6 to 30 ring carbon atoms. The triarylsilyl group preferably has 18 to 30 carbon atoms.

The alkoxy group having 1 to 30 carbon atoms in the exemplary embodiment is represented by —$OZ_1$. $Z_1$ is exemplified by the above alkyl group having 1 to 30 carbon atoms. Examples of the alkoxy group include a methoxy group, ethoxy group, propoxy group, butoxy group, pentyloxy group and hexyloxy group. The alkoxy group preferably has 1 to 20 carbon atoms.

A halogenated alkoxy group provided by substituting the alkoxy group with a halogen atom is exemplified by a halogenated alkoxy group provided by substituting the alkoxy group having 1 to 30 carbon atoms with one or more halogen groups.

The aryloxy group having 6 to 30 ring carbon atoms in the exemplary embodiment is represented by —$OZ_2$. $Z_2$ is exemplified by the above aryl group having 6 to 30 ring carbon atoms. The aryloxy group preferably has 6 to 20 ring carbon atoms. The aryloxy group is exemplified by a phenoxy group.

The alkylamino group having 2 to 30 carbon atoms is represented by —$NHR_V$ or —$N(R_V)_2$. $R_V$ is exemplified by the alkyl group having 1 to 30 carbon atoms.

The arylamino group having 6 to 60 ring carbon atoms is represented by —$NHR_W$ or —$N(R_W)_2$. $R_W$ is exemplified by the above aryl group having 6 to 30 ring carbon atoms.

The alkylthio group having 1 to 30 carbon atoms is represented by —$SR_V$. $R_V$ is exemplified by the alkyl group having 1 to 30 carbon atoms. The alkylthio group preferably has 1 to 20 carbon atoms.

The arylthio group having 6 to 30 ring carbon atoms is represented by —$SR_W$. $R_W$ is exemplified by the above aryl group having 6 to 30 ring carbon atoms. The arylthio group preferably has 6 to 20 ring carbon atoms.

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

Herein, a "hydrogen atom" means isotopes having different neutron numbers and specifically encompasses protium, deuterium and tritium.

Herein, examples of substituents in the exemplary embodiment, such as the substituent meant by "substituted or unsubstituted" and the substituent in the cyclic structures A, B, E, F and G, are an alkenyl group, alkynyl group, aralkyl group, halogen atom, cyano group, hydroxyl group, nitro group and carboxy group, in addition to the above-described aryl group, heterocyclic group, alkyl group (linear or branched alkyl group, cycloalkyl group and haloalkyl group), alkylsilyl group, arylsilyl group, alkoxy group, aryloxy group, alkylamino group, arylamino group, alkylthio group, and arylthio group.

In the above-described substituents, the aryl group, heterocyclic group, alkyl group, halogen atom, alkylsilyl group, arylsilyl group and cyano group are preferable. The preferable ones of the specific examples of each substituent are further preferable.

These substituents may be further substituted by the above substituent(s). In addition, plural ones of these substituents may be mutually bonded to form a ring.

The alkenyl group is preferably an alkenyl group having 2 to 30 carbon atoms, which may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group, and cyclohexadienyl group.

The alkynyl group is preferably an alkynyl group having 2 to 30 carbon atoms, which may be linear, branched or cyclic. Examples of the alkynyl group include ethynyl, propynyl, and 2-phenylethynyl.

The aralkyl group is preferably an aralkyl group having 6 to 30 ring carbon atoms and is represented by —$Z_3$-$Z_4$. $Z_3$ is exemplified by an alkylene group derived from the above alkyl group having 1 to 30 carbon atoms. $Z_4$ is exemplified by the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group include a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Examples of the halogen atom include a fluorine atom, chlorine atom, bromine torn and iodine atom, among which a fluorine atom is preferable.

"Unsubstituted" in "substituted or unsubstituted" herein means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX." "XX" and "YY" each mean an integer of 1 or more.

Herein, "XX to YY atoms" in the description of "substituted or unsubstituted ZZ group having XX to YY atoms" represent atoms of an unsubstituted ZZ group and does not include atoms of a substituent(s) of the substituted ZZ group. Herein, "YY" is larger than "XX." "XX" and "YY" each mean an integer of 1 or more.

The same description as the above applies to "substituted or unsubstituted" in the following compound or a partial structure thereof.

Herein, examples of the multiple linking group including bonded 2 to 4 groups selected from the above aromatic hydrocarbon groups, the multiple linking group including bonded 2 to 4 groups selected from the above heterocyclic groups, or the multiple linking group including bonded 2 to 4 groups selected from the above aromatic hydrocarbon groups and heterocyclic groups include a divalent group including bonded two or four groups selected from the above aromatic hydrocarbon groups and heterocyclic groups. Examples of the multiple linking group including 2 to 4 groups selected from the above aromatic hydrocarbon groups and heterocyclic groups include a heterocyclic group-aromatic hydrocarbon group, aromatic hydrocarbon group-heterocyclic group, aromatic hydrocarbon group-heterocyclic group-aromatic hydrocarbon group, heterocyclic group-aromatic hydrocarbon group-heterocyclic group, aromatic hydrocarbon group-heterocyclic group-aromatic hydrocarbon group-heterocyclic group, and heterocyclic group-aromatic hydrocarbon group-heterocyclic group-aromatic hydrocarbon group. Among the above, divalent groups including one of the above aromatic hydrocarbon groups and one of the above heterocyclic groups, i.e., heterocyclic group-aromatic hydrocarbon group and aromatic hydrocarbon group-heterocyclic group, are preferable. It should be noted that specific examples of the aromatic hydrocarbon group and the heterocyclic group in the multiple linking group include the above groups described as the aromatic hydrocarbon group and the heterocyclic group.

The organic EL device of the exemplary embodiment is usable in an electronic device. Examples of the electronic device include a display unit and a light-emitting unit. Examples of the display unit include display components such as en organic EL panel module, TV, mobile phone, tablet, and personal computer. Examples of the light-emitting unit include an illuminator and a vehicle light.

Modifications of Embodiment(s)

It should be noted that the invention is not limited to the exemplary embodiment. The invention may include any modification and improvement compatible with the invention.

The emitting layer is not limited to a single layer, but may be provided as laminate by a plurality of emitting layers. When the organic EL device includes a plurality of emitting layers, it is only required that at least one of the emitting layers includes the first to third materials. The other emitting layers may each be a fluorescent emitting layer, or a phosphorescent emitting layer that emits light through direct electron transfer from triplet state to ground state.

When the organic EL device includes the plurality of emitting layers, the plurality of emitting layers may be adjacent to each other or a so-called tandem organic EL device in which a plurality of emitting units are laminated through an intermediate layer.

For instance, a blocking layer may be provided in contact with an anode-side or a cathode-side of the emitting layer. The blocking layer is preferably provided in contact with the emitting layer to block at least either of excitons and exciplexes.

In contrast, when the blocking layer is provided in contact with the cathode-side of the emitting layer, the blocking layer permits transport of electrons, but prevents holes from reaching a layer provided near the cathode (e.g., the electron transporting layer) beyond the blocking layer.

For instance, when the blocking layer is provided in contact with the anode-side of the emitting layer, the blocking layer permits transport of holes, but prevents electrons from reaching a layer provided near the anode (e.g., the electron transporting layer) beyond the blocking layer.

Further, a blocking layer may be provided in contact with the emitting layer to prevent an excitation energy from leaking from the emitting layer into a layer in the vicinity thereof. Excitons generated in the emitting layer are prevented from moving into a layer provided near the electrode (e.g., an electron transporting layer and a hole transporting layer) beyond the blocking layer.

The emitting layer and the blocking layer are preferably bonded to each other.

Further, specific arrangements and configurations for practicing the invention may be altered to other arrangements and configurations compatible with the invention.

EXAMPLE(S)

Examples of the invention will be described below. However, the invention is not limited to Examples.

Compounds used in Examples are as follows.

[Formula 67]

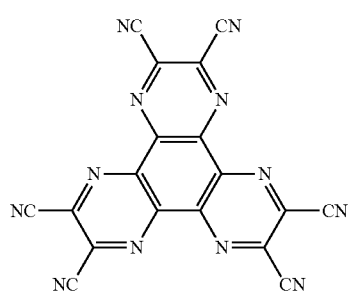

HI

HT-1

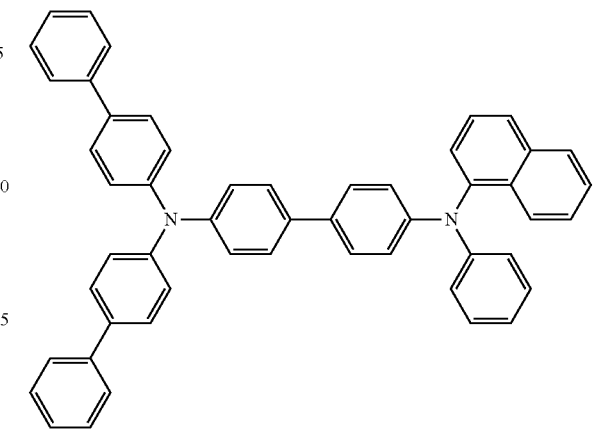

-continued

HT-2

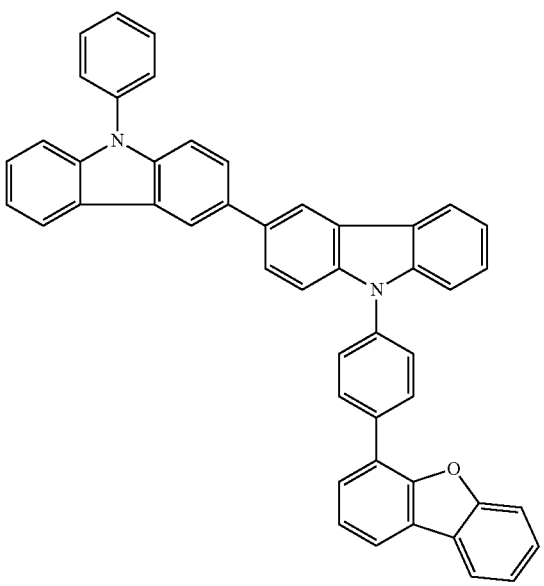

[Formula 68]

MT-1

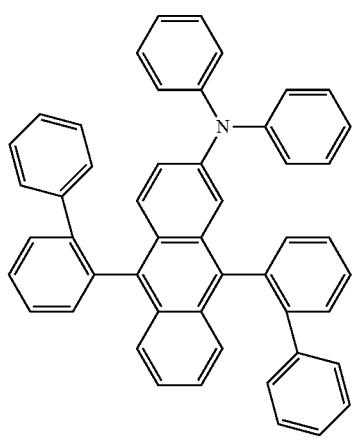

-continued

MT-2

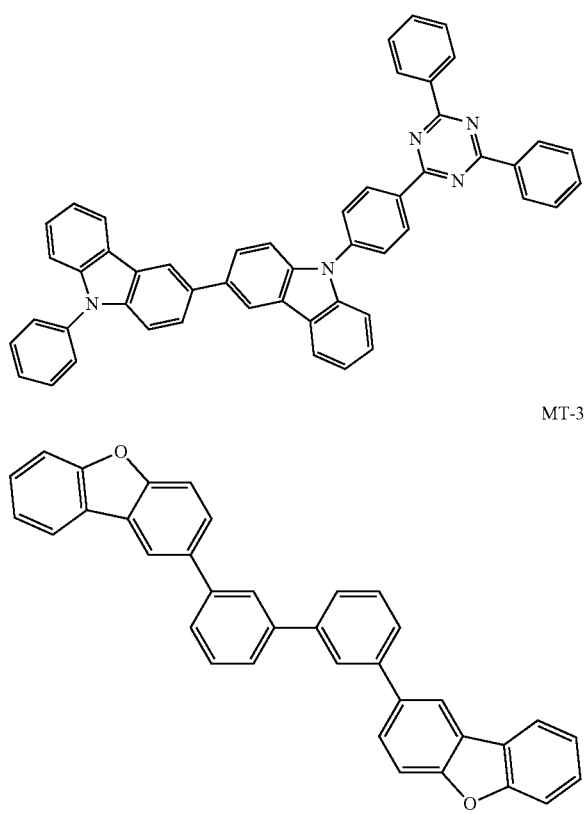

MT-3

[Formula 69]

HB-1

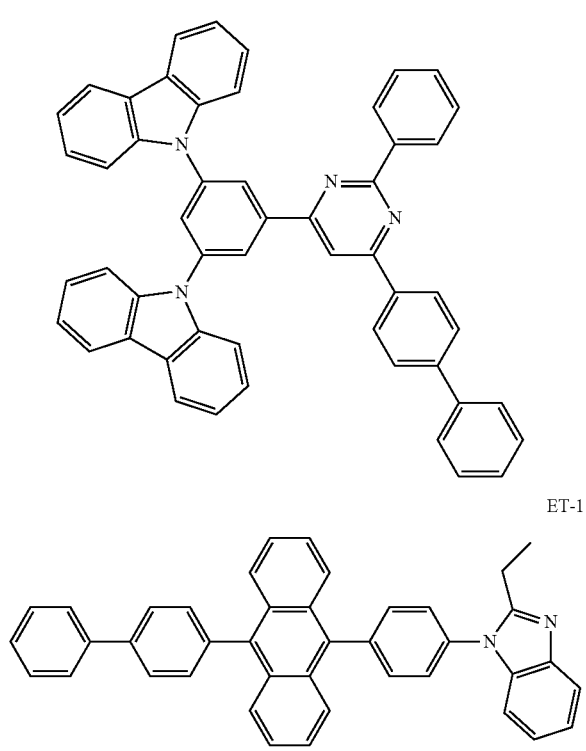

ET-1

Evaluation of Compounds

Next, properties of the compounds used in Examples were measured. A measurement method and a calculation method are described below. Measurement results and calculation results are shown in Table 5.

Singlet Energy EgS

The singlet energy EgS was measured as follows.

A 10-μmol/L toluene solution of a compound to be measured was prepared and put in a quartz cell. An absorption spectrum (ordinate axis: luminous intensity, abscissa axis: intensity) of the thus-obtained sample was measured at a room temperature (300 K). A tangent was drawn at the rise on the long-wavelength side, and a singlet energy was calculated by substituting a wavelength value $\lambda_{edge}$ [nm] of an intersection between the tangent and the abscissa axis into the following conversion equation 3.

$$EgS \text{ [eV]} = 1239.85/\lambda_{edge} \quad \text{Conversion Equation 3:}$$

In Example, the absorption spectrum was measured using a spectrophotometer manufactured by Hitachi, Ltd. (device name: U3310).

The tangent to the fall of the absorption spectrum on the long-wavelength side was drawn as follows. While moving on a curve of the absorption spectrum from the maximum spectral value closest to the long-wavelength side in a long-wavelength direction, a tangent at each point on the curve was checked. An inclination of the tangent was decreased and increased in a repeated manner as the curve fell (i.e., a value of the ordinate axis was decreased). A tangent drawn at a point of the minimum inclination closest to the long-wavelength side (except when absorbance was 0.1 or less) was defined as the tangent to the fall of the absorption spectrum on the long-wavelength side.

The maximum absorbance of 0.2 or less was not included in the above-mentioned maximum absorbance on the long-wavelength side.

Energy Gap $Eg_{77K}$ at 77 [K]

For the first material and the third material (measurement targets), the triplet energy was measured as follows. The compound MT-1 and the compound MT-3 were to be measured. The compound to be measured was dissolved in EPA (diethylether:isopentane:ethanol=5:5:2 in volume ratio) at a concentration of 10 μmol/L, and the resulting solution was set in a quartz cell to provide a measurement sample. A phosphorescence spectrum (ordinate axis: phosphorescent luminous intensity, abscissa axis: wavelength) of the measurement sample was measured at a low temperature (77 [K]), a tangent was drawn at the rise of the phosphorescence spectrum on the short-wavelength side, and an energy amount calculated by the following conversion equation 1 based on a wavelength value $\lambda_{edge}$ [nm] of an intersection between the tangent and the abscissa axis was defined as the energy gap $Eg_{77K}$ at 77 [K].

$$Eg_{77K} \text{ [eV]} = 1239.85/\lambda_{edge} \quad \text{Conversion Equation 1:}$$

For the second material (measurement target), the triplet energy was measured as follows. The compound MT-2 was to be measured. The compound to be measured (the second material) and the compound TH-2 were co-deposited on a quartz substrate to prepare a sample sealed in an NMR tube. It should be noted that the sample was prepared under the following conditions: quartz substrate/TH-2: second material (film thickness: 100 nm, concentration of second material: 12 mass %).

A phosphorescence spectrum (ordinate axis: phosphorescent luminous intensity, abscissa axis: wavelength) of the measurement sample was measured at a low temperature (77 [K]), a tangent was drawn at the rise of the phosphorescence spectrum on the short-wavelength side, and an energy amount calculated by the following conversion equation 2 based on a wavelength value $\lambda_{edge}$ [nm] of an intersection between the tangent and the abscissa axis was defined as the energy gap $Eg_{77K}$ at 77 [K].

$$Eg_{77K}[eV]=1239.85/\lambda_{edge} \qquad \text{Conversion Equation 2:}$$

For phosphorescence measurement, a spectrophotofluorometer body F-4500 (manufactured by Hitachi High-Technologies Corporation) was used.

The tangent to the rise of the phosphorescence spectrum on the short-wavelength side was drawn as follows. While moving on a curve of the phosphorescence spectrum from the short-wavelength side to the maximum spectral value closest to the short-wavelength side among the maximum spectral values, a tangent was checked at each point on the curve toward the long-wavelength of the phosphorescence spectrum. An inclination of the tangent was increased as the curve rose (i.e., a value of the ordinate axis was increased). A tangent drawn at a point of the maximum inclination (i.e., a tangent at an inflection point) was defined as the tangent to the rise of the phosphorescence spectrum on the short-wavelength side.

The maximum with peak intensity being 15% or less of the maximum peak intensity of the spectrum was not included in the above-mentioned maximum closest to the short-wavelength side of the spectrum. The tangent drawn at a point of the maximum spectral value being the closest to the short-wavelength side and having the maximum inclination was defined as a tangent to the rise of the phosphorescence spectrum on the short-wavelength side.

For phosphorescence measurement, a spectrophotofluorometer body F-4500 (manufactured by Hitachi High-Technologies Corporation) was used.

Ionization Potential

A photoelectron spectroscopy device (AC-3, manufactured by Riken Keiki Co., Ltd.) was used for the measurement of an ionization potential under atmosphere. Specifically, a compound to be measured was irradiated with light and the amount of electrons generated by charge separation was measured.

Affinity (Electron Affinity)

The electron affinity was calculated by the following numerical formula from the measurement values of the ionization potential Ip and singlet energy EgS of the compound measured in the above manner.

$$Af=Ip-EgS$$

Delayed Fluorescence

Occurrence of delayed fluorescence emission was determined by measuring transient photoluminescence (PL) using a device shown in FIG. 2. A sample was prepared by co-depositing the compounds MT-2 and TH-2 on a quartz substrate at a ratio of the compound MT-2 of 12 mass % to form a 100-nm-thick thin film.

Delayed fluorescence emission can be obtained using the device shown in FIG. 2. There are two types of emission: Prompt emission observed immediately when the excited state is achieved by exciting the compound MT-2 with a pulse beam (i.e., a beam emitted from a pulse laser) having an absorbable wavelength; and Delay emission observed not immediately when but after the excited state is achieved. In Examples, occurrence of delayed fluorescence emission is determined when the amount of Delay emission is 5% or more relative to the amount of Prompt emission. The amount of Delay emission of the compound MT-2 has been found to be 5% or more relative to the amount of Prompt emission.

The amount of Prompt emission and the amount of Delay emission can be obtained in the same method as a method described in "Nature 492, 234-238, 2012." It should be noted that the amount of Prompt emission and the amount of Delay emission may be calculated using a device different from the device shown in FIG. 2 and the device described in Reference Literature 1.

TABLE 5

| Compound | Singlet Energy EgS [eV] | Energy Gap $Eg_{77K}$ [eV] | Ionization Potential Ip [eV] | Affinity Af [eV] |
| --- | --- | --- | --- | --- |
| MT-1 | 2.58 | 1.80 | — | — |
| MT-2 | 2.91 | 2.72 | 5.68 | 2.77 |
| MT-3 | 3.55 | 2.92 | 6.45 | 2.90 |

Preparation and Evaluation of Organic EL Device

The organic EL device was manufactured and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130-nm thick.

After the glass substrate having the transparent electrode line was cleaned, the glass substrate was mounted on a substrate holder of a vacuum evaporation apparatus. Initially, a compound HI was vapor-deposited on a surface of the glass substrate where the transparent electrode line was provided in a manner to cover the transparent electrode, thereby forming a 5-nm-thick hole injecting layer.

Subsequently, the compound HT-1 was vapor-deposited on the hole injecting layer to form an 80-nm-thick first hole transporting layer on the HI film.

Next, the compound HT-2 was vapor-deposited on the first hole transporting layer to form a 15-nm-thick second hole transporting layer.

Further, on the second hole transporting layer, the compound MT-1 (the first material), the compound MT-2 (the second material) and the compound MT-3 (the third material) were co-deposited to form a 25-nm-thick emitting layer. In the emitting layer, the respective concentrations of the compounds MT-1, MT-2 and MT-3 were 1 mass %, 50 mass % and 49 mass %.

The compound HB-1 was then vapor-deposited on the emitting layer to form a 5-nm-thick blocking layer.

The compound ET-1 was then vapor-deposited on the blocking layer to form a 20-nm-thick electron transporting layer.

Lithium fluoride (LiF) was then vapor-deposited on the electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 1 is roughly shown as follows.

ITO(130)/HI(5)/HT-1(80)/HT-2(15)/MT-1: MT-2: MT-3 (25, 1%: 50%: 49%)/HB-1(5)/ET-1(20)/LiF(1)/Al(80)

Numerals in parentheses represent a film thickness (unit: nm). The numerals in the form of percentage in parentheses indicate ratios (mass %) of the materials in the emitting layer.

Comparative Example 1

An organic EL device of Comparative Example 1 was manufactured in the same manner as the organic EL device of Example 1 except that the organic EL device included a 20-nm-thick emitting layer prepared by co-depositing the compound MT-1 (the first material) and the compound MT-2 (the second material) in place of the emitting layer of Example 1. In the emitting layer of the organic EL device of Comparative Example 1, the respective concentrations of the compounds MT-1 and MT-2 were 1 mass % and 99 mass %.

A device arrangement of the organic EL device of Comparative Example 1 is roughly shown as follows.

ITO(130)/HI(5)/HT-1(80)/HT-2(15)/MT-1: MT-2(25, 1%: 99%)/HB-1(5)/ET-1(20)/LiF(1)/Al(80)

Evaluation of Organic EL Devices

The manufactured organic EL devices of Example 1 and Comparative Example 1 were evaluated as follows. The results are shown in Table 6.

Drive Voltage

Voltage was applied between the ITO transparent electrode and the metal Al cathode such that the current density was 0.1 mA/cm$^2$, 1 mA/cm$^2$ or 10 mA/cm$^2$, where voltage (unit: V) was measured.

Luminance and CIE1931 Chromaticity

Voltage was applied on each of the organic EL devices such that the current density was 0.1 mA/cm$^2$, 1 mA/cm$^2$ or 10 mA/cm$^2$, where luminance and CIE1931 chromaticity coordinates (x, y) were measured using a spectroradiometer CS-1000 (manufactured by Konica Minolta, Inc.).

Current Efficiency L/J and Electrical Power Efficiency η

Voltage was applied on each of the organic EL devices such that the current density was 0.1 mA/cm$^2$, 1 mA/cm$^2$ or 10 mA/cm$^2$, where spectral radiance spectra were measured by the aforementioned spectroradiometer. Based on the obtained spectral radiance spectra, the current efficiency (unit: cd/A) and the electrical power efficiency η (unit: lm/W) were calculated.

Main Peak Wavelength $\lambda_p$

A main peak wavelength $\lambda_p$ was calculated based on the obtained spectral-radiance spectra.

External Quantum Efficiency EQE

Voltage was applied on each of the organic EL devices such that the current density was 0.1 mA/cm$^2$, 1 mA/cm$^2$ or 10 mA/cm$^2$, where spectral-radiance spectra were measured using the above spectroradiometer. The external quantum efficiency EQE (unit: %) was calculated based on the obtained spectral-radiance spectra, assuming that the spectra were provided under a Lambertian radiation.

TABLE 6

| | Current Density [mA/cm$^2$] | Voltage [V] | Luminance [cd/m$^2$] | Chromaticity x | Chromaticity y | $\lambda$p [nm] | L/J [cd/A] | η [lm/W] | EQE [%] |
|---|---|---|---|---|---|---|---|---|---|
| Ex. 1 | 0.10 | 2.75 | 26.9 | 0.183 | 0.366 | 485 | 26.92 | 30.80 | 12.21 |
| | 1.00 | 3.13 | 228.1 | 0.178 | 0.354 | 484 | 22.81 | 22.91 | 10.58 |
| | 10 | 3.83 | 1654.3 | 0.173 | 0.337 | 484 | 16.54 | 13.56 | 7.93 |
| Comp. 1 | 0.10 | 2.47 | 10.2 | 0.186 | 0.401 | 487 | 10.18 | 12.93 | 4.41 |
| | 1.00 | 2.64 | 127.2 | 0.182 | 0.394 | 487 | 12.72 | 15.13 | 5.58 |
| | 10 | 3.16 | 1297.7 | 0.178 | 0.386 | 485 | 12.98 | 12.90 | 5.77 |

As shown in Table 6, the organic EL device of Example 1 exhibited high current efficiency L/J, electrical power efficiency η and external quantum efficiency EQE irrespective of a current density for driving the organic EL device as compared with the organic EL device of Comparative Example 1. Supposedly, since the organic EL device of Comparative Example 1 included the emitting layer consisting solely of the first and second materials, the luminous efficiency thereof was lowered. The organic EL device of Example 1 included the emitting layer containing the third material in addition to the first and second materials, which supposedly results in improvement in luminous efficiency as compared with that of Comparative Example 1. Further, the organic EL device of Example 1 emitted light with a short wavelength as compared with Comparative Example 1, and emission of a strong-blue light from the organic EL device of Example 1 was observed. This is supposedly attributed to dispersion of the second material. As described above, Example 1 could provide a highly efficient blue-emitting organic EL device.

Next, other organic EL devices were manufactured using the following compounds as well as the compounds used in the above Example and Comparative Example.

[Formula 70]

MT-4

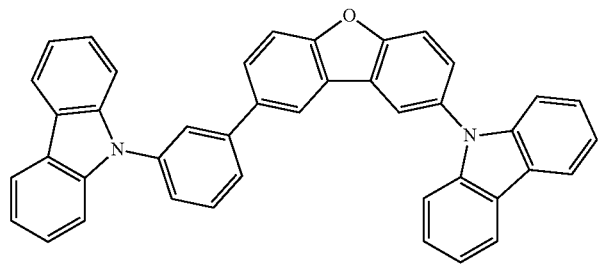

MT-5
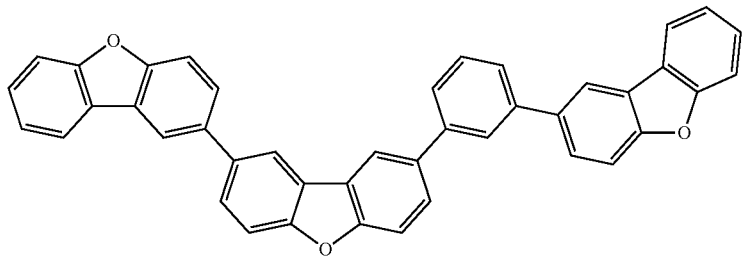
[Formula 71]
MT-6
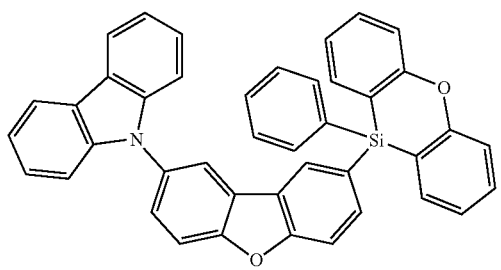
MT-7
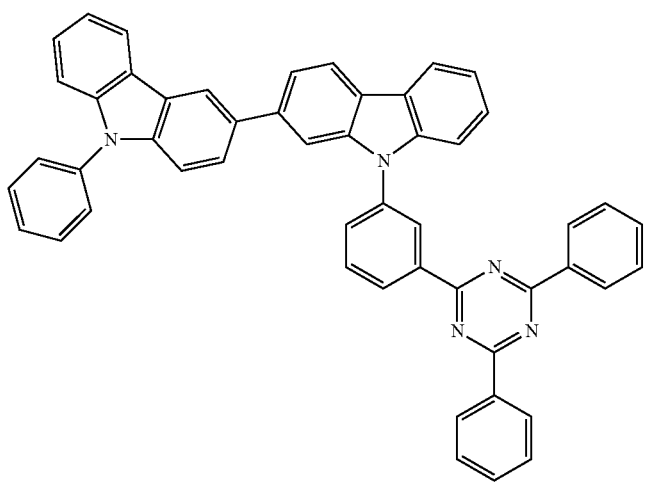
[Formula 72]
MT-8
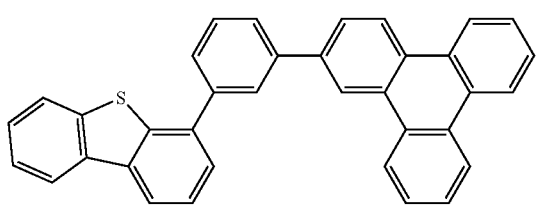
MT-9
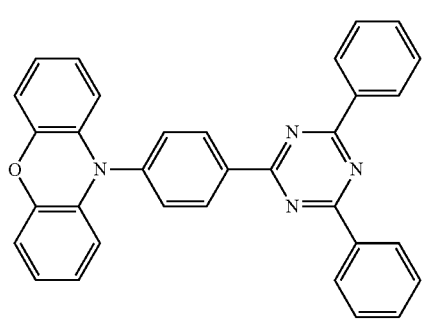

-continued
[Formula 73]
MT-10
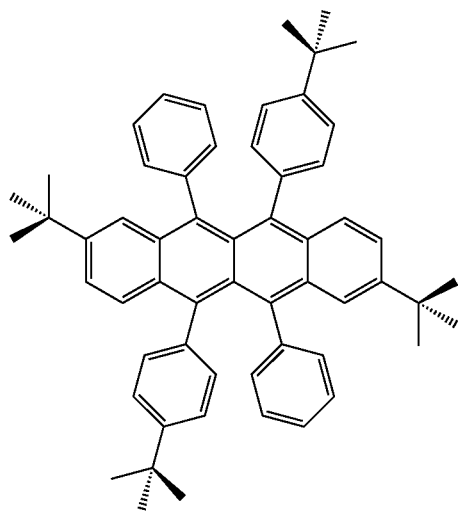
MT-11
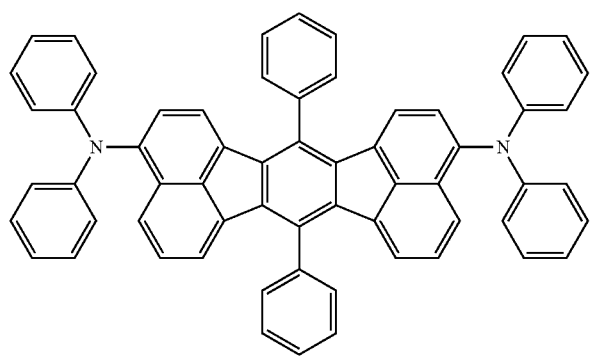
[Formula 74]
MT-12
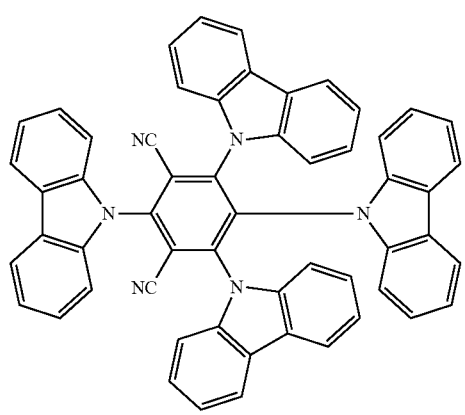
MT-13
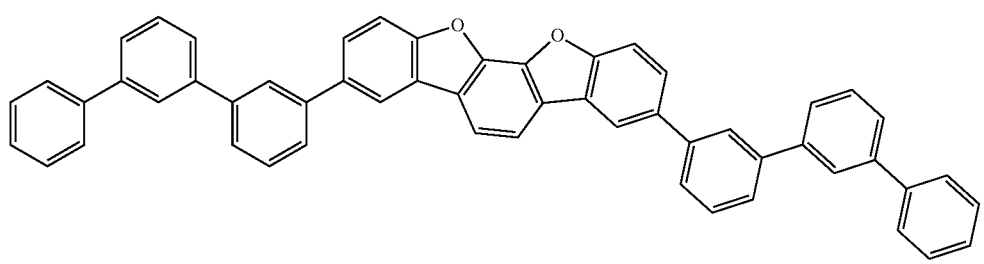

[Formula 75]

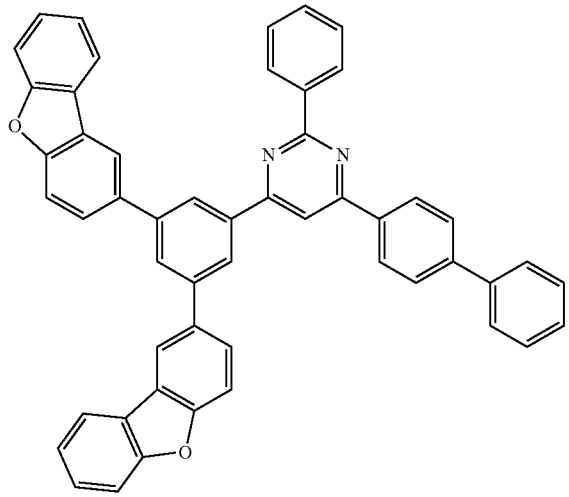
HB-2

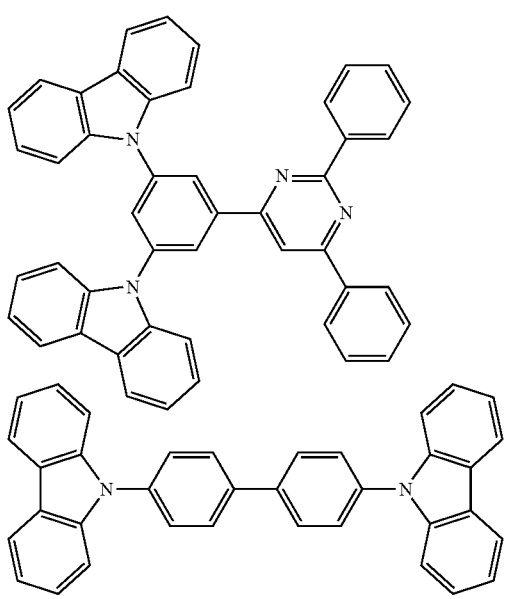
CBP

HB-3

Evaluation of Compounds

Next, properties of the compounds MT-4 to MT-13 were measured. A measurement method and a calculation method are described below. Measurement results and calculation results are shown in Table 7. The measurement method and calculation method were the same as the above. The compounds MT-9 and MT-12 were each a delayed fluorescent compound with the amount of Delay emission of 5% or more relative to that of Prompt emission.

TABLE 7

| Compound | Singlet Energy EgS [eV] | Energy Gap Eg77K [eV] | Ionization Potential Ip [eV] | Affinity Af [eV] |
|---|---|---|---|---|
| MT-4 | 3.54 | 3.03 | 6.04 | 2.50 |
| MT-5 | 3.76 | 2.95 | 6.33 | 2.57 |
| MT-6 | 3.53 | 3.06 | 6.20 | 2.67 |
| MT-7 | 3.41 | 2.73 | 5.58 | 2.17 |
| MT-8 | 3.59 | 2.74 | 6.10 | 2.51 |
| MT-9 | 2.57 | 2.46 | 5.64 | 3.07 |
| MT-10 | 2.23 | — | 5.37 | 3.14 |
| MT-11 | 2.28 | — | 5.61 | 3.33 |
| MT-12 | 2.62 | 2.46 | 5.91 | 3.29 |
| MT-13 | 3.74 | 2.85 | 6.15 | 2.41 |

Example 2

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 70-nm thick.

After the glass substrate having the transparent electrode line was cleaned, the glass substrate was mounted on a substrate holder of a vacuum evaporation apparatus. Initially, a compound HI was vapor-deposited on a surface of the glass substrate where the transparent electrode line was provided in a manner to cover the transparent electrode, thereby forming a 5-nm-thick hole injecting layer.

Subsequently, the compound HT-1 was vapor-deposited on the hole injecting layer to form a 65-nm-thick first hole transporting layer on the HI film The compound HT-2 was then vapor-deposited on the first hole transporting layer to form a 10-nm-thick second hole transporting layer.

Further, on the second hole transporting layer, the compounds MT-4, MT-9 and MT-10 were co-deposited to form a 25-nm-thick emitting layer. In the emitting layer, the respective concentration of the compounds MT-10, MT-9 and MT-4 were 1 mass %, 50 mass % and 49 mass %.

The compound HB-2 was then vapor-deposited on the emitting layer to form a 5-nm-thick blocking layer.

The compound ET-1 was then vapor-deposited on the blocking layer to form a 30-nm-thick electron transporting layer.

Lithium fluoride (LiF) was then vapor-deposited on the electron transporting layer to form a 1-nm-thick electron injecting electrode (cathode).

A metal aluminum (Al) was then vapor-deposited on the electron injecting electrode to form an 80-nm-thick metal Al cathode.

A device arrangement of the organic EL device of Example 2 is roughly shown as follows.

ITO(70)/HI(5)/HT-1(65)/HT-2(10)/MT-4: MT-9: MT-10 (25, 49%: 50%: 1%)/HB-2(5)/ET-1(30)/LiF(1)/Al(80)

Example 3

An organic EL device of Example 3 was manufactured in the same manner as the organic EL device of Example 2 except that the compound MT-6 was used in place of the compound MT-4 in the emitting layer of Example 2. A device arrangement of the organic EL device of Example 3 is roughly shown as follows.

ITO(70)/HI(5)/HT-1(65)/HT-2(10)/MT-6: MT-9: MT-10 (25, 49%: 50%: 1%)/HB-2(5)/ET-1(30)/LiF(1)/Al(80)

Example 4

An organic EL device of Example 4 was manufactured in the same manner as the organic EL device of Example 2 except that the compound MT-5 was used in place of the compound MT-4 in the emitting layer of Example 2. A device arrangement of the organic EL device of Example 4 is roughly shown as follows.

ITO(70)/HI(5)/HT-1(65)/HT-2(10)/MT-5: MT-9: MT-10 (25, 49%: 50%: 1%)/HB-2(5)/ET-1(30)/LiF(1)/Al(80)

Example 5

An organic EL device of Example 5 was manufactured in the same manner as the organic EL device of Example 2 except that the compound MT-7 was used in place of the compound MT-4 in the emitting layer of Example 2. A device arrangement of the organic EL device of Example 5 is roughly shown as follows.

ITO(70)/HI(5)/HT-1(65)/HT-2(10)/MT-7: MT-9: MT-10 (25, 49%: 50%: 1%)/HB-2(5)/ET-1(30)/LiF(1)/Al(80)

Example 6

An organic EL device of Example 6 was manufactured in the same manner as the organic EL device of Example 2 except that the compound MT-8 was used in place of the compound MT-4 in the emitting layer of Example 2. A device arrangement of the organic EL device of Example 6 is roughly shown as follows.

ITO(70)/HI(5)/HT-1(65)/HT-2(10)/MT-8: MT-9: MT-10 (25, 49%: 50%: 1%)/HB-2(5)/ET-1(30)/LiF(1)/Al(80)

Comparative Example 2

An organic EL device of Comparative Example 2 was manufactured in the same manner as the organic EL device of Example 2 except that the organic EL device included a 25-nm-thick emitting layer prepared by co-depositing the compounds MT-9 and MT-10 in place of the emitting layer of Example 2. In the emitting layer of the organic EL device of Comparative Example 2, the respective concentrations of the compounds MT-10 and MT-9 were 1 mass % and 99 mass %. A device arrangement of the organic EL device of Comparative Example 2 is roughly shown as follows.

ITO(70)/HI(5)/HT-1(65)/HT-2(10)/MT-9: MT-10(25, 99%: 1%)/HB-2(5)/ET-1(30)/LiF(1)/Al(80)

Evaluation of Organic EL Devices

The manufactured organic EL devices of Examples 2 to 6 and Comparative 2 were evaluated in the same manner as described above. Evaluation items were drive voltage, luminance, CIE1931 chromaticity, current efficiency L/J, electrical power efficiency η, main peak wavelength λp and external quantum efficiency EQE. The results are shown in Table 8.

TABLE 8

|  | Voltage [V] | Current Density [mA/cm$^2$] | Luminance [cd/m$^2$] | Chromaticity x | Chromaticity y | L/J [cd/A] | η [lm/W] | EQE [%] | λp [nm] |
|---|---|---|---|---|---|---|---|---|---|
| Ex. 2 | 3.76 | 10 | 6138.6 | 0.466 | 0.525 | 61.39 | 51.25 | 18.69 | 560 |
| Ex. 3 | 3.46 | 10 | 6557.7 | 0.469 | 0.523 | 65.58 | 59.46 | 20.11 | 561 |
| Ex. 4 | 3.47 | 10 | 6647.7 | 0.466 | 0.525 | 66.48 | 60.23 | 20.36 | 561 |
| Ex. 5 | 2.96 | 10 | 6749.7 | 0.465 | 0.527 | 67.50 | 71.67 | 20.67 | 560 |
| Ex. 6 | 3.24 | 10 | 5953.7 | 0.470 | 0.523 | 59.54 | 57.79 | 18.49 | 561 |
| Comp. 2 | 2.94 | 10 | 4855.3 | 0.476 | 0.519 | 48.55 | 51.81 | 14.99 | 561 |

As shown in Table 8, the organic EL devices of Examples 2 to 6 were higher in luminous efficiency than the organic EL device of Comparative Example 2. The organic EL device of Comparative Example 2 included the emitting layer consisting solely of the compounds MT-9 and MT-10. As compared with the organic EL device of Comparative Example 2, the organic EL devices of Examples 2 to 6 each included the emitting layer further containing the third material. Specifically, the emitting layers of Examples 2 to 6 respectively contained the compounds MT-4, MT-6, MT-5, MT-7 and MT-8 as the third material. Consequently, the organic EL devices of Examples 2 to 6 were higher in current efficiency and external quantum efficiency than the organic EL device of Comparative Example 2.

Example 7

An organic EL device of Example 7 was manufactured in the same manner as the organic EL device of Example 2 except that the compound HB-3 was used in place of the compound HB-2 in the blocking layer of Example 2. A device arrangement of the organic EL device of Example 7 is roughly shown as follows.
ITO(70)/HI(5)/HT-1(65)/HT-2(10)/MT-4: MT-9: MT-10 (25, 49%: 50%: 1%)/HB-3(5)/ET-1(30)/LiF(1)/Al(80)

Example 8

An organic EL device of Example 8 was manufactured in the same manner as the organic EL device of Example 7 except that the compound MT-6 was used in place of the compound MT-4 in the emitting layer of Example 7. A device arrangement of the organic EL device of Example 8 is roughly shown as follows.
ITO(70)/HI(5)/HT-1(65)/HT-2(10)/MT-6: MT-9: MT-10 (25, 49%: 50%: 1%)/HB-3(5)/ET-1(30)/LiF(1)/Al(80)

Example 9

An organic EL device of Example 9 was manufactured in the same manner as the organic EL device of Example 7 except that the compound MT-5 was used in place of the compound MT-4 in the emitting layer of Example 7. A device arrangement of the organic EL device of Example 9 is roughly shown as follows.
ITO(70)/HI(5)/HT-1(65)/HT-2(10)/MT-5: MT-9: MT-10 (25, 49%: 50%: 1%)/HB-3(5)/ET-1(30)/LiF(1)/Al(80)

Example 10

An organic EL device of Example 10 was manufactured in the same manner as the organic EL device of Example 7 except that the compound MT-7 was used in place of the compound MT-4 in the emitting layer of Example 7. A device arrangement of the organic EL device of Example 10 is roughly shown as follows.
ITO(70)/HI(5)/HT-1(65)/HT-2(10)/MT-7: MT-9: MT-10 (25, 49%: 50%: 1%)/HB-3(5)/ET-1(30)/LiF(1)/Al(80)

Example 11

An organic EL device of Example 11 was manufactured in the same manner as the organic EL device of Example 7 except that the compound MT-8 was used in place of the compound MT-4 in the emitting layer of Example 7. A device arrangement of the organic EL device of Example 11 is roughly shown as follows.
ITO(70)/HI(5)/HT-1(65)/HT-2(10)/MT-8: MT-9: MT-10 (25, 49%: 50%: 1%)/HB-3(5)/ET-1(30)/LiF(1)/Al(80)

Comparative Example 3

An organic EL device of Comparative Example 3 was manufactured in the same manner as the organic EL device of Example 7 except that the organic EL device included a 25-nm-thick emitting layer prepared by co-depositing the compounds MT-9 and MT-10 in place of the emitting layer of Example 7. In the emitting layer of the organic EL device of Comparative Example 3, the respective concentrations of the compounds MT-10 and MT-9 were 1 mass % and 99 mass %. A device arrangement of the organic EL device of Comparative Example 3 is roughly shown as follows.
ITO(70)/HI(5)/HT-1(65)/HT-2(10)/MT-9: MT-10(25, 99%: 1%)/HB-3(5)/ET-1(30)/LiF(1)/Al(80)

Evaluation of Organic EL Devices

The manufactured organic EL devices of Examples 7 to 11 and Comparative Example 3 were evaluated in the same manner as described above. Evaluation items were drive voltage, luminance, CIE1931 chromaticity, current efficiency L/J, electrical power efficiency η, main peak wavelength $\lambda_p$ and external quantum efficiency EQE. The results are shown in Table 9.

TABLE 9

|  | Voltage [V] | Current Density [mA/cm$^2$] | Luminance [cd/m$^2$] | Chromaticity x | Chromaticity y | L/J [cd/A] | η [lm/W] | EQE [%] | λp [nm] |
| --- | --- | --- | --- | --- | --- | --- | --- | --- | --- |
| Ex. 7 | 3.79 | 10 | 5909.6 | 0.464 | 0.527 | 59.10 | 48.97 | 18.00 | 561 |
| Ex. 8 | 3.49 | 10 | 6182.2 | 0.466 | 0.525 | 61.82 | 55.67 | 18.88 | 561 |
| Ex. 9 | 3.46 | 10 | 6936.5 | 0.466 | 0.526 | 69.36 | 63.06 | 21.18 | 560 |
| Ex. 10 | 2.99 | 10 | 6700.3 | 0.464 | 0.528 | 67.00 | 70.31 | 20.50 | 560 |
| Ex. 11 | 3.26 | 10 | 5966.1 | 0.469 | 0.524 | 59.66 | 57.43 | 18.50 | 561 |
| Comp. 3 | 2.99 | 10 | 4920.1 | 0.475 | 0.519 | 49.20 | 51.74 | 15.16 | 562 |

As shown in Table 9, the organic EL devices of Examples 7 to 11 were higher in luminous efficiency than the organic EL device of Comparative Example 3. The organic EL device of Comparative Example 3 included the emitting layer consisting solely of the compounds MT-9 and MT-10. As compared with the organic EL device of Comparative Example 3, the organic EL devices of Examples 7 to 11 each included the emitting layer further containing the third material. Specifically, the emitting layers of Examples 7 to 11 respectively contained the compounds MT-4, MT-6, MT-5, MT-7 and MT-8 as the third material. Consequently, the organic EL devices of Examples 7 to 11 were higher in current efficiency and external quantum efficiency than the organic EL device of Comparative Example 3.

Example 12

An organic EL device of Example 12 was manufactured in the same manner as the organic EL device of Example 2 except that the compound MT-11 was used in place of the compound MT-10 in the emitting layer of Example 2. A device arrangement of the organic EL device of Example 12 is roughly shown as follows.

ITO(70)/HI(5)/HT-1(65)/HT-2(10)/MT-4: MT-9: MT-11 (25, 49%: 50%: 1%)/HB-2(5)/ET-1(30)/LiF(1)/Al(80)

Example 13

An organic EL device of Example 13 was manufactured in the same manner as the organic EL device of Example 12 except that the compound MT-6 was used in place of the compound MT-4 in the emitting layer of Example 12. A device arrangement of the organic EL device of Example 13 is roughly shown as follows.

ITO(70)/HI(5)/HT-1(65)/HT-2(10)/MT-6: MT-9: MT-11 (25, 49%: 50%: 1%)/HB-2(5)/ET-1(30)/LiF(1)/Al(80)

Example 14

An organic EL device of Example 14 was manufactured in the same manner as the organic EL device of Example 12 except that the compound MT-7 was used in place of the compound MT-4 in the emitting layer of Example 12. A device arrangement of the organic EL device of Example 14 is roughly shown as follows.

ITO(70)/HI(5)/HT-1(65)/HT-2(10)/MT-7: MT-9: MT-11 (25, 49%: 50%: 1%)/HB-2(5)/ET-1(30)/LiF(1)/Al(80)

Example 15

An organic EL device of Example 15 was manufactured in the same manner as the organic EL device of Example 12 except that the compound MT-8 was used in place of the compound MT-4 in the emitting layer of Example 12. A device arrangement of the organic EL device of Example 15 is roughly shown as follows.

ITO(70)/HI(5)/HT-1(65)/HT-2(10)/MT-8: MT-9: MT-11 (25, 49%: 50%: 1%)/HB-2(5)/ET-1(30)/LiF(1)/Al(80)

Comparative Example 4

An organic EL device of Comparative Example 4 was manufactured in the same manner as the organic EL device of Example 12 except that the organic EL device included a 25-nm-thick emitting layer prepared by co-depositing the compounds MT-9 and MT-11 in place of the emitting layer of Example 12. In the emitting layer of the organic EL device of Comparative Example 4, the respective concentrations of the compounds MT-11 and MT-9 were 1 mass % and 99 mass %. A device arrangement of the organic EL device of Comparative Example 4 is roughly shown as follows.

ITO(70)/HI(5)/HT-1(65)/HT-2(10)/MT-9:MT-11(25, 99%:1%)/HB-2(5)/ET-1(30)/LiF(1)/Al(80)

Evaluation of Organic EL Devices

The manufactured organic EL devices of Examples 12 to 15 and Comparative Example 4 were evaluated in the same manner as described above. Evaluation items were drive voltage, luminance, CIE1931 chromaticity, current efficiency L/J, electrical power efficiency η, main peak wavelength λp and external quantum efficiency EQE. The results are shown in Table 10.

TABLE 10

| | Voltage [V] | Current Density [mA/cm$^2$] | Luminance [cd/m$^2$] | Chromaticity x | Chromaticity y | L/J [cd/A] | η [lm/W] | EQE [%] | λp [nm] |
| --- | --- | --- | --- | --- | --- | --- | --- | --- | --- |
| Ex. 12 | 4.02 | 10 | 5438.6 | 0.451 | 0.538 | 54.39 | 42.53 | 16.46 | 558 |
| Ex. 13 | 3.36 | 10 | 6290.3 | 0.452 | 0.538 | 62.90 | 58.76 | 18.97 | 559 |
| Ex. 14 | 3.06 | 10 | 6060.6 | 0.455 | 0.536 | 60.61 | 62.25 | 18.52 | 560 |
| Ex. 15 | 3.29 | 10 | 5020.2 | 0.465 | 0.527 | 50.20 | 47.91 | 15.66 | 562 |
| Comp. 4 | 3.07 | 10 | 4380.9 | 0.466 | 0.527 | 43.81 | 44.84 | 13.43 | 560 |

As shown in Table 10, the organic EL devices of Examples 12 to 15 were higher in luminous efficiency than the organic EL device of Comparative Example 4. The organic EL device of Comparative Example 4 included the emitting layer consisting solely of the compounds MT-9 and MT-11. As compared with the organic EL device of Comparative Example 4, the organic EL devices of Examples 12 to 15 each included the emitting layer further containing the third material. Specifically, the emitting layers of Examples 12 to 15 respectively contained the compounds MT-4, MT-6, MT-7 and MT-8 as the third material. Consequently, the organic EL devices of Examples 12 to 15 were higher in current efficiency and external quantum efficiency than the organic EL device of Comparative Example 4.

Example 16

An organic EL device of Example 16 was manufactured in the same manner as the organic EL device of Example 12 except that the compound HB-3 was used in place of the compound HB-2 in the blocking layer in Example 12. A device arrangement of the organic EL device of Example 16 is roughly shown as follows.

ITO(70)/HI(5)/HT-1(65)/HT-2(10)/MT-4: MT-9: MT-11 (25, 49%: 50%: 1%)/HB-3(5)/ET-1(30)/LiF(1)/Al(80)

Example 17

An organic EL device of Example 17 was manufactured in the same manner as the organic EL device of Example 16 except that the compound MT-6 was used in place of the compound MT-4 in the emitting layer of Example 16. A device arrangement of the organic EL device of Example 17 is roughly shown as follows.

ITO(70)/HI(5)/HT-1(65)/HT-2(10)/MT-6: MT-9: MT-11 (25, 49%: 50%: 1%)/HB-3(5)/ET-1(30)/LiF(1)/Al(80)

Example 18

An organic EL device of Example 18 was manufactured in the same manner as the organic EL device of Example 16 except that the compound MT-7 was used in place of the compound MT-4 in the emitting layer of Example 16. A device arrangement of the organic EL device of Example 18 is roughly shown as follows.

ITO(70)/HI(5)/HT-1(65)/HT-2(10)/MT-7: MT-9: MT-11 (25, 49%: 50%: 1%)/HB-3(5)/ET-1(30)/LiF(1)/Al(80)

Example 19

An organic EL device of Example 19 was manufactured in the same manner as the organic EL device of Example 16 except that the compound MT-8 was used in place of the compound MT-4 in the emitting layer of Example 16. A device arrangement of the organic EL device of Example 19 is roughly shown as follows.

ITO(70)/HI(5)/HT-1(65)/HT-2(10)/MT-8: MT-9: MT-11 (25, 49%: 50%: 1%)/HB-3(5)/ET-1(30)/LiF(1)/Al(80)

Comparative Example 5

An organic EL device of Comparative Example 5 was manufactured in the same manner as the organic EL device of Example 16 except that the organic EL device included a 25-nm-thick emitting layer prepared by co-depositing the compounds MT-9 and MT-1 in place of the emitting layer of Example 16. In the emitting layer of the organic EL device of Comparative Example 5, the respective concentrations of the compounds MT-11 and MT-9 were 1 mass % and 99 mass %. A device arrangement of the organic EL device of Comparative Example 5 is roughly shown as follows.

ITO(70)/HI(5)/HT-1(65)/HT-2(10)/MT-9: MT-11(25, 99%: 1%)/HB-3(5)/ET-1(30)/LiF(1)/Al(80)

Evaluation of Organic EL Devices

The manufactured organic EL devices of Examples 16 to 19 and Comparative Example 5 were evaluated in the same manner as described above. Evaluation items were drive voltage, luminance, CIE1931 chromaticity, current efficiency L/J, electrical power efficiency η, main peak wavelength λp and external quantum efficiency EQE. The results are shown in Table 11.

As shown in Table 11, the organic EL devices of Examples 16 to 19 were higher in luminous efficiency than the organic EL device of Comparative Example 5. The organic EL device of Comparative Example 5 included the emitting layer consisting solely of the compounds MT-9 and MT-11. As compared with the organic EL device of Comparative Example 5, the organic EL devices of Examples 16 to 19 each included the emitting layer further containing the third material. Specifically, the emitting layers of Examples 16 to 19 respectively contained the compounds MT-4, MT-6, MT-7 and MT-8 as the third material. Consequently, the organic EL devices of Examples 16 to 19 were higher in current efficiency and external quantum efficiency than the organic EL device of Comparative Example 5.

Example 20

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 70-nm thick.

After the glass substrate having the transparent electrode line was cleaned, the glass substrate was mounted on a substrate holder of a vacuum evaporation apparatus. Initially, a compound HI was vapor-deposited on a surface of the glass substrate where the transparent electrode line was provided in a manner to cover the transparent electrode, thereby forming a 5-nm-thick hole injecting layer.

Subsequently, the compound HT-1 was vapor-deposited on the hole injecting layer to form a 65-nm-thick first hole transporting layer on the HI film.

Next, the compound HT-2 was vapor-deposited on the first hole transporting layer to form a 5-nm-thick second hole transporting layer.

Further, the compound CBP was vapor-deposited on the second hole transporting layer to form a 5-nm-thick first blocking layer.

The compounds MT-13, MT-12 and MT-10 were then co-deposited on the first blocking layer to form a 25-nm-thick emitting layer. In the emitting layer, the respective concentration of the compounds MT-10, MT-12 and MT-13 were 1 mass %, 50 mass % and 49 mass %.

The compound HB-2 was then vapor-deposited on the emitting layer to form a 5-nm-thick second blocking layer.

The compound ET-1 was then vapor-deposited on the second blocking layer to form a 30-nm-thick electron transporting layer.

Lithium fluoride (LiF) was then vapor-deposited on the electron transporting layer to form a 1-nm-thick electron injecting electrode (cathode).

TABLE 11

| | Voltage [V] | Current Density [mA/cm$^2$] | Luminance [cd/m$^2$] | Chromaticity x | Chromaticity y | L/J [cd/A] | η [lm/W] | EQE [%] | λp [nm] |
|---|---|---|---|---|---|---|---|---|---|
| Ex. 16 | 4.09 | 10 | 5215.5 | 0.452 | 0.537 | 52.15 | 40.08 | 15.81 | 559 |
| Ex. 17 | 3.39 | 10 | 6310.3 | 0.452 | 0.537 | 63.10 | 58.48 | 19.06 | 559 |
| Ex. 18 | 3.09 | 10 | 6136.5 | 0.454 | 0.537 | 61.36 | 62.49 | 18.76 | 559 |
| Ex. 19 | 3.33 | 10 | 5234.3 | 0.463 | 0.529 | 52.34 | 49.45 | 16.31 | 562 |
| Comp. 5 | 3.16 | 10 | 4455.9 | 0.464 | 0.529 | 44.56 | 44.36 | 13.61 | 560 |

A metal aluminum (Al) was then vapor-deposited on the electron injecting electrode to form an 80-nm-thick metal Al cathode.

A device arrangement of the organic EL device of Example 20 is roughly shown as follows.

manner as described above. Evaluation items were drive voltage, luminance, CIE1931 chromaticity, current efficiency L/J, electrical power efficiency η, main peak wavelength λp and external quantum efficiency EQE. The results are shown in Table 12.

TABLE 12

|  | Voltage [V] | Current Density [mA/cm$^2$] | Luminance [cd/m$^2$] | Chromaticity x | Chromaticity y | L/J [cd/A] | η [lm/W] | EQE [%] | λp [nm] |
|---|---|---|---|---|---|---|---|---|---|
| Ex. 20 | 4.14 | 10 | 3775.5 | 0.423 | 0.556 | 37.76 | 28.62 | 11.12 | 555 |
| Ex. 21 | 4.67 | 10 | 4582.5 | 0.410 | 0.561 | 45.82 | 30.85 | 13.32 | 554 |
| Ex. 22 | 4.72 | 10 | 4892.1 | 0.406 | 0.563 | 48.92 | 32.55 | 14.20 | 553 |
| Comp. 6 | 4.00 | 10 | 1950.7 | 0.460 | 0.529 | 19.51 | 15.33 | 6.13 | 562 |

ITO(70)/HI(5)/HT-1(65)/HT-2(5)/CBP(5)/MT-13: MT-12: MT-10(25, 49%: 50%: 1%)/HB-2(5)/ET-1(30)/LiF(1)/Al(80)

Example 21

An organic EL device of Comparative Example 21 was manufactured in the same manner as the organic EL device of Example 20 except that the concentrations of the compounds MT-10, MT-12 and MT-13 contained in the emitting layer of Example 20 were respectively changed to 1 mass %, 25 mass % and 74 mass %. A device arrangement of the organic EL device of Example 21 is roughly shown as follows.

ITO(70)/HI(5)/HT-1(65)/HT-2(5)/CBP(5)/MT-13: MT-12: MT-10(25, 74%: 25%: 1%)/HB-2(5)/ET-1(30)/LiF(1)/Al(80)

Example 22

An organic EL device of Comparative Example 22 was manufactured in the same manner as the organic EL device of Example 20 except that the compound MT-5 was used in place of the compound MT-13 in the emitting layer of Example 20, and the concentrations of the compounds MT-10, MT-12 and MT-5 contained in the emitting layer were respectively changed to 1 mass %, 24 mass % and 75 mass %. A device arrangement of the organic EL device of Example 22 is roughly shown as follows.

ITO(70)/HI(5)/HT-1(65)/HT-2(5)/CBP(5)/MT-5: MT-12: MT-10(25, 75%: 24%: 1%)/HB-2(5)/ET-1(30)/LiF(1)/Al(80)

Comparative Example 6

An organic EL device of Comparative Example 6 was manufactured in the same manner as the organic EL device of Example 20 except that the organic EL device included a 25-nm-thick emitting layer prepared by co-depositing the compounds MT-12 and MT-10 in place of the emitting layer of Example 20. In the emitting layer of the organic EL device of Comparative Example 6, the respective concentrations of the compounds MT-10 and MT-12 were 1 mass % and 99 mass %. A device arrangement of the organic EL device of Comparative Example 6 is roughly shown as follows.

ITO(70)/HI(5)/HT-1(65)/HT-2(5)/CBP(5)/MT-12: MT-10(25, 99%: 1%)/HB-2(5)/ET-1(30)/LiF(1)/Al(80)

Evaluation of Organic EL Devices

The manufactured organic EL devices of Examples 20 to 22 and Comparative Example 6 were evaluated in the same As shown in Table 12, the organic EL devices of Examples 20 to 22 were higher in luminous efficiency than the organic EL device of Comparative Example 6. The organic EL device of Comparative Example 6 included the emitting layer consisting solely of the compounds MT-10 and MT-12. As compared with the organic EL device of Comparative Example 6, the organic EL devices of Examples 20 to 22 each included the emitting layer further containing the third material. Specifically, the emitting layers of Examples 20 and 21 each contained the compound MT-13 as the third material, and the emitting layer of Example 22 contained MT-5 as the third material. Consequently, the organic EL devices of Examples 20 to 22 were higher in current efficiency, electrical power efficiency and external quantum efficiency than the organic EL device of Comparative Example 6.

Example 23

An organic EL device of Example 23 was manufactured in the same manner as the organic EL device of Example 20 except that the compound HB-3 was used in place of the compound HB-2 in the blocking layer of Example 20. A device arrangement of the organic EL device of Example 23 is roughly shown as follows.

ITO(70)/HI(5)/HT-1(65)/HT-2(5)/CBP(5)/MT-13: MT-12: MT-10(25, 49%: 50%: 1%)/HB-3(5)/ET-1(30)/LiF(1)/Al(80)

Example 24

An organic EL device of Comparative Example 24 was manufactured in the same manner as the organic EL device of Example 23 except that the concentrations of the compounds MT-10, MT-12 and MT-13 contained in the emitting layer of Example 23 were respectively changed to 1 mass %, 25 mass % and 74 mass %. A device arrangement of the organic EL device of Example 24 is roughly shown as follows.

ITO(70)/HI(5)/HT-1(65)/HT-2(5)/CBP(5)/MT-13: MT-12: MT-10(25, 74%: 25%: 1%)/HB-3(5)/ET-1(30)/LiF(1)/Al(80)

Example 25

An organic EL device of Comparative Example 25 was manufactured in the same manner as the organic EL device of Example 23 except that the compound MT-5 was used in place of the compound MT-13 in the emitting layer of Example 23, and the concentrations of the compounds MT-10, MT-12 and MT-5 contained in the emitting layer were respectively changed to 1 mass %, 24 mass % and 75 mass %. A device arrangement of the organic EL device of Example 25 is roughly shown as follows.

ITO(70)/HI(5)/HT-1(65)/HT-2(5)/CBP(5)/MT-5: MT-12: MT-10(25, 75%: 24%: 1%)/HB-3(5)/ET-1(30)/LiF(1)/Al (80)

Comparative Example 7

An organic EL device of Comparative Example 7 was manufactured in the same manner as the organic EL device of Example 23 except that the organic EL device included a 25-nm-thick emitting layer prepared by co-depositing the compounds MT-12 and MT-10 in place of the emitting layer of Example 23. In the emitting layer of the organic EL device of Comparative Example 7, the respective concentrations of the compounds MT-10 and MT-12 were 1 mass % and 99 mass %. A device arrangement of the organic EL device of Comparative Example 7 is roughly shown as follows.

ITO(70)/HI(5)/HT-1(65)/HT-2(5)/CBP(5)/MT-12: MT-10 (25, 99%: 1%)/HB-3(5)/ET-1(30)/LiF(1)/Al(80)

Evaluation of Organic EL Devices

The manufactured organic EL devices of Examples 23 to 25 and Comparative Example 7 were evaluated in the same manner as described above. Evaluation items were drive voltage, luminance, CIE1931 chromaticity, current efficiency L/J, electrical power efficiency η, main peak wavelength λp and external quantum efficiency EQE. The results are shown in Table 13.

TABLE 13

|  | Voltage [V] | Current Density [mA/cm$^2$] | Luminance [cd/m$^2$] | Chromaticity x | Chromaticity y | L/J [cd/A] | η [lm/W] | EQE [%] | λp [nm] |
| --- | --- | --- | --- | --- | --- | --- | --- | --- | --- |
| Ex. 22 | 4.11 | 10 | 3695.1 | 0.421 | 0.556 | 36.95 | 28.23 | 10.90 | 555 |
| Ex. 23 | 4.65 | 10 | 4445.8 | 0.406 | 0.559 | 44.46 | 30.01 | 12.96 | 553 |
| Ex. 24 | 4.70 | 10 | 5009.2 | 0.402 | 0.559 | 50.09 | 33.47 | 14.59 | 553 |
| Comp. 7 | 4.00 | 10 | 2013.4 | 0.457 | 0.531 | 20.13 | 15.83 | 6.29 | 560 |

As shown in Table 13, the organic EL devices of Examples 23 to 25 were higher in luminous efficiency than the organic EL device of Comparative Example 7. The organic EL device of Comparative Example 7 included the emitting layer consisting solely of the compounds MT-10 and MT-12. As compared with the organic EL device of Comparative Example 7, the organic EL devices of Examples 23 to 25 each included the emitting layer further containing the third material. Specifically, the emitting layers of Examples 23 and 24 each contained the compound MT-13 as the third material, and the emitting layer of Example 25 contained MT-5 as the third material. Consequently, the organic EL devices of Examples 23 to 25 were higher in current efficiency, electrical power efficiency and external quantum efficiency than the organic EL device of Comparative Example 7.

Example 26

An organic EL device of Comparative Example 26 was manufactured in the same manner as the organic EL device of Example 20 except that the compound MT-11 was used in place of the compound MT-10 in the emitting layer of Example 20, and the concentrations of the compounds MT-11, MT-12 and MT-13 contained in the emitting layer were respectively changed to 1 mass %, 25 mass % and 74 mass %. A device arrangement of the organic EL device of Example 26 is roughly shown as follows.

ITO(70)/HI(5)/HT-1(65)/HT-2(5)/CBP(5)/MT-13: MT-12: MT-11(25, 74%: 25%: 1%)/HB-2(5)/ET-1(30)/LiF (1)/Al(80)

Comparative Example 8

An organic EL device of Comparative Example 8 was manufactured in the same manner as the organic EL device of Example 26 except that the organic EL device included a 25-nm-thick emitting layer prepared by co-depositing the compounds MT-12 and MT-11 in place of the emitting layer of Example 26. In the emitting layer of the organic EL device of Comparative Example 8, the respective concentrations of the compounds MT-11 and MT-12 were 1 mass % and 99 mass %. A device arrangement of the organic EL device of Comparative Example 8 is roughly shown as follows.

ITO(70)/HI(5)/HT-1(65)/HT-2(5)/CBP(5)/MT-12: MT-11 (25, 99%: 1%)/HB-2(5)/ET-1(30)/LiF(1)/Al(80)

Evaluation of Organic EL Devices

The manufactured organic EL devices of Example 26 and Comparative Example 8 were evaluated in the same manner as described above. Evaluation items were drive voltage, luminance, CIE1931 chromaticity, current efficiency L/J, electrical power efficiency η, main peak wavelength λp and external quantum efficiency EQE. The results are shown in Table 14.

TABLE 14

|  | Voltage [V] | Current Density [mA/cm$^2$] | Luminance [cd/m$^2$] | Chromaticity x | Chromaticity y | L/J [cd/A] | η [lm/W] | EQE [%] | λp [nm] |
| --- | --- | --- | --- | --- | --- | --- | --- | --- | --- |
| Ex. 26 | 4.83 | 10 | 3817.5 | 0.439 | 0.543 | 38.18 | 24.84 | 11.38 | 559 |
| Comp. 8 | 4.15 | 10 | 1649.0 | 0.486 | 0.508 | 16.49 | 12.48 | 5.37 | 568 |

As shown in Table 14, the organic EL device of Example 26 was higher in luminous efficiency than the organic EL device of Comparative Example 8. The organic EL device of Comparative Example 8 included the emitting layer consisting solely of the compounds MT-11 and MT-12. As compared with the organic EL device of Comparative Example 8, the organic EL device of Example 26 included the emitting layer further containing the third material.

Consequently, the organic EL device of Example 26 was higher in current efficiency, electrical power efficiency and external quantum efficiency than the organic EL device of Comparative Example 8.

Example 27

An organic EL device of Example 27 was manufactured in the same manner as the organic EL device of Example 26 except that the compound HB-3 was used in place of the compound HB-2 in the blocking layer of Example 26. A device arrangement of the organic EL device of Example 27 is roughly shown as follows.

ITO(70)/HI(5)/HT-1(65)/HT-2(5)/CBP(5)/MT-13: MT-12: MT-11(25, 74%: 25%: 1%)/HB-3(5)/ET-1(30)/LiF (1)/Al(80)

Comparative Example 9

An organic EL device of Comparative Example 9 was manufactured in the same manner as the organic EL device of Example 27 except that the organic EL device included a 25-nm-thick emitting layer prepared by co-depositing the compounds MT-12 and MT-11 in place of the emitting layer of Example 27. In the emitting layer of the organic EL device of Comparative Example 9, the respective concentrations of the compounds MT-11 and MT-12 were 1 mass % and 99 mass %. A device arrangement of the organic EL device of Comparative Example 9 is roughly shown as follows.

ITO(70)/HI(5)/HT-1(65)/HT-2(5)/CBP(5)/MT-12: MT-11 (25, 99%: 1%)/HB-3(5)/ET-1(30)/LiF(1)/Al(80)

Evaluation of Organic EL Devices

The manufactured organic EL devices of Example 27 and Comparative Example 9 were evaluated in the same manner as described above. Evaluation items were drive voltage, luminance, CIE1931 chromaticity, current efficiency L/J, electrical power efficiency η, main peak wavelength λp and external quantum efficiency EQE. The results are shown in Table 15.

TABLE 15

| | Voltage [V] | Current Density [mA/cm$^2$] | Luminance [cd/m$^2$] | Chromaticity x | Chromaticity y | L/J [cd/A] | η [lm/W] | EQE [%] | λp [nm] |
|---|---|---|---|---|---|---|---|---|---|
| Ex. 27 | 4.83 | 10 | 3919.6 | 0.437 | 0.543 | 39.20 | 25.51 | 11.67 | 559 |
| Comp. 9 | 4.13 | 10 | 1679.2 | 0.484 | 0.509 | 16.79 | 12.78 | 5.45 | 568 |

As shown in Table 15, the organic EL device of Example 27 was higher in luminous efficiency than the organic EL device of Comparative Example 9. The organic EL device of Comparative Example 9 included the emitting layer consisting solely of the compounds MT-11 and MT-12. As compared with the organic EL device of Comparative Example 9, the organic EL device of Example 27 included the emitting layer further containing the third material. Consequently, the organic EL device of Example 27 was higher in current efficiency, electrical power efficiency and external quantum efficiency than the organic EL device of Comparative Example 9.

The invention claimed is:

1. An organic electroluminescence device, comprising:
    an anode;
    an emitting layer; and
    a cathode,
    wherein the emitting layer comprises a first material, a second material, and a third material, in a same layer,
    wherein the first material is a fluorescent material,
    wherein the second material is a delayed fluorescent material and the second material comprises a moiety of formula (2) below and a moiety of formula (2Y) below in a molecule or the second material is a compound of formula (2A) below;

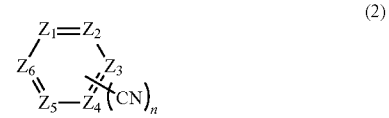

wherein, in the formula (2):
    CN is a cyano group;
    n is an integer in a range from 1 to 5;
    $Z_1$ to $Z_6$ are each independently a nitrogen atom, a carbon atom bonded to CN, or a carbon atom bonded to another atom in the molecule of the second material; and
    a ring is further bonded or is not bonded to a six-membered ring formed by $Z_1$ to $Z_6$,

wherein, in the formula (2Y);
    F and G are each independently a cyclic structure;
    m is 0 or 1; and
    when m is 1, $Y_{20}$ is a single bond, oxygen atom, sulfur atom, selenium atom, carbon atom, silicon atom, or germanium atom,

wherein, in the formula (2A):
    n is an integer of 1 or more;
    t is an integer of 1 or more;
    u is an integer of 0 or more;
    $L_A$ is a substituted or unsubstituted aromatic hydrocarbon ring having 6 to 30 ring carbon atoms or an aromatic heterocycle having 6 to 30 ring atoms;
    CN is a cyano group;
    $D_1$ and $D_2$ are each independently a moiety of formula (2Y), in which:

the cyclic structure F and the cyclic structure G are optionally substituted or unsubstituted;

m is 0 or 1;

when m is 1, $Y_{20}$ is a single bond, an oxygen atom, a sulfur atom, a selenium atom, a carbonyl group, $CR_{21}R_{22}$, $SiR_{23}R_{24}$, or $GeR_{25}R_{26}$, where $R_{21}$ to $R_{26}$ are each independently a hydrogen atom or a substituent, the substituent for $R_{21}$ to $R_{26}$ being selected from the group consisting of a halogen atom, substituted or unsubstituted aryl group having 6 to 30 ring carbon atoms, substituted or unsubstituted aromatic heterocyclic group having 5 to 30 ring atoms, substituted or unsubstituted alkyl group having 1 to 30 carbon atoms, substituted or unsubstituted alkylsilyl group having 3 to 30 carbon atoms, substituted or unsubstituted arylsilyl group having 6 to 60 ring carbon atoms, substituted or unsubstituted alkoxy group having 1 to 30 carbon atoms, substituted or unsubstituted aryloxy group having 6 to 30 ring carbon atoms, substituted or unsubstituted alkylamino group having 2 to 30 carbon atoms, substituted or unsubstituted arylamino group having 6 to 60 ring carbon atoms, substituted or unsubstituted alkylthio group having 1 to 30 carbon atoms, and substituted or unsubstituted arylthio group having 6 to 30 ring carbon atoms;

$D_1$ and $D_2$ are optionally mutually the same or different;

when t is 2 or more, a plurality of $D_1$ are optionally mutually the same or different; and when u is 2 or more, a plurality of $D_2$ are optionally mutually the same or different, wherein a singlet energy of the third material EgS(M3) is larger than a singlet energy of the second material EgS(M2) and the singlet energy of the second material EgS(M2) is larger than a singlet energy EgS(M1) of the first material, and wherein an energy gap $Eg_{77K}$(M3) at 77 [K] of the third material is larger than an energy gap $Eg_{77K}$(M2) at 77 [K] of the second material and the energy gap $Eg_{77K}$(M2) at 77 [K] of the second material is larger than an energy gap $Eg_{77K}$(M1) at 77 [K] of the first material.

2. The organic electroluminescence device according to claim 1, wherein a difference ΔST(M2) between the singlet energy EgS(M2) of the second material and the energy gap $Eg_{77K}$(M2) at 77 [K] of the second material satisfies a relationship of a numerical formula (Numerical Formula 1) below, $ΔST(M2)=EgS(M2)-Eg_{77K}(M2)<0.3$ [eV]   Numerical Formula 1.

3. The organic electroluminescence device according to claim 1, wherein a difference ΔST(M1) between the singlet energy EgS(M1) of the first material and the energy gap $Eg_{77K}$(M1) at 77 [K] of the first material satisfies a relationship of a numerical formula (Numerical Formula 2) below, $ΔST(M1)=EgS(M1)-Eg_{77K}(M1)>0.3$ [eV]   Numerical Formula 2.

4. The organic electroluminescence device according to claim 1, wherein a difference ΔST(M3) between the singlet energy EgS(M3) of the third material and the energy gap $Eg_{77K}$(M3) at 77 [K] of the third material satisfies a numerical formula (Numerical Formula 3) below, $ΔST(M3)=EgS(M3)-Eg_{77K}(M3)>0.3$ [eV]   Numerical Formula 3.

5. The organic electroluminescence device according to claim 1, wherein an ionization potential Ip(M3) of the third material and an ionization potential Ip(M2) of the second material satisfy a relationship of a numerical formula (Numerical Formula 4) below, $Ip(M3)≥Ip(M2)$   (Numerical Formula 4).

6. The organic electroluminescence device according to claim 1, wherein the energy gap $Eg_{77K}$(M3) at 77 [K] of the third material is 2.9 eV or more.

7. The organic electroluminescence device according to claim 1, wherein the ionization potential Ip(M3) of the third material is 6.3 eV or more.

8. The organic electroluminescence device according to claim 1, wherein an electron affinity Af(M3) of the third material is 2.8 eV or more.

9. The organic electroluminescence device according to claim 1, wherein the third material is an aromatic hydrocarbon compound or an aromatic heterocyclic compound.

10. The organic electroluminescence device according to claim 1, wherein the emitting layer comprises no phosphorescent metal complex.

11. The organic electroluminescence device according to claim 1, wherein the first material emits a fluorescent light with a main peak wavelength of 550 nm or less.

12. The organic electroluminescence device according to claim 1, wherein the first material emits a fluorescent light with a main peak wavelength of 480 nm or less.

13. The organic electrolumninescence device according to claim 1, wherein the first material is at least one compound selected from the group consisting of a pyrene derivative, aminoanthracene derivative, aminochrysene derivative, aminopyrene derivative, fluoranthene derivative, fluorene derivative, diamine derivative, triarylamine derivative, and styrylamine derivative.

14. An electronic device comprising the organic electroluminescence device according to claim 1.

15. The organic electroluminescence device according to claim 1, wherein the second material is a compound comprising the moiety of formula (2) and the moiety of formula (2Y) in a molecule.

16. The organic electroluminescence device according to claim 15, wherein the emitting layer comprises no phosphorescent metal complex.

17. The organic electroluminescence device according to claim 15, wherein $Z_1$ to $Z_6$ are each independently a carbon atom bonded to CN or a carbon atom bonded to another atom in the molecule of the second material.

18. The organic electroluminescence device according to claim 17, wherein the emitting layer comprises no phosphorescent metal complex.

19. The organic electroluminescence device according to claim 15, wherein in the formula (2):

n is 2; and $Z_1$ to $Z_6$ are each independently a carbon atom bonded to CN or a carbon atom bonded to another atom in the molecule of the second material.

20. The organic electroluminescence device according to claim 19, wherein, in the formula (2):

two of $Z_1$ to $Z_6$ are carbon atoms bonded to CN; and four of $Z_1$ to $Z_6$ are each a carbon atom bonded to an atom of the moiety of formula (2Y).

21. The organic electroluminescence device according to claim 19, wherein:

the moiety of formula (2) is a six-membered ring; and two cyano groups comprising a first cyano group and a second cyano group are bonded to the six-membered ring, the second cyano group being bonded at an ortho position with respect to the first cyano group.

22. The organic electroluminescence device according to claim 19, wherein:
the moiety of formula (2) is a six-membered ring; and
two cyano groups comprising a first cyano group and a second cyano group are bonded to the six-membered ring, the second cyano group being bonded at a meta position with respect to the first cyano group.

23. The organic electroluminescence device according to claim 19, wherein:
the moiety of formula (2) is a six-membered ring; and
two cyano groups comprising a first cyano group and a second cyano group are bonded to the six-membered ring, the second cyano group being bonded at a para position with respect to the first cyano group.

24. The organic electroluminescence device according to claim 1, wherein:
the moiety of formula (2Y) is a moiety of formula (22) below,

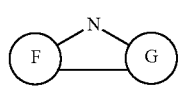

(22)

wherein cyclic structures F and G in the formula (22) are the same as the cyclic structures F and G in the formula (2Y).

25. The organic electroluminescence device according to claim 1, wherein the cyclic structures F and G are six-membered rings.

26. The organic electroluminescence device according to claim 1, wherein the moiety of formula (2Y) is a moiety of one of formulae (2a) and (2x) below,

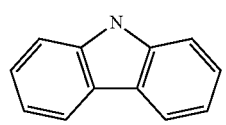

(2a)

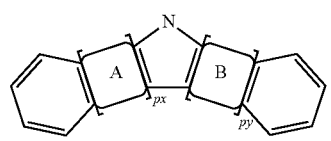

(2x)

wherein, in the formula (2x):
A and B are each independently a cyclic structure of formula (2c) below or a cyclic structure of formula (2d) below, each of the cyclic structure A and the cyclic structure B being fused to an adjacent cyclic structure at any position;
px and py are each independently an integer of 0 to 4 and are respectively the number of the cyclic structure A and the number of the cyclic structure B;
when px is an integer of 2 to 4, a plurality of cyclic structures A are optionally mutually the same or different; and
when py is an integer of 2 to 4, a plurality of cyclic structures B are optionally mutually the same or different,

(2c)

(2d)

wherein, in the formula (2d), $Z_7$ is a carbon atom, nitrogen atom, sulfur atom, or oxygen atom.

27. The organic electroluminescence device according to claim 26, wherein the emitting layer comprises no phosphorescent metal complex.

28. The organic electroluminescence device according to claim 26, wherein the moiety of formula (2x) is a moiety of formula (2b) below,

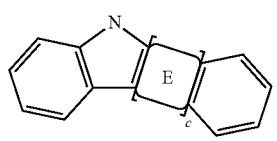

(2b)

wherein, in the formula (2b):
c is an integer of 1 to 4;
when c is an integer of 2 to 4, a plurality of cyclic structures E are optionally mutually the same or different; and
E is a cyclic structure of formula (2c) or a cyclic structure of formula (2d), the cyclic structure E being fused to an adjacent cyclic structure at any position.

29. The organic electroluminescence device according to claim 28, wherein, in the formula (2b):
c is 2; and
the two cyclic structures E include a combination of one cyclic structure of formula (2c) and one cyclic structure of formula (2d).

30. The organic electroluminescence device according to claim 1, wherein the second material is a compound of formula (20) below,

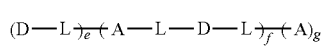

(20)

wherein, in the formula (20)
A is a moiety of formula (2), in which:
CN is a cyano group;
n is an integer of 1 or more;
$Z_1$ to $Z_6$ are each independently a nitrogen atom, a carbon atom bonded to CN, a carbon atom bonded to R, a carbon atom bonded to L, or a carbon atom bonded to D;
at least one of $Z_1$ to $Z_6$ is the carbon atom bonded to CN and at least another one thereof is the carbon atom bonded to L or D;
each R is independently a hydrogen atom or a substituent, the substituent for R being selected from the group consisting of a halogen atom, substituted or unsubstituted aryl group having 6 to 30 ring carbon atoms, substituted or unsubstituted aromatic heterocyclic group having 5 to 30 ring atoms, substituted or unsubstituted alkyl group having 1 to 30 carbon atoms, substituted or unsubstituted alkylsilyl group having 3 to 30 carbon atoms, substituted or unsubstituted arylsilyl group having 6 to 60 ring carbon atoms, substituted or unsubstituted alkoxy group having 1 to 30 carbon atoms, substituted or unsubstituted aryloxy group having 6 to 30 ring carbon atoms, substituted or unsubstituted alkylamino group having 2 to 30 carbon atoms, substituted or unsubstituted arylamino group having 6 to 60 ring carbon atoms, substituted or unsubstituted alkylthio group having 1 to 30 carbon atoms, and substituted or unsubstituted arylthio group having 6 to 30 ring carbon atoms;

D is a moiety of formula (2Y), in which:
the cyclic structure F and the cyclic structure G are substituted or unsubstituted;
m is 0 or 1; and
when m is 1, $Y_{20}$ is a single bond, oxygen atom, sulfur atom, selenium atom, carbonyl group, $CR_{71}R_{22}$, $SiR_{23}R_{24}$ or $GeR_{25}R_{26}$, and $R_{21}$ to $R_{26}$ are each the same as the groups listed for R,
(i) when L is interposed between A and D, L is a single bond, a substituted or unsubstituted aromatic hydrocarbon group having 6 to 14 ring carbon atoms, a substituted or unsubstituted aromatic heterocyclic group having 5 to 14 ring atoms, $CR_{81}R_{82}$, $NR_{83}$, O, S, $SiR_{84}R_{85}$, $CR_{86}R_{87}$-$CR_{88}R_{89}$, $CR_{90}$=$CR_{91}$, a substituted or unsubstituted aliphatic hydrocarbon ring group, or a substituted or unsubstituted aliphatic heterocyclic group, and $R_{81}$ to $R_{91}$ are each independently the same as R described above;
(ii) when L is present at a terminal end in the molecule of the second material, L is the same as R described above;
f is an integer of 1 or more;
e and g are each independently an integer of 0 or more;
a plurality of A are optionally mutually the same or different;
a plurality of D are optionally mutually the same or different; and
a plurality of L are optionally mutually the same or different.

31. The organic electroluminescence device according to claim 30, wherein the compound of formula (20) is a compound of formula (206), formula (214), or formula (216) below:

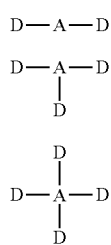

wherein, in the formulae (206), (214), and (216), the plurality of D are optionally mutually the same or different.

32. The organic electroluminescence device according to claim 31, wherein the compound of formula (20) is a compound of formula (216).

33. The organic electroluminescence device according to claim 32, wherein A is a moiety of formula (2), and n is 2.

34. The organic electroluminescence device according to claim 33, wherein:
A is a six-membered ring and
$Z_1$ to $Z_6$ are each independently a carbon atom bonded to CN or a carbon atom bonded to another atom in the molecule of the second material.

35. The organic electroluminescence device according to claim 34, wherein two cyano groups comprising a first cyano group and a second cyano group are bonded to A in the form of the six-membered ring, the second cyano group being bonded at an ortho position with respect to the first cyano group.

36. The organic electroluminescence device according to claim 34, wherein two cyano groups comprising a first cyano group and a second cyano group are bonded to A in the form of the six-membered ring, the second cyano group being bonded at a meta position with respect to the first cyano group.

37. The organic electroluminescence device according to claim 34, wherein two cyano groups comprising a first cyano group and a second cyano group are bonded to A in the form of the six-membered ring, the second cyano group being bonded at a para position with respect to the first cyano group.

38. The organic electroluminescence device according to claim 34, wherein the moiety of formula (2Y) is a moiety of one of formulae (2a) and (2x) below,

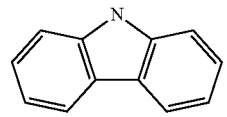

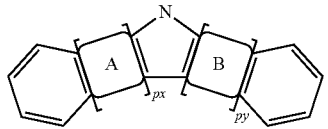

wherein, in the formula (2x):
A and B are each independently a cyclic structure of formula (2c) below or a cyclic structure of formula (2d) below, each of the cyclic structure A and the cyclic structure B being fused to an adjacent cyclic structure at any position
px and py are each independently an integer of 0 to 4 and are respectively the number of the cyclic structure A and the number of the cyclic structure B;
when px is an integer of 2 to 4, a plurality of cyclic structures A are optionally mutually the same or different; and
when py is an integer of 2 to 4, a plurality of cyclic structures B are optionally mutually the same or different,

-continued

(2d)

wherein, in the formula (2d), $Z_7$ is a carbon atom, nitrogen atom, sulfur atom, or oxygen atom.

39. The organic electroluminescence device according to claim 38, wherein the moiety of formula (2x) is a moiety of formula (2b) below,

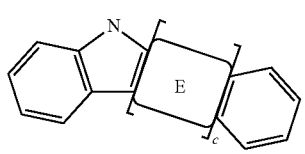
(2b)

wherein, in the formula (2b):
  c is an integer of 1 to 4;
  when c is an integer of 2 to 4, a plurality of cyclic structures E are optionally mutually the same or different; and
  E is a cyclic structure of formula (2c) or a cyclic structure of formula (2d), the cyclic structure E being fused to an adjacent cyclic structure at any position.

40. The organic electroluminescence device according to claim 39, wherein, in formula (2b):
  c is 2; and
  the two cyclic structures E include a combination of one cyclic structure of formula (2c) and one cyclic structure of the formula (2d).

41. The organic electroluminescence device according to claim 31, wherein A is a moiety of formula (2), and n is 2.

42. The organic electroluminescence device according to claim 31, wherein:
  A is a six-membered ring; and
  $Z^1$ to $Z^6$ are each independently a carbon atom bonded to CN or a carbon atom bonded to another atom in the molecule of the second material.

43. The organic electroluminescence device according to claim 42, wherein:
  n is 2; and
  two cyano groups comprising a first cyano group and a second cyano group are bonded to A in the form of the six-membered ring, the second cyano group being bonded at an ortho position with respect to the first cyano group.

44. The organic electroluminescence device according to claim 42, wherein:
  n is 2; and
  two cyano groups comprising a first cyano group and a second cyano group are bonded to A in the form of the six-membered ring, the second cyano group being bonded at a meta position with respect to the first cyano group.

45. The organic electroluminescence device according to claim 42, wherein:
  n is 2; and
  two cyano groups comprising a first cyano group and a second cyano group are bonded to A in the form of the six-membered ring, the second cyano group being bonded at a para position with respect to the first cyano group.

46. The organic electroluminescence device according to claim 31, wherein the moiety of formula (2Y) is a moiety of one of formulae (2a) and (2x) below,

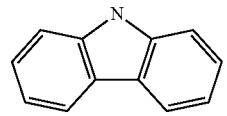
(2a)

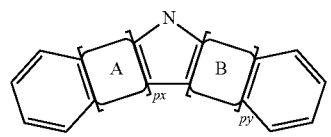
(2x)

wherein, in the formula (2x):
  A and B are each independently a cyclic structure of formula (2c) below or a cyclic structure of formula (2d) below, each of the cyclic structure A and the cyclic structure B being fused to an adjacent cyclic structure at any position;
  px and py are each independently an integer of 0 to 4 and are respectively the number of the cyclic structure A and the number of the cyclic structure B;
  when px is an integer of 2 to 4, a plurality of cyclic structures A are optionally mutually the same or different; and
  when py is an integer of 2 to 4, a plurality of cyclic structures B are optionally mutually the same or different, and

(2c)

(2d)

wherein, in the formula (2d), $Z_7$ is a carbon atom, nitrogen atom, sulfur atom, or oxygen atom.

47. The organic electroluminescence device according to claim 46, wherein the moiety of formula (2x) is a moiety of formula (2b) below,

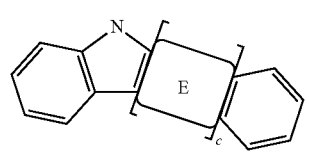
(2b)

wherein, in the formula (2b):
  c is an integer of 1 to 4;
  when c is an integer of 2 to 4, a plurality of cyclic structures E are optionally mutually the same or different; and
  E is a cyclic structure of formula (2c) or a cyclic structure of formula (2d), the cyclic structure E being fused to an adjacent cyclic structure at any position.

48. The organic electroluminescence device according to claim 47, wherein, in formula (2b):
   c is 2; and
   the two cyclic structures E include a combination of one cyclic structure of formula (2c) and one cyclic structure of formula (2d).

49. The organic electroluminescence device according to claim 1, wherein:
   the second material is a compound of formula (2A); and
   $L_A$ is an aromatic hydrocarbon ring having 6 to 10 ring carbon atoms.

50. The organic electroluminescence device according to claim 49, wherein $L_A$ is a benzene ring.

51. The organic electroluminescence device according to claim 50, wherein n is 2.

52. The organic electroluminescence device according to claim 51, wherein t is 4.

53. The organic electroluminescence device according to claim 52, wherein the moiety of formula (2Y) is a moiety of one of formulae (2a) and (2x) below,

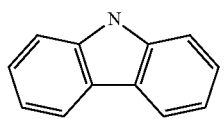

(2a)

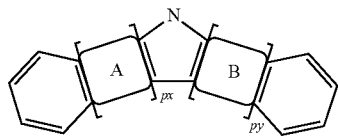

(2x)

wherein, in the formula (2x):
   A and B are each independently a cyclic structure of formula (2c) below or a cyclic structure of formula (2d) below, each of the cyclic structure A and the cyclic structure B being fused to an adjacent cyclic structure at any position;
   px and py are each independently an integer of 0 to 4 and are respectively the number of the cyclic structure A and the number of the cyclic structure B;
   when px is an integer of 2 to 4, a plurality of cyclic structures A are optionally mutually the same or different; and
   when py is an integer of 2 to 4, a plurality of cyclic structures B are optionally mutually the same or different,

(2c)

(2d)

wherein, in the formula (2d), $Z_7$ is a carbon atom, nitrogen atom, sulfur atom, or oxygen atom.

54. The organic electroluminescence device according to claim 53, wherein the moiety of formula (2x) is a moiety of formula (2b) below,

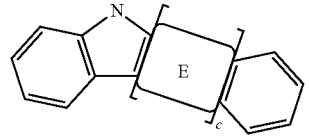

(2b)

wherein, in the formula (2b):
   c is an integer of 1 to 4;
   when c is an integer of 2 to 4, a plurality of cyclic structures E are optionally mutually the same or different; and
   E is a cyclic structure of formula (2c) or a cyclic structure of formula (2d), the cyclic structure E being fused to an adjacent cyclic structure at any position.

55. The organic electroluminescence device according to claim 54, wherein, in the formula (2b):
   c is 2; and
   the two cyclic structures E include a combination of one cyclic structure of formula (2c) and one cyclic structure of formula (2d).

56. The organic electroluminescence device according to claim 51, wherein two cyano groups comprising a first cyano group and a second cyano group are bonded to $L_A$ in the form of the benzene ring, the second cyano group being bonded at an ortho position with respect to the first cyano group.

57. The organic electroluminescence device according to claim 51, wherein two cyano groups comprising a first cyano group and a second cyano group are bonded to $L_A$ in the form of the benzene ring, the second cyano group being bonded at a meta position with respect to the first cyano group.

58. The organic electroluminescence device according to claim 51, wherein two cyano groups comprising a first cyano group and a second cyano group are bonded to $L_A$ in the form of the benzene ring, the second cyano group being bonded at a para position with respect to the first cyano group.

59. The organic electroluminescence device according to claim 49, wherein the $D_1$ or $D_2$ is bonded to a first carbon atom of the aromatic hydrocarbon ring of $L_A$ in formula (2A), and the CN is bonded to a second carbon atom adjacent to the first carbon atom.

60. The organic electroluminescence device according to claim 49, wherein the emitting layer comprises no phosphorescent metal complex.

61. The organic electroluminescence device according to claim 49, wherein the moiety of formula (2Y) is a moiety of one of formulae (2a) and (2x) below,

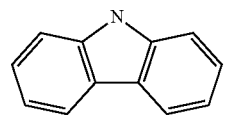

(2a)

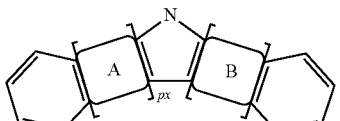

(2x)

wherein, in the formula (2x):

A and B are each independently a cyclic structure of formula (2c) below or a cyclic structure of formula (2d) below, each of the cyclic structure A and the cyclic structure B being fused to an adjacent cyclic structure at any position;

px and py are each independently an integer of 0 to 4 and are respectively the number of the cyclic structure A and the number of the cyclic structure B;

when px is an integer of 2 to 4, a plurality of cyclic structures A are optionally mutually the same or different; and when py is an integer of 2 to 4, a plurality of cyclic structures B are optionally mutually the same or different,

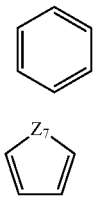

(2c)

(2d)

wherein, in the formula (2d), $Z_7$ is a carbon atom, nitrogen atom, sulfur atom, or oxygen atom.

62. The organic electroluminescence device according to claim 61, wherein the emitting layer comprises no phosphorescent metal complex.

63. The organic electroluminescence device according to claim 61, wherein the moiety of formula (2x) is a moiety of formula (2b) below,

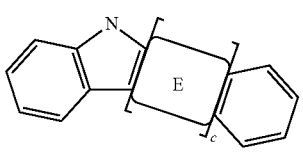

(2b)

wherein, in the formula (2b):

c is an integer of 1 to 4;

when c is an integer of 2 to 4 a plurality of cyclic structures E are optionally mutually the same or different; and E is a cyclic structure of formula (2c) or a cyclic structure of formula (2d), the cyclic structure E being fused to an adjacent cyclic structure at any position.

64. The organic electroluminescence device according to claim 63, wherein, in formula (2b):

c is 2; and the two cyclic structures E include a combination of one cyclic structure of formula (2c) and one cyclic structure of formula (2d).

65. The organic electroluminescence device according to claim 1, wherein the emitting layer does not comprise a compound that comprises a group of formula (30g):

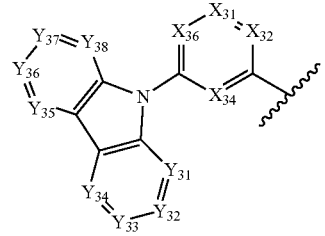

(30g)

wherein:

$Y_{31}$ to $Y_{38}$ are each independently a nitrogen atom, $CR_{37}$ or a carbon atom bonded to another atom in the molecule of the third material;

each $R_{37}$ is independently a hydrogen atom or a substituent;

$X_{31}$, $X_{32}$, $X_{34}$ and $X_{36}$ are each independently a nitrogen atom or $CR_{31}$, $R_{31}$ being a hydrogen atom or a substituent; the substituent for R; and the substituent for $R_{37}$ are each independently selected from the group consisting of a halogen atom, cyano group, substituted or unsubstituted alkyl group having 1 to 30 carbon atoms, substituted or unsubstituted cycloalkyl group having 3 to 30 ring carbon atoms, substituted or unsubstituted trialkylsilyl group, substituted or unsubstituted arylalkylsilyl group, substituted or unsubstituted triarylsilyl group, substituted or unsubstituted diaryl phosphine oxide group, substituted or unsubstituted aromatic hydrocarbon group having 6 to 30 ring carbon atoms, and substituted or unsubstituted heterocyclic group having 5 to 30 ring atoms, the substituted or unsubstituted aromatic hydrocarbon group having 6 to 30 ring carbon atoms for $R_{31}$ being a non-fused ring, the substituted or unsubstituted aromatic hydrocarbon group having 6 to 30 ring carbon atoms for $R_{37}$ being a non-fused ring; and a wavy line shows a bonding position with another atom or another structure in the molecule of the third material.

66. The organic electroluminescence device according to claim 65, wherein the emitting layer does not comprise a compound MT-9:

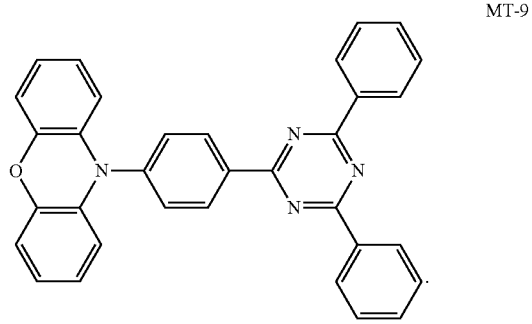 [SMILES: c1ccc(-c2nc(-c3ccccc3)nc(-c3ccc(N4c5ccccc5Oc5ccccc54)cc3)n2)cc1]

MT-9

67. The organic electroluminescence device according to claim 65, wherein the emitting layer does not comprise a compound MT-9 and a compound MT-10:

MT-9

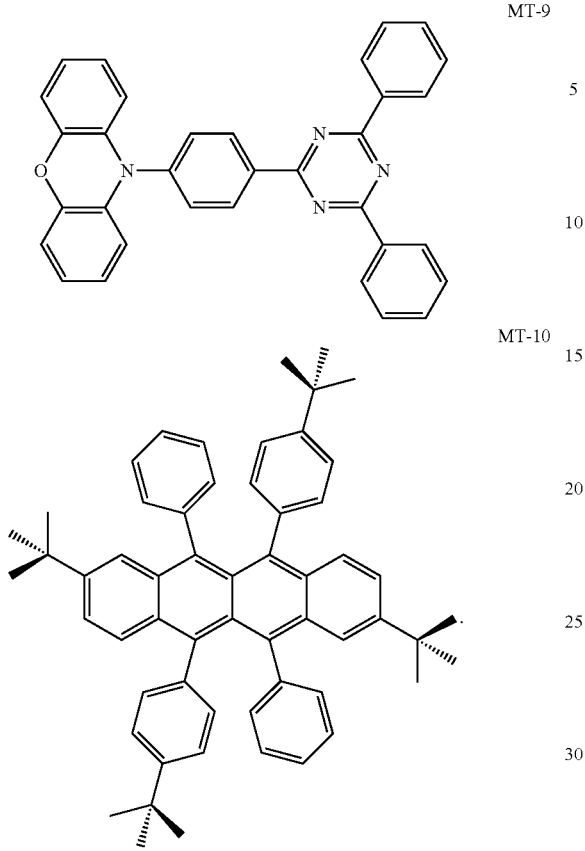

MT-10

68. The organic electroluminescence device according to claim 1, wherein the second material is a compound of formula (20) below,

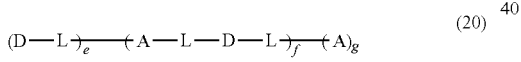     (20)

wherein, in the formula(20):
A is a moiety of formula (2), in which:
CN is a cyano group:
n is an integer of 1 or more;
$Z_1$ to $Z_6$ are each independently a carbon atom bonded to CN, a carbon atom bonded to R, a carbon atom bonded to L, or a carbon atom bonded to D;
at least one of $Z_1$ to $Z_6$ is the carbon atom bonded to CN and at least another one thereof is the carbon atom bonded to L or D;
each R is independently a hydrogen atom or a substituent, the substituent for R being selected from the group consisting of a halogen atom, substituted or unsubstituted aryl group having 6 to 30 ring carbon atoms, substituted or unsubstituted aromatic heterocyclic group having 5 to 30 ring atoms, substituted or unsubstituted alkyl group having 1 to 30 carbon atoms, substituted or unsubstituted alkylsilyl group having 3 to 30 carbon atoms, substituted or unsubstituted arylsilyl group having 6 to 60 ring carbon atoms, substituted or unsubstituted alkoxy group having 1 to 30 carbon atoms, substituted or unsubstituted aryloxy group having 6 to 30 ring carbon atoms, substituted or unsubstituted alkylamino group having 2 to 30 carbon atoms, substituted or unsubstituted arylamino group having 6 to 60 ring carbon atoms, substituted or unsubstituted alkylthio group having 1 to 30 carbon atoms, and substituted or unsubstituted arylthio group having 6 to 30 ring carbon atoms;
the aromatic heterocyclic group for R is a quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, or phenoxazinyl group,
D is a moiety of formula (2Y), in which:
the cyclic structure F and the cyclic structure G are optionally substituted or unsubstituted;
m is 0 or 1; and
when m is 1, $Y_{20}$ is a single bond, oxygen atom, sulfur atom, selenium atom, carbonyl group, $CR_1R_{22}$, $SiR_{23}R_{24}$ or $GeR_{25}R_{26}$, and $R_{21}$ to $R_{26}$ are each the same as the groups listed for R,
(i) when L is interposed between A and D, L is a single bond, a substituted or unsubstituted aromatic hydrocarbon group having 6 to 14 ring carbon atoms, $CR_{81}R_{82}$, $NR_{83}$, O, S, $SiR_{84}R_{85}$, $CR_{86}R_{87}$—$CR_{88}R_{89}$, $CR_{90}$=$CR_{91}$, a substituted or unsubstituted aliphatic hydrocarbon ring group, or a substituted or unsubstituted aliphatic heterocyclic group, and $R_{81}$ to $R_{91}$ are each independently the same as R described above;
(ii) when L is present at a terminal end in the molecule of the second material, L is the same as R described above;
f is an integer of 1 or more;
e and g are each independently an integer of 0 or more;
a plurality of A are optionally mutually the same or different;
a plurality of D are optionally mutually the same or different;
a plurality of L are optionally mutually the same or different;
the substituent meant by "substituted or unsubstituted," the substituent for the cyclic structure F and the substituent for the cyclic structure G are each independently selected from the group consisting of an aryl group, heterocyclic group, alkyl group, alkylsilyl group, arylsilyl group, alkoxy group, aryloxy group, alkylamino group, arylamino group, alkylthio group, arylthio group, alkenyl group, alkynyl group, aralkyl group, halogen atom, cyano group, hydroxyl group, nitro group, and carboxy group; and the heterocyclic group for the substituent meant by "substituted or unsubstituted," the substituent for the cyclic structure F and the substituent for the cyclic structure G is a quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, or phenoxazinyl group.

69. The organic electroluminescence device according to claim 1, wherein the second material does not comprise a substituted or unsubstituted triazinyl group.

70. The organic electroluminescence device according to claim 1, wherein an electron affinity Af(M3) of the third material and an electron affinity Af(M2) of the second material satisfy a relationship of a numerical formula (Numerical Formula 5):

$$Af(M3) \leq Af(M2) \qquad \text{(Numerical Formula 5)}.$$

71. The organic electroluminescence device according to claim 1, wherein a content ratio of the first material in the emitting layer is in a range from 0.01 mass % to 10 mass %.

72. The organic electroluminescence device according to claim 1, wherein a content ratio of the second material in the emitting layer is in a range from 1 mass % to 75 mass %.

73. The organic electroluminescence device according to claim 1, wherein a content ratio of the third material in the emitting layer is in a range from 1 mass % to 75 mass %.

74. The organic electroluminescence device according to claim 1, wherein:
a content ratio of the first material in the emitting layer is in a range from 0.01 mass % r to 10 mass %;
a content ratio of the second material in the emitting layer is in a range from 1 mass % to 75 mass %;
a content ratio of the third material in the emitting layer is in a range from 1 mass % to 75 mass %; and
an upper limit of a total of the respective content ratios of the first to third materials in the emitting layer is 100 mass %.

75. The organic electroluminescence device according to claim 1, wherein the first material is a pyrromethene boron complex compound, a compound having a pyrromethene skeleton, or a metal complex of a compound having a pyrromethene skeleton.

76. The organic electroluminescence device according to claim 1, wherein the third material comprises at least one of a moiety of formula (31) and at least one of a moiety of formula (32) in one molecule:

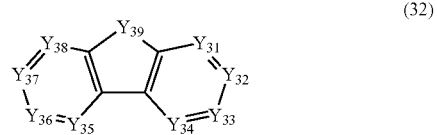

wherein, in formula (31):
$X_{31}$ to $X_{36}$ are each independently a nitrogen atom, or a carbon atom bonded to another atom in the molecule of the third material; and
at least one of $X_{31}$ to $X_{36}$ being the carbon atom bonded to another atom in the molecule of the third material, and
wherein, in formula (32):
$Y_{31}$ to $Y_{38}$ are each independently a nitrogen atom, or a carbon atom bonded to another atom in the molecule of the third material;
at least one of $Y_{31}$ to $Y_{38}$ being the carbon atom bonded to another atom in the molecule of the third material; and
$Y_{39}$ is a nitrogen atom, oxygen atom, or sulfur atom.

77. The organic electroluminescence device according to claim 76, wherein the first material is a pyrromethene boron complex compound, a compound having a pyrromethene skeleton, or a metal complex of a compound having a pyrromethene skeleton.

* * * * *

UNITED STATES PATENT AND TRADEMARK OFFICE
CERTIFICATE OF CORRECTION

PATENT NO. : 10,811,616 B2
APPLICATION NO. : 15/866616
DATED : October 20, 2020
INVENTOR(S) : Toshinari Ogiwara et al.

Page 1 of 1

It is certified that error appears in the above-identified patent and that said Letters Patent is hereby corrected as shown below:

In the Claims

Column 108, Line 23, "R;" should read -- $R_{31}$ --.

Column 109, Line 46, "group:" should read -- group; --.

Column 110, Line 36, "$CR_1R_{22}$," should read -- $CR_{21}R_{22}$, --.

Column 111, Line 45, "mass % r to" should read -- mass % to --.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*